United States Patent
Nussenblatt et al.

(10) Patent No.: US 11,173,195 B2
(45) Date of Patent: Nov. 16, 2021

(54) IMMUNOMODULATORY PHARMACEUTICAL COMPOSITIONS INCLUDING A SYNTHETIC PEPTIDE AND TRANSFORMING GROWTH FACTOR BETA

(71) Applicant: Enzo Biochem, Inc., New York, NY (US)

(72) Inventors: Robert Nussenblatt, Bethesda, MD (US); Baoying Liu, North Potomac, MD (US); Lai Wei, Rockville, MD (US); Elazar Rabbani, New York, NY (US); James J. Donegan, Amesbury, MA (US)

(73) Assignee: Enzo Biochem, Inc., New York, NY (US)

( * ) Notice: Subject to any disclaimer, the term of this patent is extended or adjusted under 35 U.S.C. 154(b) by 0 days.

(21) Appl. No.: 16/889,838

(22) Filed: Jun. 2, 2020

(65) Prior Publication Data
US 2020/0368335 A1 Nov. 26, 2020

Related U.S. Application Data

(60) Continuation of application No. 16/440,007, filed on Jun. 13, 2019, now Pat. No. 10,709,774, which is a division of application No. 15/584,108, filed on May 2, 2017, now abandoned, which is a continuation-in-part of application No. 15/189,531, filed on Jun. 22, 2016, now abandoned, which is a continuation of application No. 13/871,730, filed on Apr. 26, 2013, now abandoned.

(60) Provisional application No. 62/342,447, filed on May 27, 2016.

(51) Int. Cl.
*A61K 38/10* (2006.01)
*C07K 7/04* (2006.01)
*A61K 39/00* (2006.01)
*A61K 35/17* (2015.01)

(52) U.S. Cl.
CPC .......... *A61K 39/0008* (2013.01); *A61K 35/17* (2013.01); *A61K 2039/55583* (2013.01); *A61K 2039/577* (2013.01)

(58) Field of Classification Search
None
See application file for complete search history.

(56) References Cited

U.S. PATENT DOCUMENTS

| | | |
|---|---|---|
| 6,790,447 B1 | 9/2004 | Wildner et al. |
| 7,947,464 B2 | 5/2011 | Fazekas De St Groth et al. |
| 8,372,888 B2 | 2/2013 | Zipkin et al. |
| 2009/0010885 A1 | 1/2009 | Vandenbark et al. |
| 2013/0004513 A1 | 1/2013 | Osterroth et al. |
| 2013/0058901 A1 | 3/2013 | Moldonado et al. |
| 2014/0322188 A1 | 10/2014 | Nussenblatt |
| 2015/0165007 A1 | 6/2015 | Trzonkowski et al. |

FOREIGN PATENT DOCUMENTS

| | | |
|---|---|---|
| EP | 2113560 | 11/2009 |
| WO | WO2009/090651 | 7/2009 |
| WO | WO2012/103187 | 8/2012 |
| WO | WO2013/036914 | 3/2013 |

OTHER PUBLICATIONS

Al-Mahadawi et al., "A simplified method for the isolation of highly purified bovine retinal S antigen," *Journal of Neuroimmunology*, vol. 14, Issue 1, pp. 99-108 (YEAR).
Banga et al., "Antigenicity and uveitogenicity of partially purified peptides of a retinal autoantigen. S-antigen," *Immunology*, vol. 61, No. 3, pp. 357-362 (1987).
Beil et al., *J. Immunol*, vol. 180. pp. 1508-1516 (2008).
Borthwick and Forrester, "Purification of retinal S-antigen by ion-exchange chromatography and chromatofocusing." *Exp. Eye. Res.*, vol. 37, No. 6, pp. 613-625 (1983).
Dong et a., *Ped. Transplant.*, vol. 161, pp. 181-189 (1999).
Goodnow, C.C., *The Lancet*, vol. 357, pp. 2115-2121 (2001).
Haudenschild et al., "Soluble and transmembrane Isoforms of Novel Interleukin-17 Receptor-like Protein by RNA Splicing and Expression in Prostate Cancer," *J. Biol. Chem.*, vol. 277, No. 6. pp. 4309-4316. Figures 1 and 2 (2002).
International Search Report and Written Opinion of copending application PCT/US14/35549, 17 pages.
Kasp et al., An improved method for the purification of retinal S-angigen using selective hydrophobic adsorption chromatography, *J. Immunol. Methods*, vol. 100, pp. 147-152 (1987).
Kraus et al., *Optin Gastroenterol.*, vol. 21. pp. 692-696 (2005).
Kuestner et al., "Identification of the IL-17 Receptor Related Molecule IL-17RC as the ! Receptor for IL-17F," *J. Immunol.*, vol. 179, pp. 5462-5473 (2007).
Lu et al., "Major peptide autoepitopes for nucleosome-specific T cells of human lupus," *The Journal of Clinical Investigation*, vol. 104, No. 3, pp. 345-355 (1999).
Mahlberg, "Purification of Bovine and Human Retinal S-Antigen Using immunoabsorbent Polymer Particles," *Ophthalmic Res.*, vol. 21, pp. 126-133 (1989).
Marketletter, *Marketletter Pubs*, Sep. 13, 1999.
Matta et al., "Antigen Specific Tolerance Inhibits Autoimmune Uveitis in Presensitized Animals via Deletion and CD4-CD25+ T-Regulatory Cells," *Immunol Cell Biol.*, vol. 88, No. 2, p. 187-196 (2010).
Molinotti et al., "One-step purification by high-performance liquid chromatography of retinal S-antigen," *Clinic and Laboratory*, vol. 19, Issue 1, pp. 259-266 (1989).

(Continued)

*Primary Examiner* — G. R. Ewoldt
(74) *Attorney, Agent, or Firm* — David Lansky, Esq.

(57) ABSTRACT

The invention provides immunomodulatory pharmaceutical compositions that include a synthetic peptide and transforming growth factor beta, (TGF-β).

Figure 1:
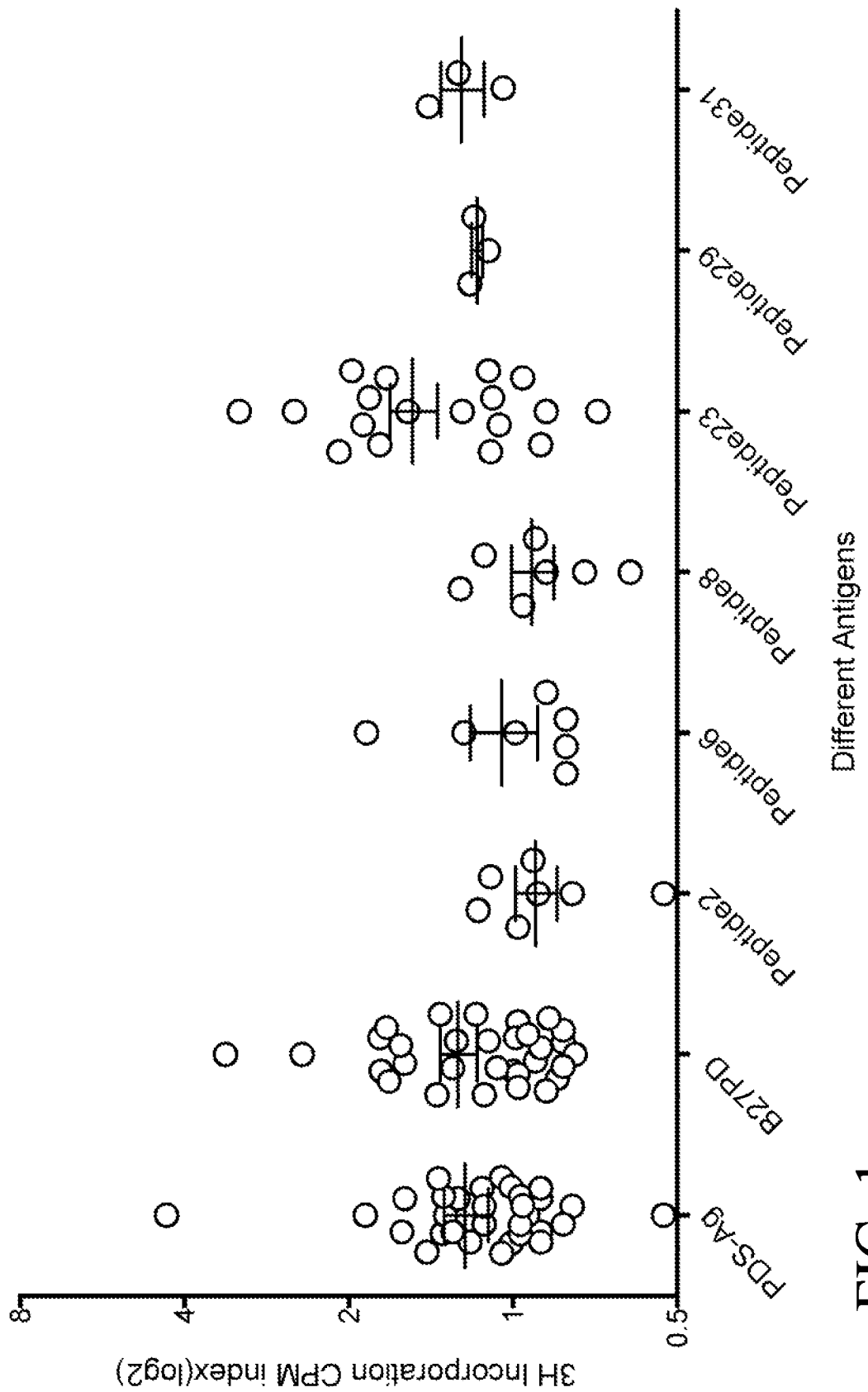

6 Claims, 8 Drawing Sheets
Specification includes a Sequence Listing.

(56) References Cited

OTHER PUBLICATIONS

Nussenblatt et al., *Am. J. Ophamol.*, vol. 158, pp. 5-11 (2014).
Nussenblatt et al., *Ann. N.Y. Acad. Sci.*, p. 325-337 (1996).
Nussenblatt et al., *J. Immunol.*, vol. 144, No. 5. pp, 1689-1695 (1990).
Pozzilli et al., *Diabetol*, vol. 43, pp. 1000-1004 (2000).
Skyler et al., *Diabetes Care*, vol. 28, pp. 1068-1076 (2005).
Thurau et al., Oral Tolerance with an HLA-peptide mimicking retinal autoantigen as a treatmetnof autoimmune uveitis, *Immunolog Letters*, vol. 68. p. 205-212 (1999).
Wei et al., "Hypomethylation of the IL17RC Promoter Associates with Age-Related Macular Degeneration," *Cell Reports*, vol. 2, pp. 1151-1158 (2012).
Adriouch et al., Improved immunological tolerance following combination therapy with CTLA-4/lg and AAV-mediated PD-L1/2 muscle gene transfer, Frontiers in Microbiology 2011, 1-10, 2(199).
Baecher-Allan et al., Human CD4+CD25+regulatory T cells, Seminars in Immunology 2004, 89-97, 16.
Balandina et al., Analysis of CD4+CD25+ cell population in the thymus from myasthenia gravis patients, Ann. N.Y. Acad. Sci. 2003, 275-277, 998.
Becerril et al., HLA B27 as Predisposition Factor to Suffer Age Related Macular Degeneration, Cellular & Molecular Immunology 2009, 303-307, 6(4).
Bollyky et al., Cutting Edge: High Molecular Weight Hyaluronan Promotes the Suppressive Effects of CD4+CD25+ Regulatory T Cells, The Journal of Immunology 2007, 744-747, 179.
Brusko et al., Assessing the in vitro suppressive capacity of regulatory T cells, Immunological Investigations 2007, 607-628, 36.
Cao et al., Enhanced suppressive function of regulatory T cells from patients with immune-mediated diseases following successful ex vivo expansion, Clinical Immunology 2010, 329-337, 136.
Cao et al., Isolation and functional characterization of regulatory CD25brightCD4+ T cells from the target organ of patients with rheumatoid arthritis, Eur. J. Immunol. 2003, 215-223, 33.
Chai et al., In Vitro Expansion Improves In Vivo Regulation by CD4+CD25+ Regulatory T Cells, The Journal of Immunology 2008, 858-869, 180.
Collison and Vignali, In Vitro Treg Suppression Assays, Methods Mol Biol. 2011, 21-37, 707.
Costantino et al., Human regulatory T cells and autoimmunity, Eur. J. Immunol. 2008, 901-937, 38.
Daniel et al., FTY720 Ameliorates Th1-Mediated Colitis in Mice by Directly Affecting the Functional Activity of CD4+CD25+ Regulatory T Cells, The Journal of Immunology 2007, 2458-2468, 178.
De Smet et al., 'Human S-Antigen Determinant Recognition in Uveitis, Invest Ophthalmol Vis Sci. 2001, 3233-3238, 42.
Di Ianni et al., T regulatory cell separation for clinical application, Transfusion and Apheresis Science 2012, 213-216, 47.
Diniz et al., Drusen detection by confocal aperture-modulated infrared scanning laser ophthalmoscopy, Br J Ophthalmol 2013, 285-290, 97.
Dons et al., Induced regulatory T cells: mechanisms of conversion and suppressive potential, Human Immunology 2012, 328-334, 73.
Gershoni et al., Epitope Mapping The First Step in Developing Epitope-Based Vaccines, Biodrugs 2007,145-156, 21 (3).
Horwitz et al., Regulatory T cells generated ex vivo as an approach for the therapy of autoimmune disease, Seminars in Immunology, 2004,135-143, 16.
Kruisbeek et al., Proliferative assays for T cell function, Current Protocols in Immunology 2004, 3.12.1-3.12.20, Supp 60.
Lawendowski et al., Solid-Phase Epitope Recovery: A High Throughput Method for Antigen Identification and Epitope Optimization, The Journal of Immunology 2002, 2414-2421, 169.

Lin and Hunig, Efficient expansion of regulatory T cells in vitro and in vivo with a CD28 superagonist, Eur. J. Immunol. 2003, 626-638, 33.
Li Pira et al., High throughput T epitope mapping and vaccine development, Journal of Biomedicine and Biotechnology, 2010, 1-12.
Ma et al., Adoptive transfer of CD4+CD25+ regulatory cells combined with low-dose siroiimus and anti-thymocyte globulin delays acute rejection of renal allografts in Cynomolgus monkeys, International Immunopharmacology 2011, 618-629, 11.
Marek et al., The Time Is Crucial for Ex Vivo Expansion of T Regulatory Cells for Therapy, Cell Transplantation 2011; 1747-1758, 20.
Marek-Trzonkowska et al., Administration of CD4+CD25highCD127-Regulatory T Cells Preserves beta-Cell Function in Type 1 Diabetes in Children, Diabetes Care 2012, 1817-1820, 35.
Mayer et al., Cord Blood Derived CD4+CD25high T Cells Become Functional Regulatory T Cells upon Antigen Encounter, PLoS ONE 2012, 1-8, 7(1).
Nussenblatt and Ferris, Age-related Macular Degeneration and the Immune Response: Implications for Therapy, Am J Ophthalmol 2007, 618-626, 144.
Putnam et al., Expansion of Human Regulatory T-Cells From Patients With Type 1 Diabetes, Diabetes 2009, 652-662, 58.
Rosenbaum, James T., Eyeing Macular Degeneration—A Few Inflammatory Remarks, N Engl J Med 2012, 768-770, 367(8).
Sugiyama et al., Dysfunctional Blood and Target Tissue CD4+CD25high Regulatory T Cells in Psoriasis: Mechanism: Underlying Unrestrained Pathogenic Effector T Cell Proliferation, The Journal of Immunology 2005, 164-173, 174.
Tang et al., In Vitro-expanded Antigen-specific Regulatory T Cells Suppress Autoimmune Diabetes, J. Exp. Med 2004, 1455-1465, 199(11).
Tarallo et al., DICER1 Loss and Alu RNA Induce Age-Related Macular Degeneration via the NLRP3 Inflammasome and MyD88, Cell 2012, 847-859, 149.
Thornton, Angela M., Fractionation of T and B Cells Using Magnetic Beads, Current Protocols in Immunology, 2003 3.5A.1-3.5A.11.
Trzonkowski et al., First-in-man clinical results of the treatment of patients with graft versus host disease with human ex vivo expanded CD4+CD25+CD127-Tregulatory cells, Clinical Immunology 2009, 22-26, 133.
Ursaciuc et al., Regulatory T cells and TH1/TH2 cytokines as immunodiagnosis keys in systemic autoimmune diseases, Romanian Archives of Microbiology and Immunology 2010, 79-84, 69.
Venken et al., A CFSE based assay for measuring CD4+CD25+ regulatory T cell mediated suppression of auto-antigen specific and polyclonal T cell responses, Journal of Immunological Methods 2007, 1-11, 322.
Viglietta et al., Loss of Functional Suppression by CD4+ CD25+ Regulatory T Cells in Patients with Multiple Sclerosis, J. Exp. Med. 2004, 971-979, 199(7).
Viney et al., Expanding Dendritic Cells In Vivo Enhances the Induction of Oral Tolerance, The Journal of Immunology, 1998, 5815-5825, 160.
Walker et al., De novo generation of antigen-specific CD4+CD25+ regulatory T cells from human CD4+CD25+ cells, Proc. Nat'l. Acad. Sci. 2005, 4103-4108, 102(11).
Wallace et al., Tracking Antigen-Driven Responses by Flow Cytometry: Monitoring Proliferation by Dye Dilution, Cytometry Part A, 2008,1019-1034, 73A.
Weiner et al., Oral Tolerance, Immunol Rev. 2011, 241-259, 241(1).
Yeh et al., CD+Foxp3+ T-regulatory cells in noninfectious uveitis, Arch Opthalmol. 2009, 407-413, 127(4).

SEQUENCE LISTING

```
<160> NUMBER OF SEQ ID NOS: 25

<210> SEQ ID NO 1
<211> LENGTH: 405
<212> TYPE: PRT
<213> ORGANISM: Homo sapiens

<400> SEQUENCE: 1

Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
            20                  25                  30

Arg Asp Tyr Ile Asp His Val Ser Gln Val Gln Pro Val Asp Gly Val
        35                  40                  45

Val Leu Val Asp Pro Asp Leu Val Lys Gly Lys Lys Val Tyr Val Thr
    50                  55                  60

Leu Thr Cys Ala Phe Arg Tyr Gly Gln Glu Asp Val Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
            100                 105                 110

Lys Lys Leu Gly Gly Asn Thr Tyr Pro Phe Leu Leu Thr Phe Pro Asp
        115                 120                 125

Tyr Leu Pro Cys Ser Val Met Leu Gln Pro Ala Pro Gln Asp Ser Gly
    130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Ser Val Arg Tyr
                165                 170                 175

Leu Ile Arg Ser Val Gln His Ala Pro Leu Glu Met Gly Pro Gln Pro
```

```
                180                 185                 190
Arg Ala Glu Ala Thr Trp Gln Phe Phe Met Ser Asp Lys Pro Leu His
            195                 200                 205

Leu Ala Val Ser Leu Asn Arg Glu Ile Tyr Phe His Gly Glu Pro Ile
        210                 215                 220

Pro Val Thr Val Asp Val Thr Asn Asn Thr Glu Lys Thr Val Lys Lys
225                 230                 235                 240

Ile Lys Ala Cys Val Glu Gln Val Ala Asn Val Val Leu Tyr Ser Ser
            245                 250                 255

Asp Tyr Tyr Val Lys Pro Val Ala Met Glu Glu Ala Gln Glu Lys Val
            260                 265                 270

Pro Pro Asn Ser Thr Leu Thr Lys Thr Leu Thr Leu Leu Pro Leu Leu
            275                 280                 285

Ala Asn Asn Arg Glu Arg Arg Gly Ile Ala Leu Asp Gly Lys Ile Lys
            290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
            325                 330                 335

Leu Thr Val Ser Gly Phe Leu Gly Glu Leu Thr Ser Ser Glu Val Ala
            340                 345                 350

Thr Glu Val Pro Phe Arg Leu Met His Pro Gln Pro Glu Asp Pro Ala
            355                 360                 365

Lys Glu Ser Ile Gln Asp Ala Asn Leu Val Phe Glu Glu Phe Ala Arg
            370                 375                 380

His Asn Leu Lys Asp Ala Gly Glu Ala Glu Glu Gly Lys Arg Asp Lys
385                 390                 395                 400

Asn Asp Ala Asp Glu
                405

<210> SEQ ID NO 2
<211> LENGTH: 20
<212> TYPE: PRT
<213> ORGANISM: Artificial Sequence
<220> FEATURE:
<223> OTHER INFORMATION: Synthetic fragment of human S-antigen

<400> SEQUENCE: 2

Gly Glu Pro Ile Pro Val Thr Val Asp Val Thr Asn Asn Thr Glu Lys
1               5                   10                  15

Thr Val Lys Lys
            20

<210> SEQ ID NO 3
<211> LENGTH: 15
<212> TYPE: PRT
<213> ORGANISM: Artificial Sequence
<220> FEATURE:
<223> OTHER INFORMATION: Synthetic fragment of human S-antigen

<400> SEQUENCE: 3

Val Thr Val Asp Val Thr Asn Asn Thr Glu Lys Thr Val Lys Lys
1               5                   10                  15

<210> SEQ ID NO 4
<211> LENGTH: 14
<212> TYPE: PRT
<213> ORGANISM: Artificial Sequence
<220> FEATURE:
```

```
<223> OTHER INFORMATION: Synthetic HLA peptide B27PD

<400> SEQUENCE: 4

Ala Leu Asn Glu Asp Leu Ser Ser Trp Thr Ala Ala Asp Thr
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Synthetic fragment of human S-antigen

<400> SEQUENCE: 5

Ile Phe Lys Lys Ile Ser Arg Asp Lys Ser Val Thr Ile Tyr Leu
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic fragment of human S-antigen

<400> SEQUENCE: 6

Val Lys Gly Lys Lys Val Tyr Val Thr Leu Thr Cys Ala Phe Arg
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic fragment of human S-antigen

<400> SEQUENCE: 7

Tyr Gly Gln Glu Asp Val Asp Val Ile Gly Leu Thr Phe Arg Arg
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic fragment of human S-antigen

<400> SEQUENCE: 8

Leu Pro Leu Leu Ala Asn Asn Arg Glu Arg Arg Gly Ile Ala Leu
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic fragment of human S-antigen

<400> SEQUENCE: 9

Asp Thr Asn Leu Ala Ser Ser Thr Ile Ile Lys Glu Gly Ile Asp
1               5                   10                  15

<210> SEQ ID NO 10
<211> LENGTH: 14
<212> TYPE: PRT
<213> ORGANISM: Artificial Sequence
<220> FEATURE:
<223> OTHER INFORMATION: Synthetic peptide
```

-continued

```
<400> SEQUENCE: 10

Ala Leu Asn Glu Asp Leu Ser Ser Trp Thr Ala Ala Asp Thr
1               5                   10

<210> SEQ ID NO 11
<211> LENGTH: 405
<212> TYPE: PRT
<213> ORGANISM: Homo sapiens

<400> SEQUENCE: 11

Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
            20                  25                  30

Arg Asp Tyr Ile Asp His Val Ser Gln Val Gln Pro Val Asp Gly Val
        35                  40                  45

Val Leu Val Asp Pro Asp Leu Val Lys Gly Lys Lys Val Tyr Val Thr
    50                  55                  60

Leu Thr Cys Ala Phe Arg Tyr Gly Gln Glu Asp Ile Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
            100                 105                 110

Lys Lys Leu Gly Ser Asn Thr Tyr Pro Phe Leu Leu Thr Phe Pro Asp
        115                 120                 125

Tyr Leu Pro Cys Ser Val Met Leu Gln Pro Ala Pro Gln Asp Ser Gly
    130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Ser Val Arg Leu
                165                 170                 175

Leu Ile Arg Lys Val Gln His Ala Pro Leu Glu Met Gly Pro Gln Pro
            180                 185                 190

Arg Ala Glu Ala Ala Trp Gln Phe Phe Met Ser Asp Lys Pro Leu His
        195                 200                 205

Leu Ala Val Ser Leu Asn Lys Glu Ile Tyr Phe His Gly Glu Pro Ile
    210                 215                 220

Pro Val Thr Val Thr Val Thr Asn Asn Thr Glu Lys Thr Val Lys Lys
225                 230                 235                 240

Ile Lys Ala Phe Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
            260                 265                 270

Pro Pro Asn Ser Thr Leu Thr Lys Thr Leu Thr Leu Pro Leu Leu
        275                 280                 285

Ala Asn Asn Arg Glu Arg Arg Gly Ile Ala Leu Asp Gly Lys Ile Lys
    290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Glu Leu Thr Ser Ser Glu Val Ala
            340                 345                 350
```

```
Thr Glu Val Pro Phe Arg Leu Met His Pro Gln Pro Glu Asp Pro Ala
        355                 360                 365

Lys Glu Ser Tyr Gln Asp Ala Asn Leu Val Phe Glu Glu Phe Ala Arg
    370                 375                 380

His Asn Leu Lys Asp Ala Gly Glu Ala Glu Gly Lys Arg Asp Lys
385                 390                 395                 400

Asn Asp Val Asp Glu
            405

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa at position 6 can be any amino acid or no
      amino acid
<220> FEATURE:
<221> NAME/KEY: MISC_FEATURE
<222> LOCATION: (8)..(8)
<223> OTHER INFORMATION: Xaa at position 8 can be any amino acid
<220> FEATURE:
<221> NAME/KEY: MISC_FEATURE
<222> LOCATION: (9)..(9)
<223> OTHER INFORMATION: Xaa at position 9 can be any amino acid

<400> SEQUENCE: 12

Val Thr Val Asp Val Xaa Asn Xaa Xaa Glu Lys
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa at position 6 can be any amino acid

<400> SEQUENCE: 13

Val Thr Val Asp Val Xaa Asn Ser Ser Glu Lys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Val Thr Val Asp Val Asn Ser Ser Glu Lys
1               5                   10

<210> SEQ ID NO 15
<211> LENGTH: 688
<212> TYPE: PRT
<213> ORGANISM: Homo sapiens

<400> SEQUENCE: 15

Met Pro Val Pro Trp Phe Leu Leu Ser Leu Ala Leu Gly Arg Ser Pro
1               5                   10                  15
```

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
            35                  40                  45

Leu Pro Gly Asp Ile Val Pro Ala Pro Gly Pro Val Leu Ala Pro Thr
 50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
            115                 120                 125

Phe Gln Ala Tyr Pro Thr Ala Arg Cys Val Leu Leu Glu Val Gln Val
130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Ala Leu Pro Trp Leu Asn Val Ser Ala Asp Gly Asp Asn Val His Leu
            195                 200                 205

Val Leu Asn Val Ser Glu Glu Gln His Phe Gly Leu Ser Leu Tyr Trp
            210                 215                 220

Asn Gln Val Gln Gly Pro Pro Lys Pro Arg Trp His Lys Asn Leu Thr
225                 230                 235                 240

Gly Pro Gln Ile Ile Thr Leu Asn His Thr Asp Leu Val Pro Cys Leu
                245                 250                 255

Cys Ile Gln Val Trp Pro Leu Glu Pro Asp Ser Val Arg Thr Asn Ile
            260                 265                 270

Cys Pro Phe Arg Glu Asp Pro Arg Ala His Gln Asn Leu Trp Gln Ala
            275                 280                 285

Ala Arg Leu Arg Leu Leu Thr Leu Gln Ser Trp Leu Leu Asp Ala Pro
290                 295                 300

Cys Ser Leu Pro Ala Glu Ala Ala Leu Cys Trp Arg Ala Pro Gly Gly
305                 310                 315                 320

Asp Pro Cys Gln Pro Leu Val Pro Pro Leu Ser Trp Glu Asn Val Thr
                325                 330                 335

Val Asp Val Asn Ser Ser Glu Lys Leu Gln Leu Gln Glu Cys Leu Trp
            340                 345                 350

Ala Asp Ser Leu Gly Pro Leu Lys Asp Val Leu Leu Leu Glu Thr
            355                 360                 365

Arg Gly Pro Gln Asp Asn Arg Ser Leu Cys Ala Leu Glu Pro Ser Gly
            370                 375                 380

Cys Thr Ser Leu Pro Ser Lys Ala Ser Thr Arg Ala Ala Arg Leu Gly
385                 390                 395                 400

Glu Tyr Leu Leu Gln Asp Leu Gln Ser Gly Gln Cys Leu Gln Leu Trp
                405                 410                 415

Asp Asp Asp Leu Gly Ala Leu Trp Ala Cys Pro Met Asp Lys Tyr Ile
            420                 425                 430

```
His Lys Arg Trp Ala Leu Val Trp Leu Ala Cys Leu Leu Phe Ala Ala
            435                 440                 445

Ala Leu Ser Leu Ile Leu Leu Lys Lys Asp His Ala Lys Gly Trp
    450                 455                 460

Leu Arg Leu Leu Lys Gln Asp Val Arg Ser Gly Ala Ala Arg Gly
465                 470                 475                 480

Arg Ala Ala Leu Leu Leu Tyr Ser Ala Asp Asp Ser Gly Phe Glu Arg
                485                 490                 495

Leu Val Gly Ala Leu Ala Ser Ala Leu Cys Gln Leu Pro Leu Arg Val
                500                 505                 510

Ala Val Asp Leu Trp Ser Arg Arg Glu Leu Ser Ala Gln Gly Pro Val
                515                 520                 525

Ala Trp Phe His Ala Gln Arg Arg Gln Thr Leu Gln Glu Gly Gly Val
                530                 535                 540

Val Val Leu Leu Phe Ser Pro Gly Ala Val Ala Leu Cys Ser Glu Trp
545                 550                 555                 560

Leu Gln Asp Gly Val Ser Gly Pro Gly Ala His Gly Pro His Asp Ala
                565                 570                 575

Phe Arg Ala Ser Leu Ser Cys Val Leu Pro Asp Phe Leu Gln Gly Arg
                580                 585                 590

Ala Pro Gly Ser Tyr Val Gly Ala Cys Phe Asp Arg Leu Leu His Pro
                595                 600                 605

Asp Ala Val Pro Ala Leu Phe Arg Thr Val Pro Val Phe Thr Leu Pro
                610                 615                 620

Ser Gln Leu Pro Asp Phe Leu Gly Ala Leu Gln Gln Pro Arg Ala Pro
625                 630                 635                 640

Arg Ser Gly Arg Leu Gln Glu Arg Ala Glu Gln Val Ser Arg Ala Leu
                645                 650                 655

Gln Pro Ala Leu Asp Ser Tyr Phe His Pro Pro Gly Thr Pro Ala Pro
                660                 665                 670

Gly Arg Gly Val Gly Pro Gly Ala Gly Pro Gly Ala Gly Asp Gly Thr
                675                 680                 685

<210> SEQ ID NO 16
<211> LENGTH: 690
<212> TYPE: PRT
<213> ORGANISM: Homo sapiens

<400> SEQUENCE: 16

Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
                20                  25                  30

Cys Ser Pro Gly Leu Ser Cys Arg Leu Trp Asp Ser Asp Ile Leu Cys
            35                  40                  45

Leu Pro Gly Asp Ile Val Pro Ala Pro Gly Pro Val Leu Ala Pro Thr
        50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
                100                 105                 110

Val Glu Glu Pro Arg Asn Ala Ser Leu Gln Ala Gln Val Val Leu Ser
            115                 120                 125
```

```
Phe Gln Ala Tyr Pro Thr Ala Arg Cys Val Leu Leu Glu Val Gln Val
    130                 135                 140
Pro Ala Ala Leu Val Gln Phe Gly Gln Ser Val Gly Ser Val Val Tyr
145                 150                 155                 160
Asp Cys Phe Glu Ala Ala Leu Gly Ser Glu Val Arg Ile Trp Ser Tyr
                165                 170                 175
Thr Gln Pro Arg Tyr Glu Lys Glu Leu Asn His Thr Gln Gln Leu Pro
                180                 185                 190
Asp Cys Arg Gly Leu Glu Val Trp Asn Ser Ile Pro Ser Cys Trp Ala
            195                 200                 205
Leu Pro Trp Leu Asn Val Ser Ala Asp Gly Asp Asn Val His Leu Val
210                 215                 220
Leu Asn Val Ser Glu Glu Gln His Phe Gly Leu Ser Leu Tyr Trp Asn
225                 230                 235                 240
Gln Val Gln Gly Pro Pro Lys Pro Arg Trp His Lys Asn Leu Thr Gly
                245                 250                 255
Pro Gln Ile Ile Thr Leu Asn His Thr Asp Leu Val Pro Cys Leu Cys
                260                 265                 270
Ile Gln Val Trp Pro Leu Glu Pro Asp Ser Val Arg Thr Asn Ile Cys
            275                 280                 285
Pro Phe Arg Glu Asp Pro Arg Ala His Gln Asn Leu Trp Gln Ala Ala
290                 295                 300
Arg Leu Arg Leu Leu Thr Leu Gln Ser Trp Leu Leu Asp Ala Pro Cys
305                 310                 315                 320
Ser Leu Pro Ala Glu Ala Ala Leu Cys Trp Arg Ala Pro Gly Gly Asp
                325                 330                 335
Pro Cys Gln Pro Leu Val Pro Pro Leu Ser Trp Glu Asn Val Thr Val
                340                 345                 350
Asp Val Asn Ser Ser Glu Lys Leu Gln Leu Gln Glu Cys Leu Trp Ala
            355                 360                 365
Asp Ser Leu Gly Pro Leu Lys Asp Asp Val Leu Leu Leu Glu Thr Arg
370                 375                 380
Gly Pro Gln Asp Asn Arg Ser Leu Cys Ala Leu Glu Pro Ser Gly Cys
385                 390                 395                 400
Thr Ser Leu Pro Ser Lys Ala Ser Thr Arg Ala Ala Arg Leu Gly Glu
                405                 410                 415
Tyr Leu Leu Gln Asp Leu Gln Ser Gly Gln Cys Leu Gln Leu Trp Asp
                420                 425                 430
Asp Asp Leu Gly Ala Leu Trp Ala Cys Pro Met Asp Lys Tyr Ile His
            435                 440                 445
Lys Arg Trp Ala Leu Val Trp Leu Ala Cys Leu Leu Phe Ala Ala Ala
450                 455                 460
Leu Ser Leu Ile Leu Leu Leu Lys Lys Asp His Ala Lys Ala Ala Ala
465                 470                 475                 480
Arg Gly Arg Ala Ala Leu Leu Leu Tyr Ser Ala Asp Asp Ser Gly Phe
                485                 490                 495
Glu Arg Leu Val Gly Ala Leu Ala Ser Ala Leu Cys Gln Leu Pro Leu
                500                 505                 510
Arg Val Ala Val Asp Leu Trp Ser Arg Arg Glu Leu Ser Ala Gln Gly
            515                 520                 525
Pro Val Ala Trp Phe His Ala Gln Arg Arg Gln Thr Leu Gln Glu Gly
530                 535                 540
```

Gly Val Val Leu Leu Phe Ser Pro Gly Ala Ala Leu Cys Ser
545                 550                 555                 560

Glu Trp Leu Gln Asp Gly Val Ser Gly Pro Gly Ala His Gly Pro His
                565                 570                 575

Asp Ala Phe Arg Ala Ser Leu Ser Cys Val Leu Pro Asp Phe Leu Gln
            580                 585                 590

Gly Arg Ala Pro Gly Ser Tyr Val Gly Ala Cys Phe Asp Arg Leu Leu
        595                 600                 605

His Pro Asp Ala Val Pro Ala Leu Phe Arg Thr Val Pro Val Phe Thr
    610                 615                 620

Leu Pro Ser Gln Leu Pro Asp Phe Leu Gly Ala Leu Gln Gln Pro Arg
625                 630                 635                 640

Ala Pro Arg Ser Gly Arg Leu Gln Glu Arg Ala Glu Gln Val Ser Arg
                645                 650                 655

Ala Leu Gln Pro Ala Leu Asp Ser Tyr Phe His Pro Pro Gly Thr Pro
            660                 665                 670

Ala Pro Gly Arg Gly Val Gly Pro Gly Ala Gly Pro Gly Ala Gly Asp
        675                 680                 685

Gly Thr
    690

<210> SEQ ID NO 17
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa at position 3 can be any amino acid
<220> FEATURE:
<221> NAME/KEY: MISC_FEATURE
<222> LOCATION: (5)..(5)
<223> OTHER INFORMATION: Xaa at position 5 can be any amino acid
<220> FEATURE:
<221> NAME/KEY: MISC_FEATURE
<222> LOCATION: (7)..(7)
<223> OTHER INFORMATION: Xaa at position 7 can be any amino acid
<220> FEATURE:
<221> NAME/KEY: MISC_FEATURE
<222> LOCATION: (9)..(9)
<223> OTHER INFORMATION: Xaa at position 9 can be any amino acid
<220> FEATURE:
<221> NAME/KEY: MISC_FEATURE
<222> LOCATION: (10)..(10)
<223> OTHER INFORMATION: Xaa at position 10 can be any amino acid
<220> FEATURE:
<221> NAME/KEY: MISC_FEATURE
<222> LOCATION: (11)..(11)
<223> OTHER INFORMATION: Xaa at position 11 can be any amino acid
<220> FEATURE:
<221> NAME/KEY: MISC_FEATURE
<222> LOCATION: (14)..(14)
<223> OTHER INFORMATION: Xaa at position 14 can be any amino acid
<220> FEATURE:
<221> NAME/KEY: MISC_FEATURE
<222> LOCATION: (15)..(15)
<223> OTHER INFORMATION: Xaa at position 15 can be any amino acid

<400> SEQUENCE: 17

Gly Glu Xaa Ile Xaa Val Xaa Val Xaa Xaa Xaa Asn Asn Xaa Xaa Lys
1               5                   10                  15

Thr Val Lys Lys
            20

-continued

```
<210> SEQ ID NO 18
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa at position 3 can be any amino acid
<220> FEATURE:
<221> NAME/KEY: MISC_FEATURE
<222> LOCATION: (5)..(5)
<223> OTHER INFORMATION: Xaa at position 5 can be any amino acid
<220> FEATURE:
<221> NAME/KEY: MISC_FEATURE
<222> LOCATION: (7)..(7)
<223> OTHER INFORMATION: Xaa at position 7 can be any amino acid
<220> FEATURE:
<221> NAME/KEY: MISC_FEATURE
<222> LOCATION: (9)..(9)
<223> OTHER INFORMATION: Xaa at position 9 can be any amino acid
<220> FEATURE:
<221> NAME/KEY: MISC_FEATURE
<222> LOCATION: (10)..(10)
<223> OTHER INFORMATION: Xaa at position 10 can be Val or Ile
<220> FEATURE:
<221> NAME/KEY: MISC_FEATURE
<222> LOCATION: (11)..(11)
<223> OTHER INFORMATION: Xaa at position 11 can be any amino acid
<220> FEATURE:
<221> NAME/KEY: MISC_FEATURE
<222> LOCATION: (14)..(14)
<223> OTHER INFORMATION: Xaa at position 14 can be any amino acid
<220> FEATURE:
<221> NAME/KEY: MISC_FEATURE
<222> LOCATION: (15)..(15)
<223> OTHER INFORMATION: Xaa at position 15 can be any amino acid

<400> SEQUENCE: 18

Gly Glu Ser Ile Ser Val Asn Val His Xaa Gln Asn Asn Ser Asn Lys
1               5                   10                  15

Thr Val Lys Lys
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: Xaa at position 10 can be Val or Ile

<400> SEQUENCE: 19

Gly Glu Ser Ile Ser Val Asn Val His Xaa Gln Asn Asn Ser Asn Lys
1               5                   10                  15

Thr Val Lys Lys
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic peptide

<400> SEQUENCE: 20

Gly Glu Ser Ile Ser Val Asn Val His Ile Gln Asn Asn Ser Asn Lys
1               5                   10                  15
```

Thr Val Lys Lys
            20

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa at position 5 can be any amino acid
<220> FEATURE:
<221> NAME/KEY: MISC_FEATURE
<222> LOCATION: (9)..(9)
<223> OTHER INFORMATION: Xaa at position 9 can be any amino acid

<400> SEQUENCE: 21

Gly Glu Pro Ile Xaa Val Thr Val Xaa Val Thr Asn
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide

<400> SEQUENCE: 22

Gly Glu Pro Ile Thr Val Thr Val Ser Val Thr Asn
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa at position 5 can be any amino acid
<220> FEATURE:
<221> NAME/KEY: MISC_FEATURE
<222> LOCATION: (9)..(9)
<223> OTHER INFORMATION: Xaa at position 9 can be any amino acid

<400> SEQUENCE: 23

Ile Pro Val Thr Xaa Asp Val Thr Xaa Asn
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa at position 5 can be Val or Ile
<220> FEATURE:
<221> NAME/KEY: MISC_FEATURE
<222> LOCATION: (9)..(9)
<223> OTHER INFORMATION: Xaa at position 9 can be Asn or Asp

<400> SEQUENCE: 24

Ile Pro Val Thr Xaa Asp Val Thr Xaa Asn
1               5                   10

```
<210> SEQ ID NO 25
<211> LENGTH: 10
<212> TYPE: PRT
<213> ORGANISM: Artificial Sequence
<220> FEATURE:
<223> OTHER INFORMATION: Synthetic peptide

<400> SEQUENCE: 25

Ile Pro Val Thr Ile Asp Val Thr Asp Asn
1               5                   10
```

IMMUNOMODULATORY PHARMACEUTICAL COMPOSITIONS INCLUDING A SYNTHETIC PEPTIDE AND TRANSFORMING GROWTH FACTOR BETA

1. CROSS-REFERENCE TO RELATED APPLICATIONS

This application is a continuation of U.S. application Ser. No. 16/440,007 filed Jun. 13, 2019 (now U.S. Pat. No. 10,709,774), which is a divisional of U.S. application Ser. No. 15/584,108 filed May 2, 2017, which claims the benefit of U.S. Provisional Application No. 62/342,447 filed May 27, 2016, and which is a continuation-in-part of U.S. application Ser. No. 15/189,531 filed Jun. 22, 2016, which is a continuation of U.S. application Ser. No. 13/871,730 filed Apr. 26, 2013, each of which is hereby incorporated by reference in its entirety.

2. STATEMENT REGARDING FEDERALLY SPONSORED RESEARCH

This invention was made in part with Government support under Cooperative Research and Development Agreement (CRADA) Number 02491 and amendments thereto, executed between Enzo Therapeutics Incorporated and the National Eye Institute, National Institutes of Health.

3. SEQUENCE LISTING STATEMENT

This application contains a Sequence Listing which has been submitted in ASCII format via EFS-Web and is hereby incorporated by reference in its entirety. Said ASCII copy, created on Jul. 1, 2021, is named ENZ-107-CON-CIP-D1-SL.txt and is 27,262 bytes in size.

4. BACKGROUND

The mammalian immune system has two contrasting functions that must co-exist for the health of the organism. On the one hand, the immune system recognizes foreign agents, e.g., "non-self" agents such as bacteria or viruses that it attacks and destroys to restore health to an infected organism. On the other hand, the immune system recognizes the tissues of the organism and non-pathogenic "foreign" substances that are ingested (e.g., food) so that the "self" is not attacked and the organism survives. In order for the regulation of these two functions to co-exist, the immune system must constantly correctly identify "self" and "non-self" to mount a proper response and to maintain a balance between action and selective inaction with respect to various challenges.

Autoimmune diseases result from an imbalance of the immune system, which becomes unable to distinguish "self" from "non-self" and mounts an inappropriate immune response to healthy tissues of the organism. The result of this imbalance is inflammation and tissue damage, which is often irreversible. Today, an autoimmune etiology is known or suspected to play a role in numerous seemingly unrelated diseases such as, uveitis, Crohn's disease, diabetes mellitus type I, lupus erythematosus, myasthenia gravis, psoriasis and rheumatoid arthritis. Increasing evidence suggests that immune mediated mechanisms also play an important role in the pathogenesis of age-related macular degeneration ("AMD"), the leading cause of blindness in the United States and the leading cause of blindness in people over 60 years of age. See, e.g., Tarallo et al. (2012) Cell 149:847-859; Rosenbaum (2012) N Engl J Med. 367(8):768-770; Nussenblatt and Ferris (2007) AMD and the Immune System 144(4):618-626; Becerril et al. (2009) Cellular & Molecular Immunology 6(4):303-307. Accordingly, although AMD has traditionally been thought of as a disease confined to the eye, recent research suggests that it is a systemic immunological disease with local expression.

Current therapies for autoimmune diseases involve suppression of the immune system to mitigate the improper attack on "self" tissues. However, immune suppressive therapies tend to be non-selective, leading to inhibition of not only the aberrant autoimmune response, and but also of healthy responses to pathogens. Accordingly, immunosuppressive therapies can leave patients susceptible to infections, cancer and drug toxicity. Furthermore, suppression of the immune system only addresses one of the two functions of the immune system, which results in further unbalancing the system.

One approach for suppressing diseases that have an autoimmune component is induction of specific immune tolerance to soluble antigens by applying the soluble antigen to mucosal surfaces. See e.g., Weiner et al. (2011) Immunol. Rev. 241(1):241-59. These tolerizing epitopes are administered to a patient in order to upregulate the functions of regulatory T-cells, which are T-cells with particular phenotypes that suppress responder T-cells, cells that are responsible for attacking agents that are recognized as "non-self". While induction of regulatory T-cells by oral administration of a soluble antigen is considered to be a promising approach to treatment of autoimmune diseases, the ability to produce significant numbers of regulatory T-cells has been limited and requires identification of additional strategies (such as identification of a better antigen and/or co-administration of an enhancer of immune tolerance) to induce adequate numbers of functional regulatory cells. See, e.g., Weiner at 249-50.

A more recent approach for suppressing autoimmune disease is to administer regulatory T-cells to the patient. See, e.g., Marek-Trzonkowska et al. (2012) Diabetes Care 35:1817-20. In this study, regulatory autologous T-cells were expanded, but were not trained in the presence of an epitope. Id. at 1818. While this approach appears to have efficacy, it is not known whether it will provide long-term suppression of autoimmune disease. Id. at 1820. Furthermore, regulatory T-cell based therapies may be complicated by low numbers of regulatory T-cells in the body compared to other T-cells and their energy, which means that they do not readily expand to provide enough cells for administration to a patient.

Accordingly, there is a need for improved methods and compositions that restore balance to the immune system of a patient suffering from an autoimmune disease by upregulating the regulatory function of the immune system.

5. SUMMARY

In various aspects, the present disclosure is directed to a method of identifying a compound comprising an epitope that induces immune tolerance in a human patient suffering from an autoimmune disease comprising the step of identifying in vitro a compound from a library or collection of compounds that (a) elicits a response (RespH) from responder T-cells of a healthy individual; (b) elicits a response (RespP) from responder T-cells of the patient; (c) elicits a response (RegH) from regulatory T-cells of a healthy individual; and (d) elicits a response (RegP) from regulatory T-cells of the patient (RegP), wherein the compound that induces a response selected from a RespH/RespP<1, a RegH/RegP≥1, or a RespH/RespP<1 and a RegH/RegP≥1 is identified as the compound that induces immune tolerance. Accordingly, in certain embodiments, a compound that induces immune tolerance is identified by a response in the presence of the compound of responder T-cells of a healthy individual that is lower than a response of responder T-cells of the patient. In other embodiments, a compound that induces immune tolerance is identified by a response in the presence of the compound of regulatory T-cells of a healthy individual that is greater than or equal to a response of regulatory T-cells of the patient. In still other embodiments, a compound that induces immune tolerance is identified by (i) a response in the presence of the compound of responder T-cells of a healthy individual that is lower than a response of responder T-cells of the patient; and (ii) a response in the presence of the compound of regulatory T-cells of a healthy individual that is greater than or equal to a response of regulatory T-cells of the patient.

In certain embodiments, the invention provides a method of identifying a compound comprising an epitope that induces immune tolerance in a human patient suffering from an autoimmune disease comprising the steps of (a) identifying in vitro a compound from a library or collection of compounds that (i) elicits a response ($RespP_1$) from responder T-cells of the patient; and (ii) elicits a response (RespH) from responder T-cells of a healthy individual wherein $RespP_1/RespH>1$ and (b) elicits a response ($RespP_2$) from responder T-cells of the patient in the presence of a responder T-cell antigen and regulatory T-cells, wherein $RespP_2/RespP_1<1$, wherein the compound that induces a $RespP_1/RespH>1$ and $RespP_2/RespP_1<1$ is identified as the compound that induces an immune tolerance. Accordingly, in certain embodiments, a compound that induces immune tolerance in a patient is identified by (i) a response in the presence of the compound of responder T-cells of the patient that is greater than a response from responder T-cells of the patient; and (ii) a response in the presence of the compound of responder T-cells of the patient in the presence of a responder T-cell antigen and regulatory T-cells that is lower than a response from responder T-cells of the patient in the absence of a responder T-cell antigen and regulatory T-cells.

In a more specific embodiment, the invention provides a method of identifying a compound comprising an epitope from a library or collection of compounds that induces immune tolerance in a human patient suffering from an autoimmune disease comprising the steps of (a) exposing human $CD4^+CD25^+$ cells to a compound from a library or collection of compounds; and (b) measuring the proliferation of said $CD4^+CD25^+$ cells in the presence of the compound ($R_1$); and (c) measuring the proliferation of said $CD4^+CD25^+$ cells in the absence of the compound ($R_2$), wherein the compound that induces $R_1/R_2>1$ is identified as the compound that induces immune tolerance. Accordingly, in some embodiments, a compound that induces immune tolerance in a patient is identified by a proliferation response of $CD4^+CD25^+$ cells in the presence of the compound that is greater than a proliferation response in the absence of the compound. In certain embodiments, this assay is performed in the presence of an additional factor, such as IL-2.

In other embodiments, the present disclosure relates to methods of identifying a compound comprising an epitope that induces immune tolerance in a patient suffering from an autoimmune disease using a mixed-cell assay. Thus, in some embodiments, a compound comprising an epitope that induces immune tolerance in a patient suffering from an autoimmune disease is identified in vitro as the compound that elicits a response (RespP) from responder T-cells from the patient in the presence of regulatory T-cells from the patient that is greater than the response (RegP) elicited from the regulatory T-cells of the patient. Accordingly, in some embodiments, an identified compound induces the response RespP/RegP≥1.

In another embodiment of a mixed-cell assay, a compound comprising an epitope that induces immune tolerance in a patient suffering from an autoimmune disease is identified in vitro as a compound that elicits a response (RegH) from regulatory T-cells from a healthy individual in the presence of responder T-cells from the patient that is greater than the response (RespP) elicited from the responder T-cells of the patient. Accordingly, in some embodiments, an identified compound induces the response RegH>RespP.

In yet another embodiment, a compound comprising an epitope that induces immune tolerance in a patient suffering from an autoimmune disease is identified in vitro as a compound that elicits a response (RespH) from responder T-cells from a healthy individual in the presence of regulatory T-cells from the patient that is greater than the response (RegP) elicited from the regulatory T-cells from the patient. Thus, in various embodiments, an identified compound induces the response RespH>RegP.

In other embodiments, a compound comprising an epitope that induces immune tolerance in a patient suffering from an autoimmune disease is identified in vitro as a compound that elicits a response (RespH) from responder T-cells from a healthy individual in the presence of regulatory T-cells from a healthy individual that is lower than the response (RegH) elicited from the regulatory T-cells from the healthy individual. In some embodiments, an identified compound induces the response RespH<RegH.

In still other embodiments, the present disclosure relates to a method of identifying a compound comprising an epitope that induces immune tolerance in a patient suffering from an autoimmune disease comprising the step of identifying in vitro a compound from a library or collection of compounds that (a) elicits a response (RespH) from responder T-cells of a healthy individual and (b) elicits a response (RespP) from responder T-cells of the patient, wherein the compound that induces a RespH/RespP<1 is identified as the compound that induces immune tolerance. Accordingly, in some embodiments, the compound induces a response from responder T-cells of the patient that is greater than the response elicited from responder T-cells of a healthy individual.

The present disclosure further relates to methods of treating a patient suffering from an autoimmune disease. Thus, in some embodiments, the invention provides a method of treating a human patient suffering from an autoimmune disease comprising administering to the patient an effective amount of regulatory T-cells. In certain specific embodiments, the regulatory T-cells are trained ex vivo before administration to the patient in the presence of a compound comprising an epitope that induces immune tolerance, wherein the compound is identified from a library or collection of compounds, wherein the compound (a) elicits a response (RespH) from responder T-cells of a healthy individual; (b) elicits a response (RespP) from responder T-cells of the patient; (c) elicits a response (RegH) from regulatory T-cells of a healthy individual; and (d) elicits a response (RegP) from regulatory T-cells of the patient, and wherein the compound induces a response selected from a response of RespH/RespP<1, a response of RegH/RegP≥1 or a response of RespH/RespP<1 and RegH/RegP≥1. Accordingly, in certain embodiments, the regulatory T-cells are trained in the presence of a compound that elicits a response from responder T-cells of a healthy individual that is lower than a response from responder T-cells of the patient. In other embodiments, the regulatory T-cells are trained in the presence of a compound that elicits a response in the presence of the compound from regulatory T-cells of a healthy individual that is greater than or equal to a response of regulatory T-cells of the patient. In still other embodiments, the regulatory T-cells are trained in the presence of a compound that (i) elicits a response in the presence of the compound from responder T-cells of a healthy individual that is lower than the response from responder T-cells of the patient; and (ii) elicits a response in the presence of the compound from regulatory T-cells of a healthy individual that is greater than or equal to a response from regulatory T-cells of the patient. In other specific embodiments, the regulatory T-cells are expanded, but are not trained, before administration.

In other embodiments, the invention provides a combination therapy method of treating a patient suffering from an autoimmune disease comprising administering to the patient (a) an effective amount of regulatory T-cells; and (b) an effective amount of a compound comprising an epitope that induces immune tolerance. In certain embodiments, the compound is identified from a library or collection of compounds, wherein the compound (i) elicits a response (RespH) from responder T-cells of a healthy individual and a response (RespP) from responder T-cells of the patient; (ii) elicits a response (RegH) from regulatory T-cells of a healthy individual and elicits a response (RegP) from regulatory T-cells of the patient, and wherein the compound induces a RespH/RespP<1 and a RegH/RegP≥1. In certain specific embodiments, the regulatory T-cells are trained ex vivo in the presence of a compound comprising an epitope that induces immune tolerance, wherein the compound is identified from a library or collection of compounds, wherein the compound (i) elicits a response (RespH) from a responder T-cell of a healthy individual and a response (RespP) from a responder T-cell of the patient; (ii) elicits a response (RegH) from a regulatory T-cell of a healthy individual and elicits a response (RegP) from a regulatory T-cell of the patient, and wherein the compound induces a RespH/RespP<1 and a RegH/RegP≥1. Accordingly, in certain embodiments, the compound is identified as a compound that elicits a response from responder T-cells of a healthy individual that is lower than a response from responder T-cells of the patient. In other embodiments, compound is identified as a compound that elicits a response in the presence of the compound from regulatory T-cells of a healthy individual that is greater than or equal to a response of regulatory T-cells of the patient. In still other embodiments, the compound is identified as a compound that (i) elicits a response in the presence of the compound from responder T-cells of a healthy individual that is lower than the response from responder T-cells of the patient; and (ii) elicits a response in the presence of the compound from regulatory T-cells of a healthy individual that is greater than or equal to a response from regulatory T-cells of the patient. In other specific embodiments, the regulatory T-cells are expanded, but are not trained, before administration.

In still other embodiments, the present disclosure relates to a method of treating an autoimmune disease selected from age-related macular degeneration and uveitis in a patient comprising administering to the patient an effective amount of a compound comprising an epitope that induces immune tolerance. The administering step may include administering a compound identified in vitro from a library or collection of compounds, wherein the compound (a) elicits a response (RespH) from responder T-cells of a healthy individual and (b) elicits a response (RespP) from responder T-cells of the patient, and wherein the compound induces a RespH/RespP<1. Accordingly, in certain embodiments, the compound elicits a response from responder T-cells of a healthy individual that is lower than the response elicited from responder T-cells of the patient.

In certain embodiments, the present disclosure relates to methods of monitoring, diagnosing, or prognosticating an autoimmune disease in a patient, which methods comprise the steps of (a) measuring a response (RespH) from responder T-cells of a healthy individual and measuring a response (RespP) from responder T-cells of the patient; (b) measuring a response (RegH) from regulatory T-cells of a healthy individual and measuring a response (RegP) from regulatory T-cells of the patient; or (c) measuring a response (RespH) from responder T-cells of a healthy individual, a response (RespP) from responder T-cells of the patient and measuring a response (RegP) from regulatory T-cells of the patient and a response (RespH) from responder T-cells of a healthy individual in the presence of a compound comprising an epitope identified in vitro from a library or collection of compounds that induces immune tolerance in a human patient, and wherein a comparison of RespH and RespP, or of RegH and RegP, or of both RespH and RespP and RegH and RegP indicates a deviation of the patient's response from the response of a healthy individual.

In additional embodiments, the present disclosure relates to kits for carrying out a method of monitoring, diagnosing, or prognosticating an autoimmune disease in a patient, which comprises (a) a compound comprising an epitope that induces immune tolerance in a human patient; (b) a buffer; (c) a cell growth medium such as a lymphocyte growth medium such as a T-cell growth medium; (d) regulatory T-cells from an healthy individual; (e) responder T-cells from a healthy individual; and (f) at least one enhancer selected from the group consisting of high molecular weight hyaluronic acid, IL-2, IL-15, TGF-β, all-trans retinoic acid, rapamycin, anti-CD3, anti-CD28, vitamin D3, dexamethasone, IL-10, idolamine-2,3-dioxygenase, FTY720, a sphingosine kinase 1 inhibitor, cholera toxin B subunit, ovalbumin, Flt2L, sirolimus and/or anti-thymocyte globulin, CTLA-4/Ig.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

6. BRIEF DESCRIPTION OF THE FIGURES

FIG. 1 shows the immunostimulatory activity of various 15-mer peptide subsequences of human S-antigen and control peptides on peripheral blood mononuclear cells (PBMCs) from patients with wet AMD (advanced AMD with CNV).

Figure 2A:
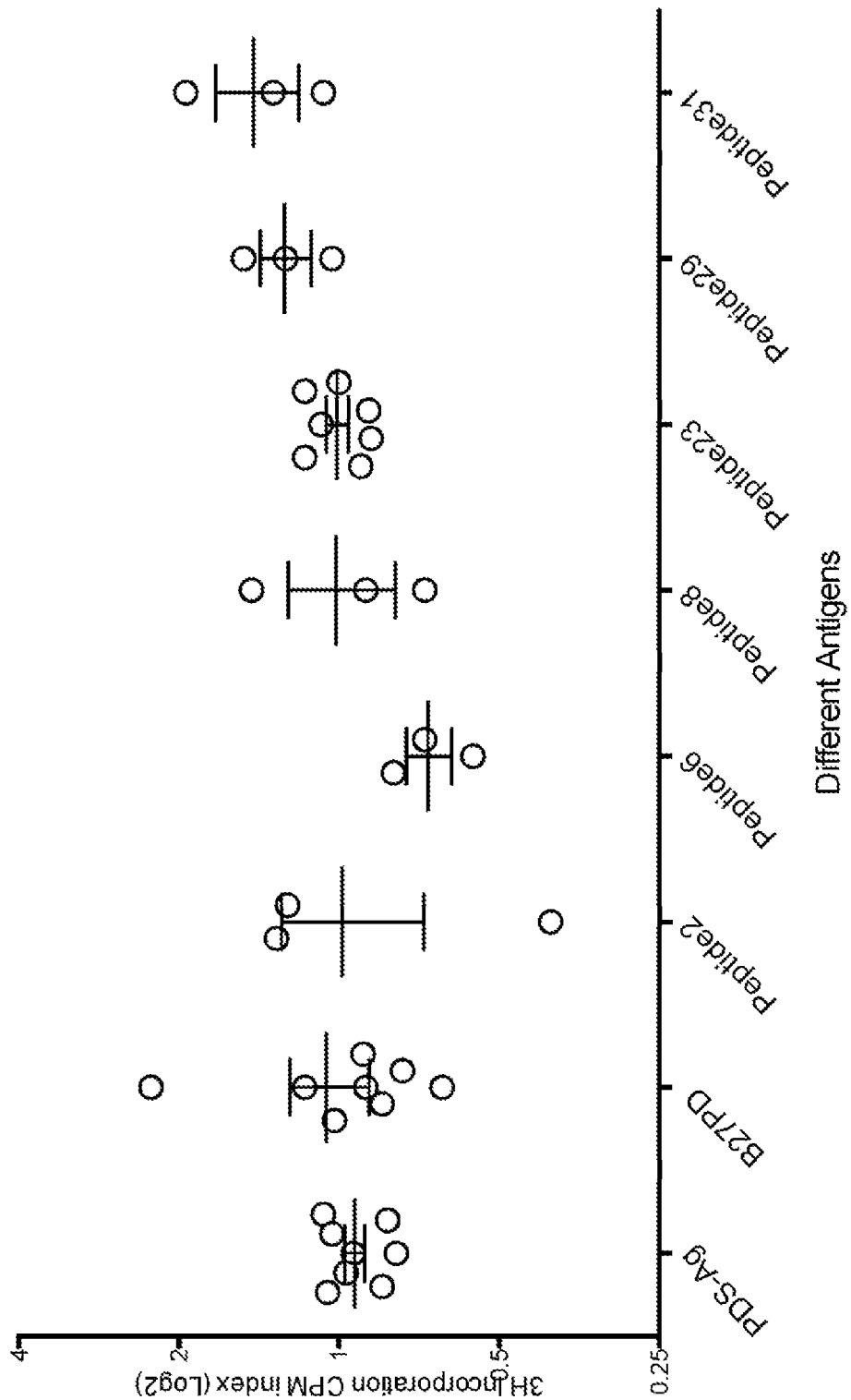
Figure 2B:
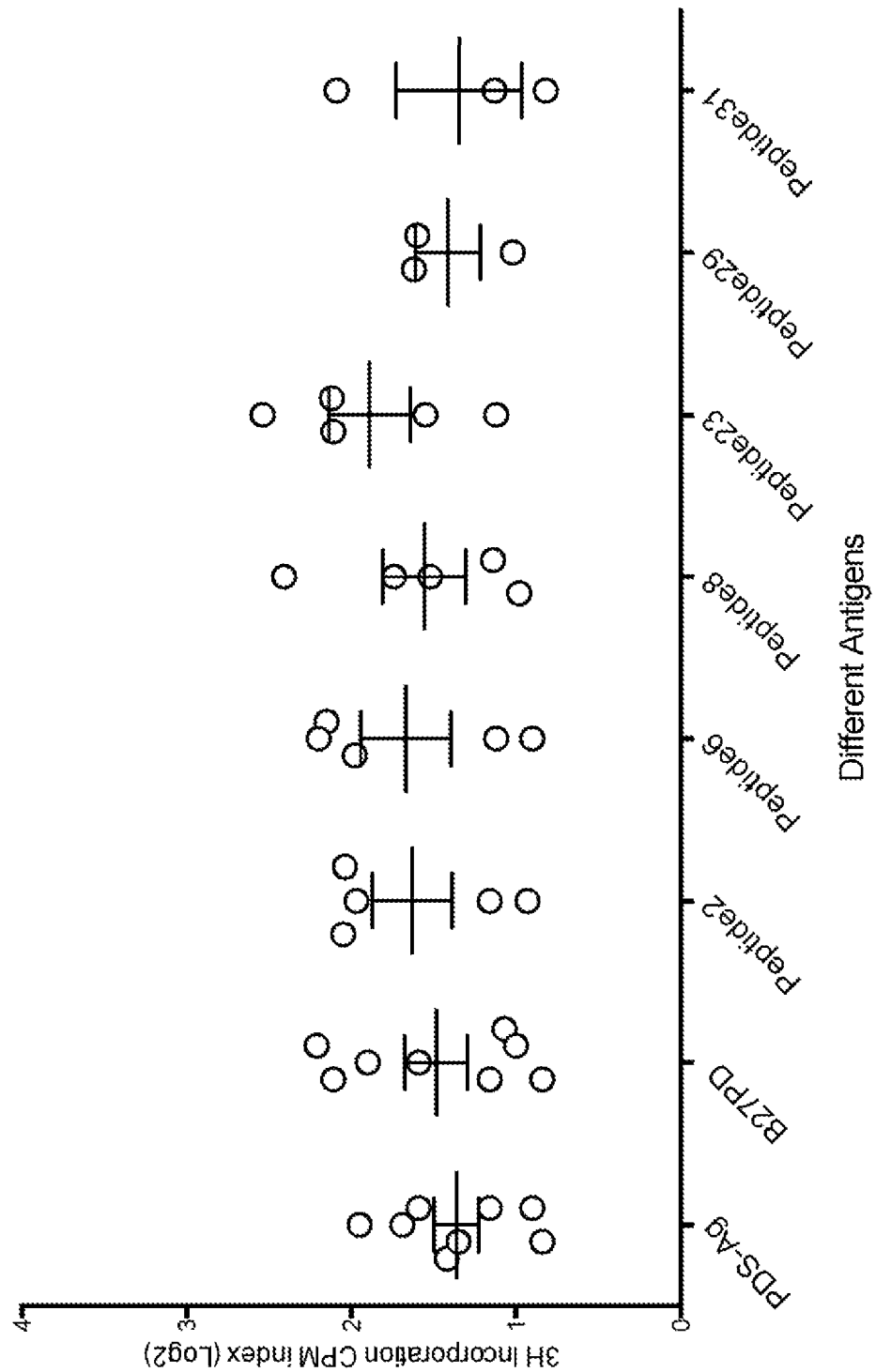
Figure 2C:
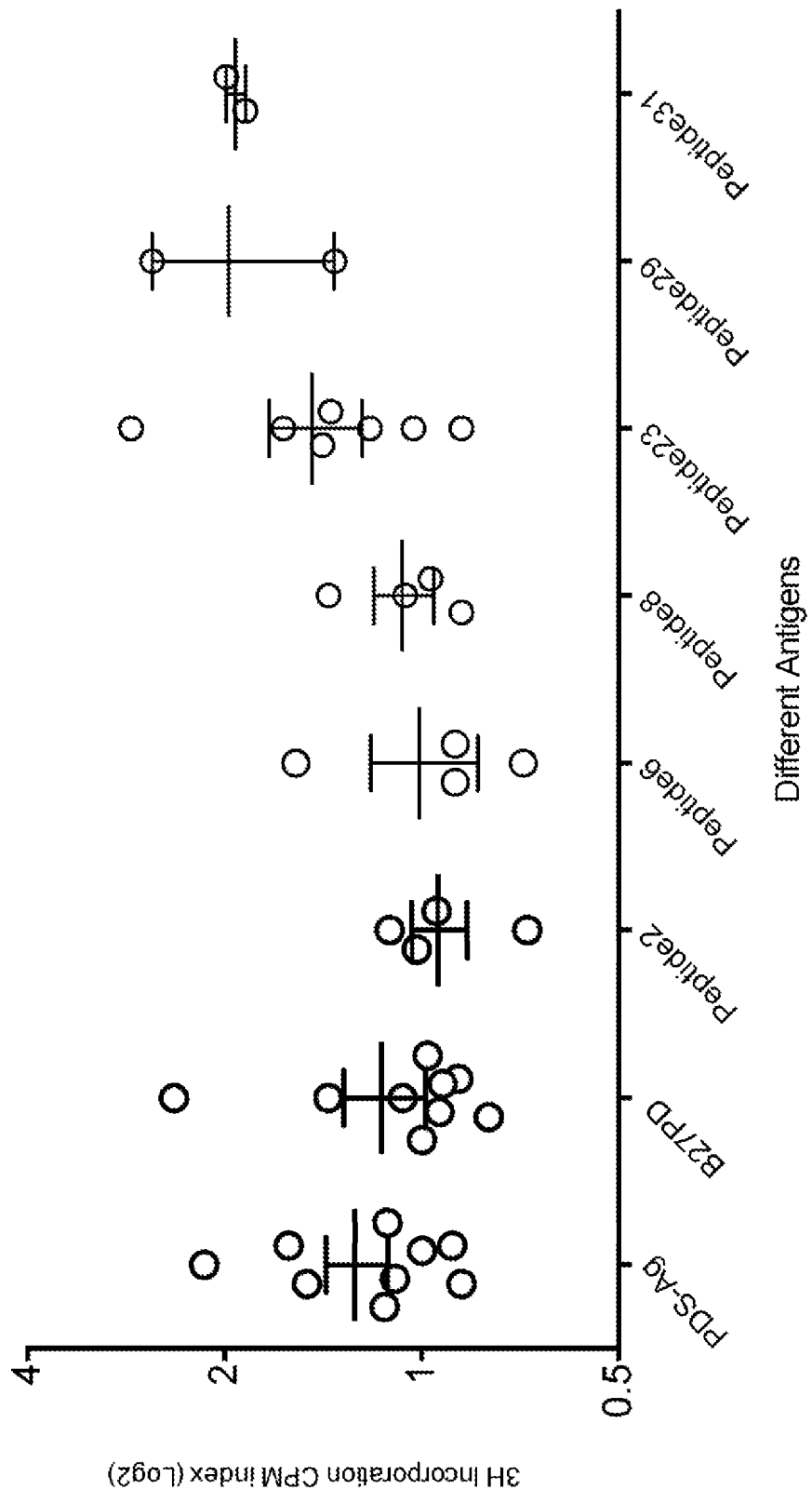
Figure 2D:
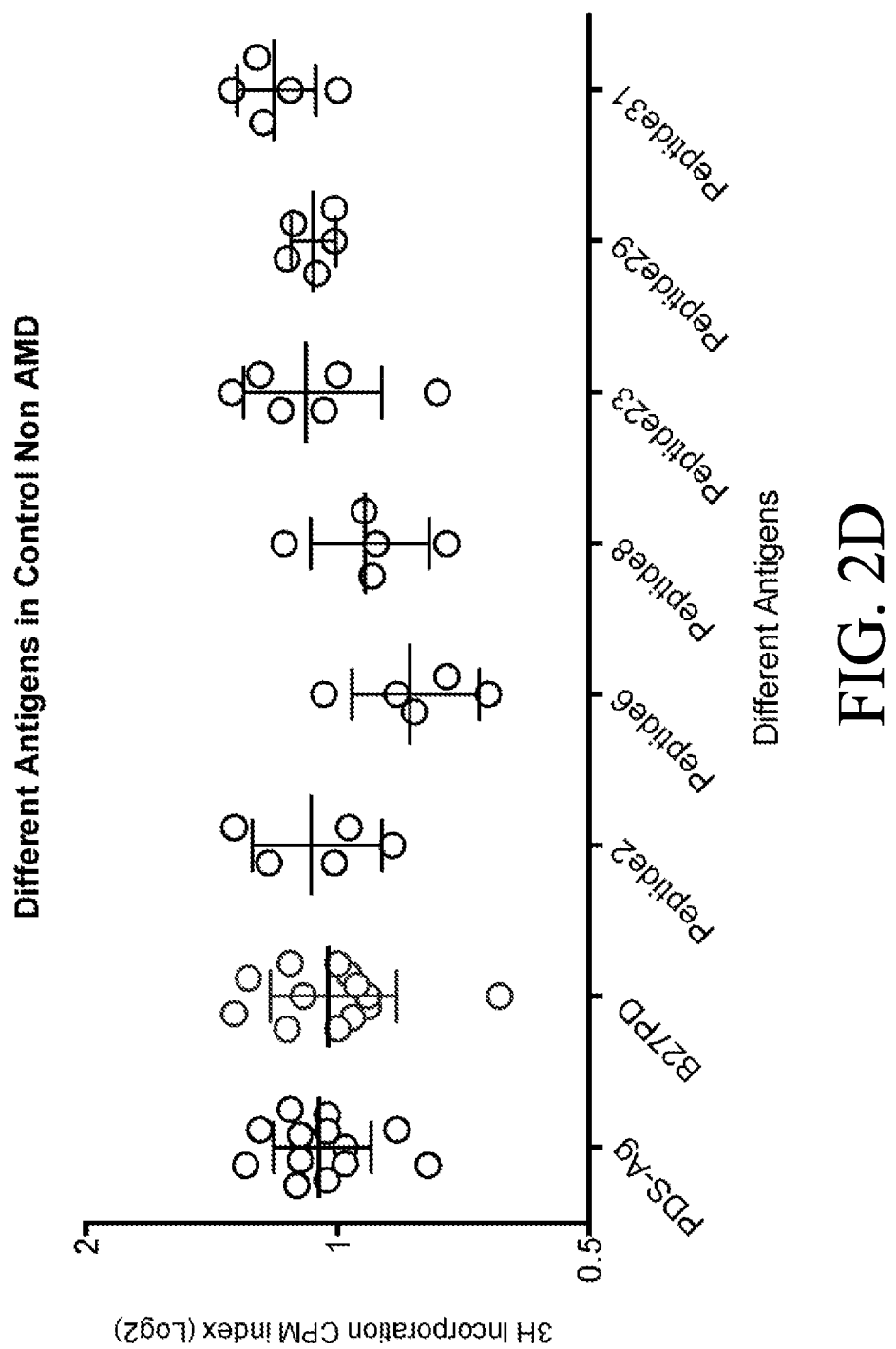

FIG. 2A shows the immunostimulatory activity of the various 15-mer peptide subsequences of human S-antigen on PBMCs from AMD patients with large drusen. FIG. 2B shows the immunostimulatory activity of the various 15-mer peptide subsequences of human S-antigen on PBMCs from AMD patients with medium drusen. FIG. 2C shows the immunostimulatory activity of the various 15-mer peptide subsequences of human S-antigen on PBMCs from early stage AMD patients with small drusen. FIG. 2D shows the immunostimulatory activity of the various 15-mer peptide subsequences of human S-antigen on PBMCs from control subjects without AMD.

Figure 3:
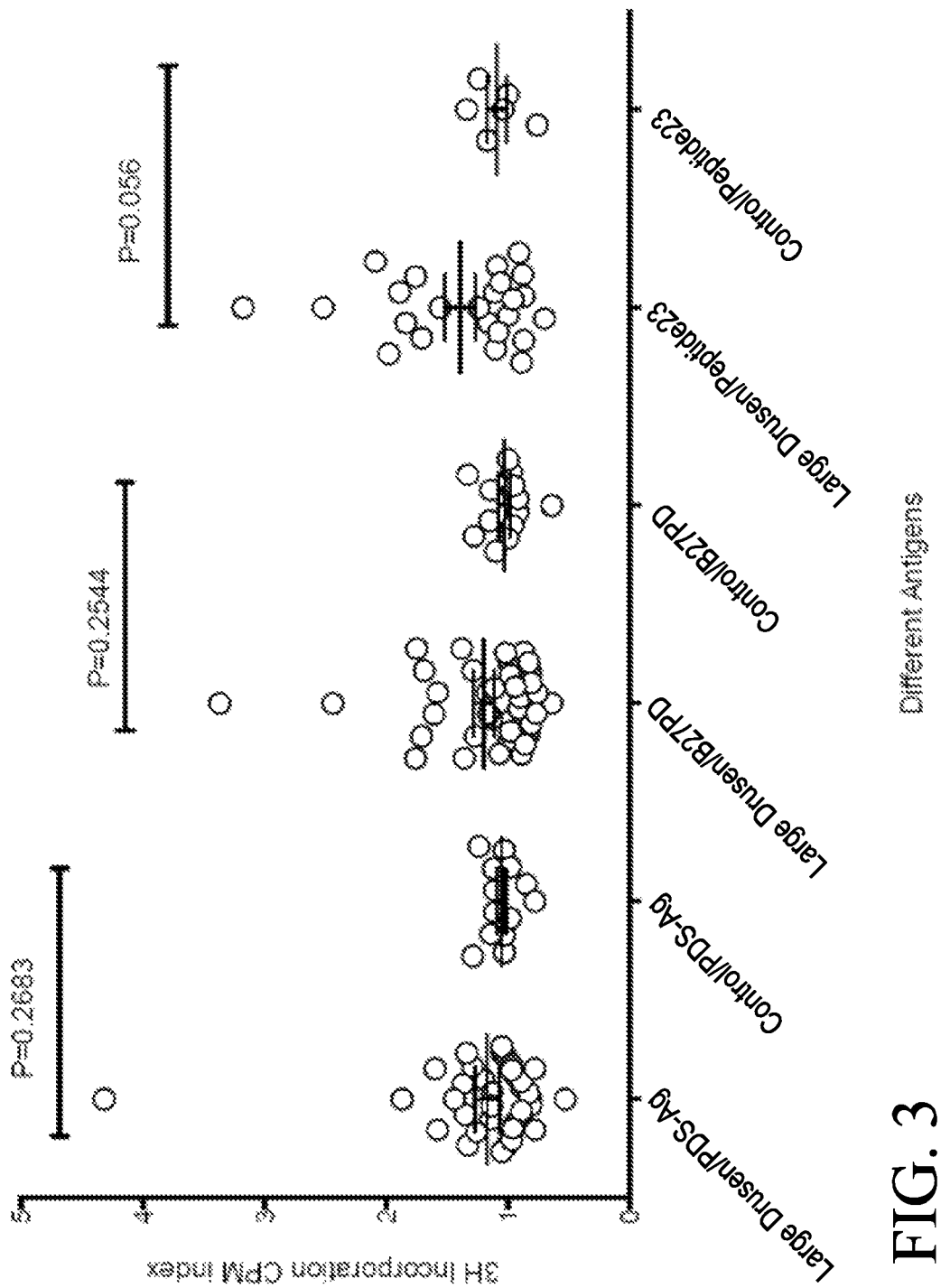

FIG. 3 shows the immunostimulatory activity of peptide PDS-Ag (SEQ ID NO: 10), peptide B27PD (SEQ ID NO: 4) and Peptide 23 (SEQ ID NO: 3) on PBMCs of AMD patients with large drusen and control subjects without AMD.

Figure 4:
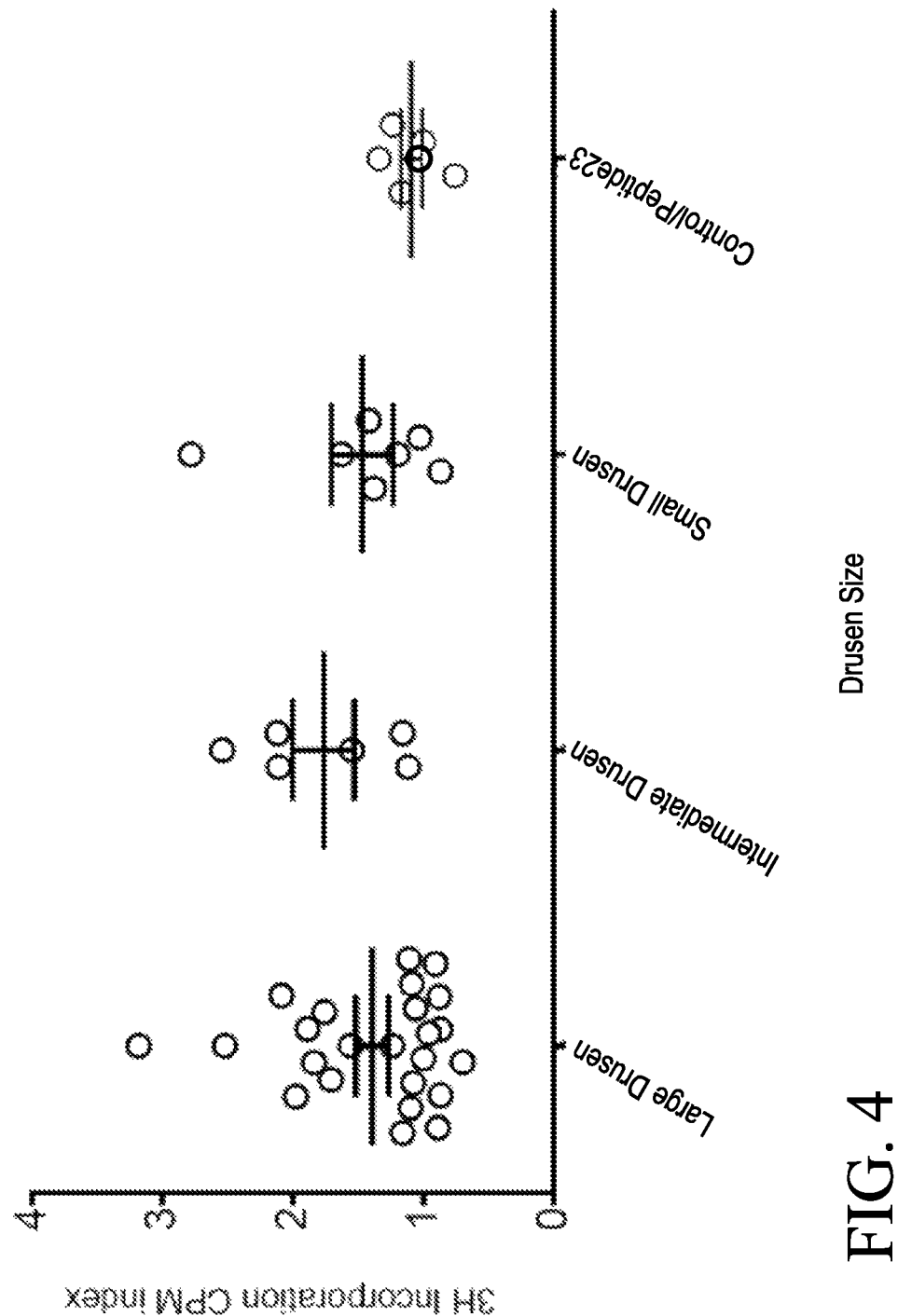

FIG. 4 provides the results of an experiment demonstrating the immunostimulatory activity of Peptide 23 (SEQ ID NO: 3) on PMBCs from AMD patients with large drusen, intermediate drusen and small drusen and from a control subject without AMD.

Figure 5:
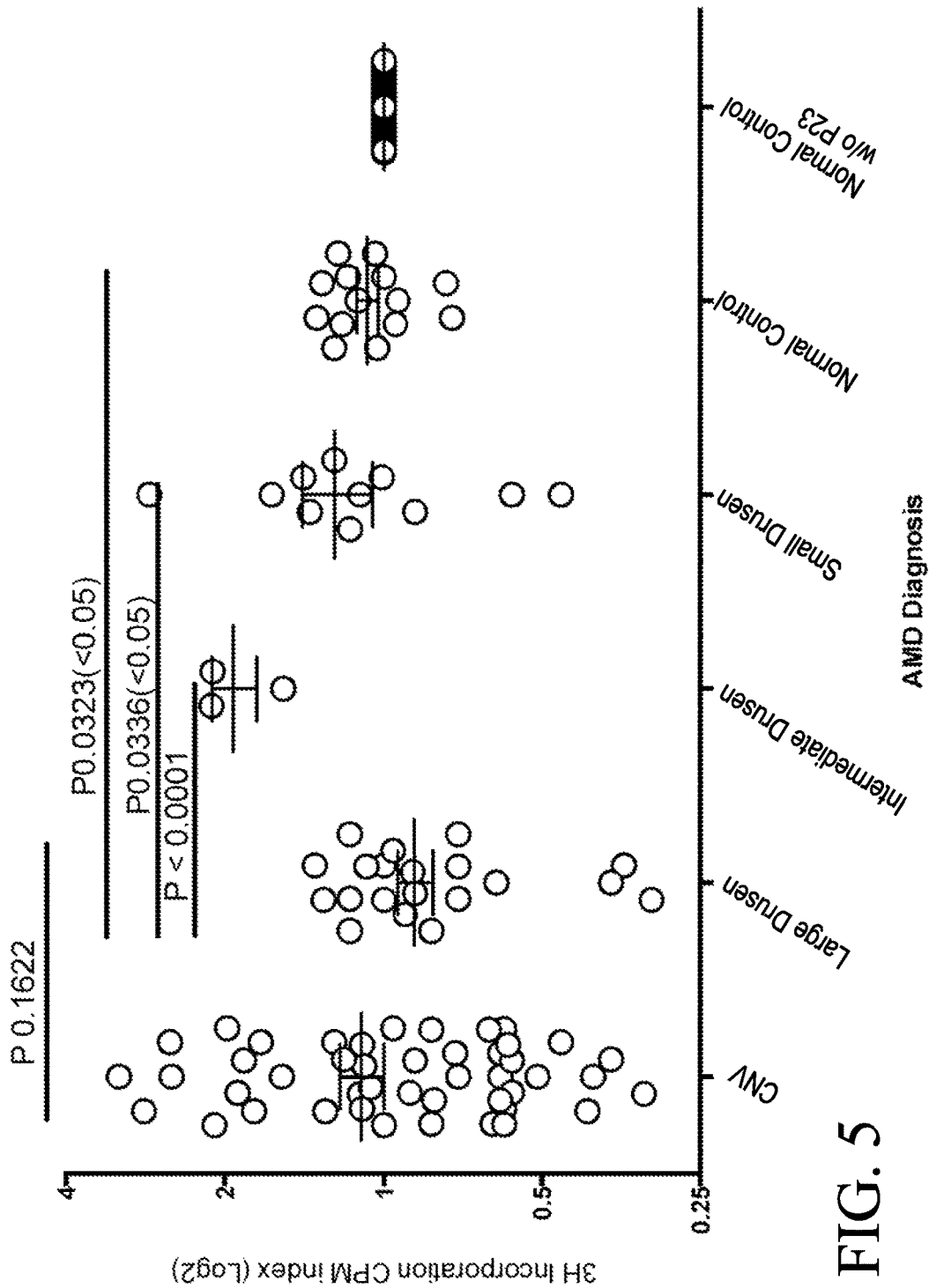

FIG. 5 provides the results of an experiment demonstrating immunostimulatory activity of Peptide 23 (SEQ ID NO: 3) on PMBCs from AMD patients at four different stages of disease and for two control cases.

7. DETAILED DESCRIPTION

In certain aspects, methods are presented for identifying a compound comprising an epitope that induces immune tolerance in a patient suffering from an autoimmune disease. In certain embodiments, the compounds are identified from a library or collection of compounds.

In other aspects, methods are provided for treating a patient suffering from an autoimmune disease. In various embodiments, the patient is treated by administering an effective amount of regulatory T-cells that have been trained in the presence of a compound comprising an epitope that induces immune tolerance, wherein the compound is identified by a method described herein. In other embodiments, the patient is treated by administering an effective amount of regulatory T-cells that are expanded, but have not been trained in the presence of a compound comprising an epitope that induces immune tolerance. In still other embodiments, the patient is treated by administering an effective amount of regulatory T-cells that have not been trained ex vivo. In some embodiments, the regulatory T-cells are trained in vivo upon administration of a compound comprising an epitope that induces immune tolerance, as identified by a method described herein. In particular embodiments, the patient is treated with a mixture of regulatory T-cells from a healthy individual and regulatory T-cells from the patient.

In yet other aspects, methods are provided for treating a patient suffering from an autoimmune disease by administering an effective amount of a compound identified as described herein, and an effective amount of regulatory T-cells. In certain embodiments, the regulatory T-cells are trained in the presence of a compound comprising an epitope that induces immune tolerance as identified by the methods described herein. In other embodiments, the compound that is used to train the regulatory T-cells is different from the compound that is administered to the patient in this combination therapy. In certain embodiments, the regulatory T-cells are expanded, but are not trained. In still other embodiments, the regulatory T-cells are trained after administration of the T-cells to the patient by administration of a compound identified by a method described herein. In some embodiments, the compound that is used to train the regulatory T-cells is the same compound that is administered to the patient.

As used herein, the term "patient" refers to humans and non-human animals such as non-human mammals. In some embodiments, the patient suffers from an autoimmune disease due to one or more factors described herein. In certain embodiments, the patient suffers from an autoimmune disease due to the presence of dysfunctional regulatory T-cells. As used herein, the term "dysfunctional" when referring to regulatory T-cells means that regulatory T-cell function in the patient is at least about 5%, at least about 10%, at least about 20%, at least about 30% or more lower than regulatory T-cell function in a healthy individual when comparing the same number of cells from the patient ant the healthy individual. In other embodiments, the patient suffers from an autoimmune disease due to the presence of lower numbers of regulatory T-cells as compared to numbers of regulatory T-cells in a healthy individual. In these embodiments, the patient has at least about 5%, at least about 10%, at least about 20%, at least about 30% or more fewer regulatory T-cells than a healthy individual when comparing the numbers of T-cells in the same volume of blood. In still other embodiments, the patient suffers from an autoimmune disease due to the presence of responder T-cells that are resistant to suppression by regulatory T-cells. In yet other embodiments, the patient suffers from an autoimmune disease due to the presence of higher numbers of responder T-cells than in a healthy individual. In these embodiments, the patient has at least about 5%, at least about 10%, at least about 20%, or at least about 30% or more responder T-cells than a healthy individual when comparing numbers of responder T-cells in the same volume of blood. In some embodiments, the patient suffers from an autoimmune disease as a result of a combination of factors. See e.g., Costantino et al. (2008) Eur. J. Immunol. 38(4):921-924; Baecher-Allan et al. (2004) Seminars in Immunol. 16:89-97.

The term "autoimmune disease" as used herein is any disease that arises from an inappropriate immune response of a patient's body against substances and tissues normally present in the body. In certain embodiments, the autoimmune disease is selected from acute disseminated encephalomyelitis, Addison's disease, agammaglobulinemia, age-related macular degeneration, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behcet's disease, Berger's disease, Bickerstaff's encephalitis, Blau syndrome, Bullous pemphigoid, cancer, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis, gastritis, gastrointestinal pemphigoid, glomerulonephritis, Goodpasture's syndrome, Graves' disease, Guillan-Barré syndrome, Hashimoto's encephalopathy, Hashimoto's thyroiditis, Henoch-Schonlein purpura, gestational pemphigoid, hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease, lupus erythematosus, Majeed syndrome, Meniere's disease, microscopic polyangiitis, mixed connective tissue disease, morphea, Mucha-Habermann disease, multiple sclerosis, myasthenia gravis, myositis, narcolepsy, neuromyelitis optica, neuromyotonia, occular cicatricial pemphigoid, opsoclonus myoclonus syndrome, Ord's thyroiditis, palindromic rheumatism, pediatric autoimmune neuropsychiatric disorders associated with streptococcus, paraneoplastic cerebellar degeneration, paroxysmal nocturnal hemoglobinuria, Parry Romberg syndrome, Parsonage-Turner syndrome, Pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome, Schnitzler syndrome, scleritis, scleroderma, serum sickness, Sjögren's syndrome, spondyloarthropathy, stiff person syndrome, subacute bacterial endocarditis, Susac's syndrome, Sweet's syndrome, sympathetic ophthalmia, Takayasu's arteritis, temporal arteritis, thrombocytopenia, Tolosa-Hunt syndrome, transverse myelitis, ulcerative colitis, undifferentiated connective tissue disease, urticarial vasculitis, vasculitis, vitiligo and Wegener's granulomatosis.

In particular embodiments, the autoimmune disease is selected from acute disseminated encephalomyelitis, age-related macular degeneration, alopecia areata, ankylosing spondylitis, antiphospholipid syndrome, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Behcet's disease, celiac disease, Chagas disease, chronic obstructive pulmonary disease, cold agglutinin disease, Crohn's disease, Dercum's disease, dermatomyositis, diabetes mellitus type 1, endometriosis, eosinophilic gastroenteritis, gastrointestinal pemphigoid, glomerulonephritis, Goodpasture's syndrome, Graves' disease, Guillan-Barré syndrome, Hashimoto's encephalopathy, Hashimoto's thyroiditis, hidradenitis suppurativa, idiopathic thrombocytopenic purpura, interstitial cystitis, Kawasaki's disease, lupus erythematosus, mixed connective tissues disease, morphea, multiple sclerosis, myasthenia gravis, narcolepsy, neuromyotonia, opsoclonus myoclonus syndrome, pediatric autoimmune neuropsychiatric disorders associated with streptococcus, paroxysmal nocturnal hemoglobinuria, pemphigus vulgaris, pernicious anaemia, polymyositis, primary biliary cirrhosis, progressive inflammatory neuropathy, psoriasis, psoriatic arthritis, Renaud phenomenon, relapsing polychondritis, restless leg syndrome, rheumatoid arthritis, rheumatic fever, sarcoidosis, schizophrenia, scleroderma, Sjögren's syndrome, stiff person syndrome, temporal arteritis, transverse myelitis, ulcerative colitis, undifferentiated connective tissue disease, vasculitis, vitiligo, and Wegener's granulomatosis.

As used herein, the term "about" means in a range of −5% to +5% of a recited numerical value.

In a particular embodiment, the autoimmune disease is an autoimmune disease of the eye. In certain embodiments, the autoimmune disease is selected from uveitis and age-related macular degeneration.

7.1. Methods of Identifying a Compound Comprising an Epitope that Induces Immune Tolerance As used herein, the term "compound comprising an epitope" includes a compound comprising a contiguous region of monomers that elicits immune tolerance in a patient suffering from an autoimmune disease. In certain embodiments, the compound comprises an epitope (e.g., the epitope is a subset of contiguous monomers of the compound). In other embodiments, the compound consists of the epitope (i.e., the entire compound is the epitope). In various embodiments, the epitope is a self-epitope of the patient. In other embodiments, the epitope is a non-self epitope. In certain embodiments, the epitope is organ specific. In other embodiments, the epitope is not organ specific. In various embodiments, the epitope is a human epitope. In other embodiments, the epitope is a non-human mammalian epitope. In still other embodiments, the epitope is a bacterial epitope or a viral epitope. In some embodiments, the epitope is a mixture of epitopes from different organisms.

It will be understood by the skilled artisan that, in addition to the epitope, in various embodiments, the compound includes one or more types of monomers, including but not limited to, naturally-occurring amino acids, non-naturally occurring amino acids, nucleotides, and the like. In certain embodiments, the epitope consists of amino acids, which can be naturally occurring or non-naturally occurring. In particular embodiments, the epitope consists of at least 3, such as at least 4, such as at least 5 or such as at least 6 or more amino acids. In certain embodiments, the compound can be a single compound or an aggregate of compounds (e.g., cross-linked compounds). In various embodiments, the compound can be unmodified or can be directly or indirectly (e.g., through a linking moiety) linked to another moiety, e.g., a sugar, a fat, a label (e.g., a fluorescent or radioactive label) or an additional therapeutic agent.

In various embodiments, the compound comprising an epitope that induces immune tolerance in a patient is identified from a library or collection of compounds. In some embodiments, the library is a library of biological epitopes. Accordingly, in certain embodiments, the library is a library of organ specific epitopes. In these embodiments, the epitopes are restricted to a particular organ of the body, e.g., the eye. Thus, in a particular embodiment, the library of organ specific epitopes is a library of S-antigen epitopes, such as human S-antigen epitopes. Reported amino acid sequences of human S-antigen are set forth as SEQ ID NO: 1 and SEQ ID NO: 11 in the accompanying Sequence Listing. In other embodiments, the library is a library of epitopes that are not organ specific, e.g., that are found throughout the body. An example of this embodiment is a library of HLA epitopes, such as a library of variant HLA epitopes (e.g., a library of HLA-B27 epitopes). In some embodiments, the library can be a library of epitopes from the patient (a library of self epitopes) or a library of epitopes that are not from the patient (a library of non-self epitopes).

In a particular embodiment, the library is a library of peptides. In certain embodiments, the library comprises synthetic peptides. In some embodiments, peptides are synthesized with a given length and a predetermined overlapping sequence so that the library encompasses a particular protein. See, e.g., Gershoni et al. (2007) BioDrugs 21 (3): 145-56. In other embodiments, peptide libraries are created using mass spectrometry, such as by Solid Phase Epitope Recovery (SPHERE). See Lawendowski et al. (2002) J. Immunol. 169:2414-21. In certain embodiments, a library for use in the methods described herein includes, but is not limited, to a phage display library, a bacterial or yeast display library, an mRNA display library, a ribosomal display library, a polysomal display library or a peptide matrix. See e.g., U.S. Patent Publication No. 2013/0004513 (Osterroth et al.).

In other embodiments, the compound comprising an epitope that induces immune tolerance in a patient is identified from a collection of compounds. In these embodiments, combinatorial epitope collections may be utilized. Accordingly, in certain embodiments, the collection comprises all permutations of a polymeric compound having a preselected number of monomers "n" which may, for example, be a whole number in the range of 4-100 or in any sub-range therein such as 4-40 monomers or any whole number therein, such as 4, 5, 6, 7, 8, 9, 10 and so on up to and including 100. In certain embodiments, the compound is a peptide and the collection comprises all permutations of a peptide with all 20 amino acids (or a subset thereof) at each position such that the collection includes $20^n$ different n-mer peptides, such as but not limited to $20^4$ tetramers where n=4 and $20^5$ pentamers where n=5. Peptide sequences are recited herein in accordance with convention, left to right from amino terminus to carboxy terminus unless otherwise noted.

In various embodiments, the in vitro methods for identifying a compound comprising an epitope that induces immune tolerance in a patient suffering from an autoimmune disease comprise measuring responses of responder T-cells and regulatory T-cells from the patient and measuring responses of responder T-cells and regulatory T-cells from a healthy individual and comparing the various responses from the T-cells of the patient with responses from the T-cells of a healthy individual. As used herein, a "healthy individual" is an individual who does not suffer from an autoimmune disease.

As used herein, a "responder immune cell" or "responder cell" refers to cells of the immune system that mount an immune response to antigens, such as antigens presented on antigen presenting cells (e.g., antigens associated with a pathogen or tumor cell-specific antigen) and/or, in the context of autoimmunity, mount a response or over response to self-antigens. As used herein, "responder T-cell" or "T-resp" refers to responder immune cells that are T-cells which mount an immune response to antigens and, in the context of autoimmunity, to self-antigens. Thus, responder T-cells or T-resp cells as described herein are a subset of responder immune cells as described herein. T-resp cells can be polyclonal or antigen-specific. Responder immune cells include, for example, T-cells with certain phenotypes, including, but not limited to, $CD8^+$ T-cells, $CD8^+$ effector T-cells, $CD4^+$ T-cells, $CD4^+$ effector T-cells, $CD4^+CD25^-$ T-cells, naïve $CD4^+CD25^-$ T-cells, cytotoxic T lymphocytes (CTL), as well as NK cells and mature dendritic cells (DC).

As used herein, a "regulatory immune cell" or "regulatory cell" refers to immune cells, such as T-cells, that suppress an immune response of immune responder cells. As used herein, a "regulatory T-cell" or "T-reg" refers to T-cells that suppress an immune response of T-resp cells. In certain embodiments, T-reg cells have an anergic phenotype, i.e., they do not proliferate in response to T-cell receptor stimulation. Regulatory immune cells or regulatory cells as described herein are a subset of regulatory T-cells or T-reg cells as described herein. Regulatory immune cells include, for example, T cells with particular phenotypes, including, but not limited to $CD4^+CD25^+$ T-cells, $CD4^+Foxp3^+$ T-cells, $CD4^+CD25^+Foxp3^+$ T-cells, IL-10 producing $CD4^+$ Tr1 cells, TGF-β producing Th3 cells, $CD8^+$ NKT cells, $CD4^-CD8^-$ T-cells, γδ T-cells, thymic nT-reg cells, periphery induced i-Treg cells, $CD4^+CD127^{lo/-}$ T-cells, $CD4^+CD127^{lo/-}CD25^+$ T-cells, the $CD45RA^+$ subset of $CD4^+CD127^{lo/-}CD25^+$ T-cells as well as tolerogenic dendritic cells (DC). In various embodiments, T-reg cells are negative for CD127 and positive for CD39. In other embodiments, T-reg cells are induced from $CD4^+CD25^-$ cells by stimulation with irradiated allogenic stimulator PMBCs. In some embodiments, the T-reg cells inhibit polyclonal T-resp cells. In other embodiments, T-reg cells inhibit antigen-specific T-resp cells.

Throughout this disclosure, various aspects and embodiments of the invention, and variations thereof, are described with respect to particular types of responder immune cells and regulatory immune cells or with respect to responder immune cells and regulatory immune cells generally. Where such descriptions are made with respect to particular types of responder immune cells and/or regulatory immune cells it should be understood that the invention also provides corresponding embodiments and variations thereof for the other particular types of responder immune cells and/or regulatory immune cells and for responder immune cells and/or regulatory immune cells generally. Likewise, where such descriptions are made with respect to responder immune cells and/or regulatory immune cells generally, it should be understood that the invention also provides corresponding embodiments and variations thereof for the particular types of responder immune cells and/or regulatory immune cells.

The skilled artisan will recognize that new phenotypes of T-reg cells and T-resp cells may be discovered. Accordingly, the present disclosure encompasses not only T-reg and T-resp cell phenotypes described above, but also any T-cell having the regulatory/suppressor or responder characteristics of T-reg cells or T-resp cells, whether identified herein or yet to be characterized.

Accordingly, in various aspects, the present disclosure relates to methods of identifying a compound comprising an epitope that induces immune tolerance in a human patient suffering from an autoimmune disease comprising the step of identifying in vitro a compound from a library or collection of compounds that (i) elicits a response (RespH) from a responder T-cell of a healthy individual, (ii) elicits a response (RespP) from a responder T-cell of the patient, (iii) elicits a response (RegH) from a regulatory T-cell of a healthy individual and (iv) elicits a response (RegP) from a regulatory T-cell of the patient, wherein the compound that induces a RespH/RespP<1, a RegH/RegP≥1 or a RespH/RespP<1 and a RegH/RegP≥1 is the compound that induces immune tolerance in the patient. In certain embodiments, the compound induces a RespH/RespP<1. In some embodiments, the compound is identified by a RespP that is greater than the RespH. In other embodiments, the compound is identified by a RegH that is greater than the RegP. In still other embodiments, the compound is identified by a RespP that is greater than the Resp H and by a RegH that is greater than the RegP.

In another embodiment, the invention provides a method of identifying a compound comprising an epitope that induces immune tolerance in a patient suffering from an autoimmune disease comprising the step of (a) identifying in vitro a compound from a library or collection of compounds that (i) elicits a response ($RespP_1$) from a responder T-cell of the patient; (ii) elicits a response (RespH) from a responder T-cell of a healthy individual wherein $RespP_1/RespH>1$; and (iii) elicits a response ($RespP_2$) from a responder T-cell of the patient in the presence of a responder T-cell antigen and a regulatory T-cell, wherein $RespP_2/RespP_1<1$, and wherein the compound that induces a $RespP_1/RespH>1$ and $RespP_2/RespP_1<1$ is identified as the compound that induces an immune tolerance.

In some embodiments, the compound is identified by a $RespP_1$ that is greater than the RespH and by a $RespP_1$ that is greater than the $RespP_2$.

In yet another embodiment, the invention provides a method of identifying a compound comprising an epitope from a library or collection of compounds that induces immune tolerance in a human patient suffering from an autoimmune disease, comprising (i) exposing a human $CD4^+CD25^+$ cell to a compound, (ii) measuring the proliferation ($Reg_1$) of human $CD4^+CD25^+$ cells in the presence of the compound, and (iii) measuring the proliferation ($Reg_2$) of the human $CD4^+CD25^+$ cells in the absence of the compound, wherein the compound that induces $Reg_1/Reg_2>1$ is identified as the compound that induces immune tolerance in the patient. In a particular embodiment, step (ii) is performed after the compound is removed. In certain embodiments the compound that induces $Reg_1/Reg_2>1$. In various embodiments, the cell proliferation in the presence of the compound is greater than the cell proliferation in the absence of the compound.

In some embodiments, the T-reg cells are induced, e.g., from naïve cells, before step (i). In certain embodiments of this method, the $CD4^+CD25^+$ cells are isolated before being exposed to a compound. In some embodiments, cells are isolated using commercially available isolation kits, such as magnetic bead isolation using antibodies that specifically bind to CD4 and/or CD25 and/or other cell surface markers. In certain embodiments, kits using positive or a combination of negative and positive selection are used. In various embodiments, the identification of specific T-cell phenotypes is carried out using flow cytometry. In a particular embodiment, identification and/or separation is accomplished by FACs. In various embodiments, the $CD4^+CD25^+$ cells are from a healthy individual.

In yet another embodiment, the present disclosure relates to a method of identifying a compound comprising an epitope that induces immune tolerance in a patient suffering from an autoimmune disease, comprising identifying in vitro a compound from a library or collection of compounds that (i) elicits a response (RespH) from a T-resp of a healthy individual, and (ii) elicits a response (RespP) from a T-resp of the patient, wherein the compound that induces a RespH/RespP<1 is identified as the compound that induces immune tolerance in the patient. In some embodiments, the compound induces a RespH/RespP<1.

In certain embodiments, the response of the responder T-cell of the patient in the presence of the compound is greater than the response of the responder T-cell of the healthy individual in the presence of the compound.

In various embodiments, the present disclosure relates to a method of identifying a compound comprising an epitope that induces immune tolerance in a human patient suffering from an autoimmune disease using a mixed-cell assay. As used herein, the term "mixed-cell assay" refers to an assay that includes both (i) responsive T-cells and (ii) regulatory T-cells. Thus, in certain embodiments, the method of identifying a compound comprises a step of identifying in vitro a compound that elicits a response (Presp) from a responder T-cell of a patient in the presence of regulatory T-cells of the patient that is greater than the response (Preg) elicited from the regulatory T-cells of the patient in the assay. In certain embodiments the Presp/Preg>1. In other embodiments, the method comprises a step of identifying in vitro a compound that elicits a response (Hreg) from regulatory T-cells of a healthy individual in the presence of responder T-cells of the patient that is greater than the response (Presp) elicited from the responder T-cells of the patient in the assay. In some embodiments, Hreg/Presp>1. In still other embodiments, the method comprises a step of identifying in vitro a compound that elicits a response (Hresp) from responder T-cells from a healthy individual in the presence of regulatory T-cells from the patient that is greater than the response (Preg) from the regulatory T-cells of the patient in the assay. In certain embodiments, Hresp>Preg. In still other embodiments, the method comprises a step of identifying in vitro a compound that elicits a response (Hresp) from responder T-cells from a healthy individual in the presence of regulatory T-cells from the healthy individual that is less than the response (Hreg) elicited from the regulatory T-cells of the healthy individual in the assay. In some embodiments, Hresp<Hreg. It will be evident to the skilled artisan that more than one of the mixed-cell assays can be performed in order to identify a compound comprising an epitope that induces immune tolerance in a human patient suffering from an autoimmune disease.

As used herein, a "response" from at T-reg cell or a T-resp cell is an indication that a T-cell is upregulated, e.g., in response to contact with a substance such as a naturally occurring or synthetic biomolecule, for example, a synthetic peptide. In various embodiments, the response includes, but is not limited to, one or more of upregulation of cell-surface markers, such as activation markers, cytokine synthesis and/or secretion, and cell proliferation (expansion). A T-cell response can be measured by any method known in the art. In particular embodiments, a T-cell response is measured by T-cell proliferation. In these embodiments, T-cell proliferation is measured by cell counting, e.g., using flow cytometry, and in particular, fluorescence-activated cell sorting (FACs) based on the T-cell markers. In other embodiments, T-cell proliferation can be measured by [$^3$H]-thymidine uptake. See, e.g., Wallace et al. (2008) Cytometry A 73(11):1019-34. In certain embodiments, T-cell proliferation can be measured using cell tracking dyes to label T-resp cells and monitor decreases in fluorescence associated with cell division. In some embodiments in which a mixed-cell assay is used, T-reg cells and T-resp cells can be independently labeled with two readily distinguishable dyes in order to discriminate each T-cell population in co-cultures. See Brusko et al. (2007) Immunol. Investigations 36:607-628. See, e.g., Venken et al. (2007) J. Immunol. Methods 322:1-11. In still other embodiments, the activity of T-cells can be assayed by cytokine secretion, which can be detected, e.g., by an ELIspot assay. In still other embodiments, activated T-cells can be assayed by detection of intracellular cytokine production by intracytoplasmic cytokine staining. Other assay formats for measuring T-cell responses will be known to the skilled artisan. See, e.g., LiPira et al. (2010) J. Biomedicine and Biotechnol. 1-12. See, e.g., Kruisbeek et al. Current Protocols in Immunology 3.12.1-3.12.20 (John Wiley & Sons, Inc., 2004).

Immune cells, such as regulatory immune cells or responder immune cells (either of which may, for example, be T-cells), may be "trained" by contacting the cells in in vitro culture with a preselected substance, such as a synthetic peptide, over a period of time. Cultured cells that respond to the substance preferentially proliferate in the culture versus other cells and upregulate cell-surface markers, such as activation markers, cytokine synthesis and/or secretion of cytokines. The resulting population of cultured cells is said to be "trained" with the substance because it contains a larger fraction of immune cells that respond to the substance and/or are activated to respond to the substance than is present in the population of immune cells as obtained from the subject or present in the culture before being contacted with the substance. Such trained immune cells may be administered to a mammalian subject such as a human subject (the same subject from which the immune cells were originally obtained or a different individual) as a therapeutic treatment as described further herein.

In various embodiments, the in vitro assays described herein are carried out in the absence of antigen presenting cells. In other embodiments, the assays are performed in the presence of antigen presenting cells, such as murine antigen presenting cells or irradiated human PMBCs. In still other embodiments, T-reg cells and/or T-resp cells are labeled, e.g., by radioisotopes or fluorescent dyes. In various embodiments, the assays are performed in the presence of cytokines. Various types of in vitro T-cell assays for determining the activity of T-reg and T-resp cells will be known to the skilled artisan. See, e.g., Collison and Vignali (2011) Methods Mol. Biol. 707:21-37.

The nature of T-reg cells in autoimmune diseases has been found to be variable. For example, Yeh et al., 2009 (Arch Opthamology 127; 407-413) found that there was a significant difference in numbers of T-reg cells between uveitis patients with active disease (4.3%) and uveitis patients with inactive disease (6.2%). Ursaciuc et al. 2010 (Romanian Arch Microbiol Immunol 69; 79-84) found a reduced presence of T-reg cells in systemic autoimmune diseases (SAID) compared to rheumatoid arthritis (RA) and controls and even concluded that T-reg percentage was the only cellular criterion of SAID evaluation. On the other hand, increased numbers of T-reg cells have also been found in autoimmune diseases such as juvenile arthritis (Cao et al., 2003 Eur J Immunol 33; 215-233). Lastly, there are reports that the defect lies not in the number of T-reg cells but in a disruption of their suppressive capability found in studies of multiple sclerosis (Viglietta et al., 2004 J Exp. Med. 199; 971-979), psoriasis (Sugiyama et al., 2005 J. Immunol. 174; 164-173) and myasthenia gravis (Baladina et al., 2003 Am NY Acad Sci 998; 275-277). As such, certain embodiments of the present invention measure the ability of a compound to be used in a suppressive assay with T-reg cells derived from diseased and healthy donors, where the number of total T-cells needed to provide a sufficient level of T-reg derived suppression of T-resp cells activity can be compared for a fixed level of inhibition. Thus, an antigen linked to a defect in either numbers or quality of T-reg cells in patients with autoimmune conditions will be recognized by these means since a ratio of the total number of T-cells from diseased and normal donors should be the same if the number and quality of T-reg cells are the same in both sources, whereas the number of T-cells used to achieve the fixed level will be greater to compensate for a loss of suppressive capability due to either a defect in the number or quality of T-reg cells in a patient sample. Accordingly, in various embodiments, the measured response of T-cells is normalized. In some embodiments in which the patient has fewer T-reg cells than a healthy individual in the same volume of blood, the responder and/or regulatory T-cell response is normalized by the steps of (i) determining the total number of T-cells (all types) ("P1") from a healthy donor that provides an amount of T-reg cells that induces 50% suppression of the T-resp response; (ii) determining the total number of T-cells (all types) ("P2") from the donor suffering from an autoimmune disease that provides an amount of T-reg cells that induces suppression of 50% of the T-resp response; and (iii) calculating P1/P2 to determine the amount of T-reg cells that are lacking in the donor suffering from an autoimmune disease. A ratio of P1/P2 that is greater than 1 is an indication that the compound may have therapeutic value as a tolerogenic agent or an agent for inducing or expanding T-reg cells that recognize the compound.

Thus, in some embodiments, the invention provides a method of identifying a compound comprising an epitope that induces immune tolerance in a human patient suffering from an autoimmune disease comprising the steps of (a) identifying in vitro a compound from a library or collection of compounds that (i) elicits a response (RespH) from responder T-cells of a healthy individual; and (ii) elicits a response (RespP) from responder T-cells of the patient; (b) determining the total number of T-cells (P1) from the healthy individual that provides an amount of T-reg cells that induces 50% suppression of T-resp activity in the presence of said compound; and (c) determining the total number of T-cells (P2) from the patient that provides an amount of T-reg cells that induces 50% suppression of said T-resp activity in the presence of said compound, wherein the compound that induces a RespH/RespP<1, a P1/P2>1 or RespH/RespP<1 and a P1/P2>1 is identified as the compound that induces immune tolerance in the patient.

In other embodiments, the screening methods identify an epitope from a library of biological epitopes for treating age-related macular degeneration. In various embodiments, the compound is a peptide. In some embodiments, the peptide is from S-antigen, e.g., a fragment of S-antigen. In one embodiment, the peptide has the sequence GEPIPVTVDVTNNTEKTVKK (SEQ ID NO: 2). In another embodiment, the peptide has the sequence VTVDVTNNTEKTVKK (SEQ ID NO: 3; "Peptide 23" or "P23"). Accordingly, the present disclosure also provides methods for treating a patient suffering from an autoimmune disease of the eye. In certain embodiments, the autoimmune disease is selected from uveitis and age-related macular degeneration. "Age-related macular degeneration" or "AMD" as used herein encompasses all forms of the disease, including dry AMD and wet AMD, and disease at any stage, such as, for example, dry AMD in patients with small, intermediate or large drusen volumes.

In some embodiments, an assay described herein is performed in the presence of one or more additional agents. In certain embodiments, an assay described herein is performed in the presence of one or more immune tolerance enhancer. As used herein, an "enhancer" is any compound or mixture of compounds that potentiates the immune suppressive response of T-reg cells. In certain embodiments, the enhancer is required for T-reg cell expansion. In some embodiments, the enhancer is used in the in vitro methods described herein. In other embodiments, the enhancer is used in in vivo methods described herein. In still other embodiments, the enhancer is used in both in vitro assays and in vivo methods. In some embodiments, the enhancer is high molecular weight hyaluronic acid. As used herein, the term "high molecular weight hyaluronic acid" refers to hyaluronic acid having a molecular weight of at least about $1 \times 10^6$ Da, such as of at least about $2 \times 10^6$ Da, at least about $3 \times 10^6$ Da, at least about $4 \times 10^6$ Da, or more. See e.g., Bollyky et al. (2007) J. Immunol. 179:744-747. The one or more enhancers may include, but are not limited to, high molecular weight hyaluronic acid, IL-2, IL-15, TGF-β, all-trans retinoic acid, rapamycin, anti-CD3, anti-CD28, vitamin D3, dexamethasone, IL-10, idolamine-2,3-dioxygenase, FTY720, a sphingosine kinase 1 inhibitor, cholera toxin B subunit, ovalbumin, Flt2L, sirolimus and/or anti-thymocyte globulin, CTLA-4/Ig, and mixtures thereof. See, e.g., Viney et al. (1998) J. Immunol. 160(12):5815-25; Horwitz et al. (2004) Seminars in Immunol. 16:135-143; Daniel et al. (2007) J. Immunol. 178(2): 458-68; Weiner et al. (2011) Immunol Rev. 241(1):241-259; Ma et al. (2011) Int. Immunopharmacol. 11(5):618-29; Adriouch et al. (2011) Front. Microbiol. 2:199; Dons et al. (2012) Human Immunol. 73:328-334. The one or more enhancers may include a sphingosine kinase 1 inhibitor as disclosed in U.S. Pat. No. 8,872,888, which is incorporated by reference herein in its entirety.

In some embodiments, the compound identified by a method described above is used as a reference sequence to search a library for additional compounds, which have homology to the reference sequence. In certain embodiments, the reference sequence is the entire protein target sequence. In various embodiments, the reference sequence and identified compounds are compared using a comparison window, a contiguous specific segment of the polypeptide sequence, which can have gaps compared to the reference sequence, for optimal alignment of peptides. In certain embodiments, the comparison sequence is at least about 10 amino acids, at least about 15 amino acids, at least about 20 amino acids, or at least about 25 or more amino acids. Tools for aligning sequences for comparison are well known in the art and include, but are not limited to, CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). In certain embodiments, compounds are chosen that at least about 30%, such as at least about 35%, at least about 40%, at least about 45%, at least about 50%, at least about 55%, at least about 60%, at least about 65%, at least about 70%, at least about 75%, at least about 80%, at least about 85%, or at least about 90% or more homology or identity to the reference sequence. The identified compound can then be assayed by a method described herein.

Accordingly, in some embodiments, the present disclosure relates to methods of identifying a compound comprising an epitope that induces immune tolerance in a human patient suffering from an autoimmune disease comprising the steps of: (a) identifying in vitro a compound from a library or collection of compounds that (i) elicits a response (RespH) from a responder T-cell of a healthy individual, (ii) elicits a response (RespP) from a responder T-cell of the patient, (iii) elicits a response (RegH) from a regulatory T-cell of a healthy individual and (iv) elicits a response (RegP) from a regulatory T-cell of the patient, wherein the compound that induces a RespH/RespP<1, a RegH/RegP≥1 or a RespH/RespP<1 and a RegH/RegP≥1 is the compound that induces immune tolerance in the patient; (b) using the compound identified in step (a) as a reference sequence to search a library or collection of compounds for one or more compounds having homology to the reference sequence; (c) identifying one or more compounds having homology to the reference sequence; and (d) repeating step (a) with the one or more compounds identified in step (c).

In another embodiment, the invention provides a method of identifying a compound comprising an epitope that induces immune tolerance in a patient suffering from an autoimmune disease comprising the steps of (a) identifying in vitro a compound from a library or collection of compounds that (i) elicits a response ($RespP_1$) from a responder T-cell of the patient; (ii) elicits a response (RespH) from a responder T-cell of a healthy individual wherein $RespP_1$/RespH>1; and (iii) elicits a response ($RespP_2$) from a responder T-cell of the patient in the presence of a responder T-cell antigen and a regulatory T-cell, wherein $RespP_2$/$RespP_1$<1, and wherein the compound that induces a $RespP_1$/RespH>1 and $RespP_2$/$RespP_1$<1 is identified as the compound that induces an immune tolerance; (b) using the compound identified in step (a) as a reference sequence to search a library or collection of compounds for one or more compounds having homology to the reference sequence; (c) identifying one or more compounds having homology to the reference sequence; and (d) repeating step (a) with the one or more compounds identified in step (c).

In yet another embodiment, the invention provides a method of identifying a compound comprising an epitope from a library or collection of compounds that induces immune tolerance in a human patient suffering from an autoimmune disease, comprising (i) exposing a human $CD4^+CD25^+$ cell to a compound, (ii) measuring the proliferation ($Reg_1$) of human $CD4^+CD25^+$ cells in the presence of the compound, (iii) measuring the proliferation ($Reg_2$) of the human $CD4^+CD25^+$ cells in the absence of the compound, wherein the compound that induces $Reg_1$/$Reg_2$>1 is identified as the compound that induces immune tolerance in the patient; (iv) using the compound identified in step (iii) as a reference sequence to search a library or collection of compounds for one or more compounds having homology to the reference sequence; (v) identifying one or more compound having homology to the reference sequence; and (vi) repeating steps (i)-(iii) with one or more compounds identified in step (v).

In another embodiment, the present disclosure relates to a method of identifying a compound comprising an epitope that induces immune tolerance in a patient suffering from an autoimmune disease, comprising (a) identifying in vitro a compound from a library or collection of compounds that (i) elicits a response (RespH) from a T-resp of a healthy individual, and (ii) elicits a response (RespP) from a T-resp of the patient, wherein the compound that induces a RespH/RespP<1 is identified as the compound that induces immune tolerance in the patient; (b) using the compound identified in step (a)(ii) as a reference sequence to search a library or collection of compounds for one or more compounds having homology to the reference sequence; (c) identifying one or more compounds having homology to the reference sequence; and (d) repeating step (a) with one or more compounds identified in step (c).

In certain embodiments, the compound that is used as a reference sequence to search a library or collection of compounds is identified using a mixed-cell assay, as described above.

In various embodiments, the present disclosure relates to a method of identifying a compound comprising an epitope that induces immune tolerance in a patient suffering from an autoimmune disease comprising the steps of (a) identifying in vitro a compound from a library or collection of compounds that (i) elicits a response (RespH) from responder T-cells of a healthy individual; and (ii) elicits a response (RespP) from responder T-cells of the patient; (b) determining the total number of T-cells (P1) from the healthy individual that provides an amount of T-reg cells that induces 50% suppression of T-resp activity in the presence of said compound; (c) determining the total number of T-cells (P2) from the patient that provides an amount of T-reg cells that induces 50% suppression of said T-resp activity in the presence of said compound, (d) identifying the compound that induces a RespH/RespP<1, a P1/P2>1 or RespH/RespP<1 and a P1/P2>1 as the compound that induces immune tolerance in the patient; (e) using the compound identified in step (d) as a reference sequence to search a library or collection of compounds for one or more compounds having homology to the reference sequence; (f) identifying one or more compounds having homology to the reference sequence; and (g) repeating steps (a)-(d) with one or more compounds identified in step (f).

In certain embodiments, the one or more compounds identified in the foregoing methods as having homology to a reference sequence has at least about 60%, such as at least about 65%, at least about 70%, at least about 75%, at least about 80%, at least about 85%, at least about 90% or at least about 95% homology to the reference sequence. In other embodiments, the one or more compounds identified as having homology to the reference sequence has more than about 95% homology to the reference sequence.

The skilled artisan will further appreciate that homology between a reference sequence (i.e., a compound identified by an in vitro method described above in this section) and a compound identified as having homology to the reference sequence set forth in this section may indicate not only a tolerizing epitope candidate, but also, the etiology of the autoimmune disease in a particular subject. Accordingly, the present disclosure relates to a method of determining the etiology of an autoimmune disease in a patient comprising the steps of (i) identifying a compound comprising an epitope in vitro from a library or collection of compounds that induces immune tolerance in a human patient by any of the methods described herein; (ii) using the compound identified in step (i) as a reference sequence to search a library or collection of compounds for one or more compounds having homology to the reference sequence; (iii) identifying one or more compounds having at least about 60% homology to the reference sequence, wherein the etiology of the compound identified in step (iii) is indicative of the etiology of the autoimmune disease. In certain embodiments, the method comprises a step (iii) of identifying one or more compounds having at least about 65%, at least about 70%, at least about 75%, at least about 80%, at least about 85%, at least about 90% or at least about 95% homology or more to the reference sequence.

It will be understood by the skilled artisan that a compound identified by the methods described herein may be optimized to improve efficacy by altering or augmenting certain properties. Accordingly, in some embodiments, a compound may be optimized, e.g., to improve solubility, absorption and/or stability of the compound, to prolong its half-life in the body, or to target a specific organ. In some embodiments, optimization may include altering the molecular weight, length and chemical make-up of the compound. In one embodiment, the compound is a peptide. In these embodiments, a peptide can be optimized by, e.g., adding or removing amino acids, introducing conservative or non-conservative amino acid substitutions at various positions, incorporating non-natural amino acids, and cross-linking to other peptides or non-peptide therapeutic agents.

The skilled artisan will appreciate that optimization of a compound identified by the methods set forth herein may be an iterative process, comprising alteration of the compound followed by retesting of the altered compound in an in vitro assay described herein. The skilled artisan will further appreciate that the analyses set forth in this section may lead to the design of more effective tolerizing epitopes and/or therapeutic effectors that act directly on the disease condition.

7.2. Methods of Treatment

The phrases "treatment of," "treating", and the like include the amelioration or cessation of a condition or a symptom thereof. In one embodiment, treating includes inhibiting, for example, decreasing the overall frequency of episodes of a condition or a symptom thereof. In various embodiments, the condition is an autoimmune disease.

The phrases "prevention of," "preventing", and the like include the avoidance of the onset of a condition or a symptom thereof.

In accordance with the invention, in some embodiments, the compounds described herein are administered to a patient in need of treatment or prevention of an autoimmune disease. In some embodiments, the compounds are administered to a patient in need of treatment or prevention of age-related macular degeneration.

In certain embodiments, a patient suffering from an autoimmune disease is treated by administering an effective amount of regulatory T-cells trained in the presence of a compound comprising an epitope that induces immune tolerance, wherein the compound is identified as the compound that (a) elicits a response (RespP) from a responder T-cell of the patient; (b) elicits a response (RespH) from a responder T-cell of the patient; (c) elicits a response (RegH) from a regulatory T-cell of a healthy individual; and (d) elicits a response (RegP) from a regulatory T-cell of the patient, wherein the compound induces a RespH/RespP<1, a RegH/RegP≥1 or a RespH/RespP<1 and a RegH/RegP≥1. As used herein, a cell is "trained" when it is exposed to a compound identified by the methods described herein. In various embodiments, the phenotype of the cell is altered upon exposure to a compound identified by the methods described herein. In other embodiments, the regulatory T-cells are not trained before administration. In various embodiments, the regulatory T-cells are expanded but not trained. In still other embodiments, the regulatory T-cells are trained in vivo by administration of a compound identified by the methods described herein before, concurrently with or subsequent to administration of the regulatory T-cells.

In other embodiments, the patient is treated by (a) administering an effective amount of regulatory T-cells and (b) administering a compound that (i) elicits a response (RespP) from a responder T-cell of the patient; (ii) elicits a response (RespH) from a responder T-cell of the patient; (iii) elicits a response (RegH) from a regulatory T-cell of a healthy individual; and (iv) elicits a response (RegP) from a regulatory T-cell of the patient, wherein the compound induces a RespH/RespP<1 and a RegH/RegP≥1. In certain embodiments, the T-cells administered in step (a) are trained and the compound used to train them is identical to the compound administered in step (b). In other embodiments, the compound used to train the T-reg cells administered in step (a) is different from the compound administered in step (b). In one particular embodiment, the T-reg cells are not trained. In some embodiments, the T-reg cells are expanded but not trained. Accordingly, in some embodiments, the compound is administered after administration of the T-reg cells in order to train and/or maintain the T-reg cell population in the patient.

7.3. Compositions and Administration of Compounds Comprising an Epitope that Induces Immune Tolerance When administered to a patient, a compound identified by the methods described herein may be administered alone or as a component of a composition further including a pharmaceutically acceptable carrier or excipient. Pharmaceutical compositions comprising one or more of the compounds may be administered by absorption through mucocutaneous linings (e.g., oral, nasal, rectal, and intestinal mucosa, etc.). Administration may be systemic or local. Methods of administration include, but are not limited to, oral, sublingual, intravaginal, rectal, by inhalation and parenterally. Administration may, for example, include or consist of oral ingestion. Administration may, for example, include or consist of buccal administration via, for example, a buccal patch or gel composition. Administration may, for example, include or consist of nasal administration via, for example, a nasal gel or spray formulation. Administration may, for example, be transdermal via, for example, a transdermal patch delivery system. Administration may, for example, include or consist of inhalation, such as inhalation of a dry powder formulation.

In particular embodiments, the compound is administered with one or more enhancers, which may be part of the same pharmaceutical formulation as the compound or separately co-administered. As used herein, an "enhancer" is any compound or mixture of compounds that potentiates the immune suppressive response of T-reg cells. In some embodiments, the enhancer is high molecular weight hyaluronic acid, as previously described. Enhancers that may be used alone or in combination include, but are not limited to, high molecular weight hyaluronic acid, IL-2, IL-15, TGF-β, all-trans retinoic acid, rapamycin, anti-CD3, anti-CD28, vitamin D3, dexamethasone, IL-10, idolamine-2,3-dioxygenase, FTY720, a sphingosine kinase 1 inhibitor, cholera toxin B subunit, ovalbumin, Flt2L, sirolimus and/or anti-thymocyte globulin, CTLA-4/Ig, and mixtures thereof. The one or more enhancers may include a sphingosine kinase 1 inhibitor as disclosed in U.S. Pat. No. 8,872,888.

The compositions described herein may optionally comprise a suitable amount of a pharmaceutically acceptable excipient so as to provide the form for proper administration to the patient. Examples of pharmaceutical excipients include a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient may be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to a patient. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, may also contain minor amounts of wetting or emulsifying agents, or pH buffering agents. Specific examples of pharmaceutically acceptable carriers and excipients that may be used to formulate oral dosage forms are described in the *Handbook of Pharmaceutical Excipients*, American Pharmaceutical Association (1986).

The pharmaceutical compositions of the invention may, for example, take the form of solutions, suspensions, emulsions, tablets, pills, pellets, capsules, capsules containing liquids, powders, sustained-release formulations, suppositories, rectal suppositories, emulsions, aerosols, sprays, suspensions, or any other form suitable for use. Examples of suitable pharmaceutical excipients are described in *Remington's Pharmaceutical Sciences* 1447-1676 (Alfonso R. Gennaro ed., 19th ed. 1995). Without limitation, the invention provides pharmaceutical compositions, such as orally administrable pharmaceutical compositions, that include one or more of the peptides disclosed herein, for example, in a therapeutically effective amount for the treatment of an autoimmune-related condition, such as those disclosed herein.

In one embodiment, the compounds are formulated in accordance with routine procedures as a composition adapted for oral administration. A compound to be orally delivered or ingested can be in the form of tablets, capsules, gelcaps, caplets, lozenges, aqueous or oily solutions, suspensions, granules, powders, emulsions, syrups, or elixirs, for example. When a compound is incorporated into oral tablets, such tablets may be compressed tablets, tablet triturates (e.g., powdered or crushed tablets), enteric formulations (minimal/no release in the gastric environment, released in the intestines), enteric-coated tablets, sugar-coated tablets, film-coated tablets, multiply compressed tablets or multiply layered tablets. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16$^{th}$ ed., Mack Publishing, Easton, Pa. 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems*, (Lieberman, Rieger and Banker, eds.) published by Marcel Dekker, Inc.

An orally administered composition may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. A time-delay material such as glycerol monostearate or glycerol stearate can also be used. Oral compositions can include standard excipients such as mannitol, lactose, starch, magnesium stearate, sodium saccharin, cellulose, and magnesium carbonate.

Alternatively, when a compound is to be administered via inhalation, it may be formulated into a dry aerosol, such as a dry powder formulation, or can be formulated into an aqueous or partially aqueous solution.

In various embodiments, when a compound is to be administered parenterally, e.g., intravenously or by injection, it may be provided in the form of a solution, e.g., an isotonic sterile solution. Such a solution may, for example, be reconstituted from a dry pharmaceutical form, such as a prepackaged reconstitutable dry pharmaceutical form.

Some embodiments of the invention are directed to compositions including one or more synthetic peptides or the use of one or more synthetic peptides. A peptide may be synthesized and/or provided and/or used in at least substantially pure form or pure form. For example, the peptide may be at least 95% pure or at least 98% pure. Peptides may be synthesized using commercially available synthesizers and purified by conventional means such as HPLC. The at least substantially pure peptide(s) may be mixed or formulated with one or more pharmaceutical excipients such as but not limited to those exemplified herein.

Some embodiments of the invention are directed to compositions and their use, which compositions include retinal S-antigen isolated and at least partially or at least substantially purified from animal ocular tissue, such as bovine, ovine, porcine or other non-human mammalian sources, or derived from such isolated and at least partially/substantially purified animal S-antigen, for example, via partial proteolytic degradation. Numerous suitable methods for purifying retinal S-antigen from biological sources are described in the literature and incorporated by reference herein including, but not limited to, the methods of: Kasp et al., *An improved method for the purification of retinal S-antigen using selective hydrophobic adsorption chromatography*, J Immunol Methods 1987 Jun. 26; 100(1-2):147-52 (describing the use of phenyl-Sepharose CL-4B as a solid-phase hydrophobic adsorbent in the purification of S-antigen from protein extracts of bovine, porcine and human tissue); Al-Mandawi et al., *A simplified method for the isolation of highly purified bovine retinal S antigen*, Journal of Neuroimmunology, Vol 14, Issue 1, 99-108 (preparation of highly purified S-antigen using a one-step ion-exchange method); Molinotti et al., *One-step purification by high-performance liquid chromatography of retinal S-antigen*, Research in Clinic and Laboratory, December 1989, Vol 19, Issue 1, 259-266; Borthwick and Forrester, *Purification of retinal S-antigen by ion-exchange chromatography and chromatofocusing*, Exp Eye Res. 1983 December; 37(6):613-25 (isolation of bovine retinal S-antigen by ion-exchange chromatography on DEAE Sephadex, alone or in combination with a chromatafocusing step); and Mahlberg, *Purification of Bovine and Human Retinal S-Antigen Using Immunoabsorbent Polymer Particles*, Ophthalmic Res 1989; 21:126-133 (bovine retinal S-antigen prepared using gel filtration chromatography followed by DEAE A-50 or QAE A-50 anion-exchange chromatography with a final purification performed using immunoadsorbents made from polymerized polyvalent antiserum (rabbit) to bovine serum components). Partial digestion or degradation may, for example, be performed according to the method of Banga et al., *Antigenicity and uveitogenicity of partially purified peptides of a retinal autoantigen, S-antigen*, Immunology 1987 July; 61(3):357-62 (partial chemical digestion of retinal S-antigen with cyanogen bromide to generate various peptide fragments).

The amount of compound that is effective for the treatment or prevention of a condition may be determined by standard clinical techniques. In addition, in vitro and/or in vivo assays may optionally be employed to help identify optimal dosage ranges. The precise dose to be employed will also depend on, e.g., the route of administration and the seriousness of the condition, and can be decided according to the judgment of a practitioner and/or each patient's circumstances. In other examples thereof, variations will necessarily occur depending upon the weight and physical condition (e.g., hepatic and renal function) of the patient being treated, the affliction to be treated, the severity of the symptoms, the frequency of the dosage interval, the presence of any deleterious side-effects, and the particular compound utilized, among other things.

Administration may be as a single dose or as a divided dose. In one embodiment, an effective dosage is administered once per month until the condition is abated. In another embodiment, the effective dosage is administered once per week, or twice per week or three times per week until the condition is abated. An effective dosage may, for example, be administered at least once daily or at least or at least once every two-days, or at least once every three days, four days, five days, six days or seven days. In another embodiment, an effective dosage amount is administered about every 24 h until the condition is abated. In another embodiment, an effective dosage amount is administered about every 12 h until the condition is abated. In another embodiment, an effective dosage amount is administered about every 8 h until the condition is abated. In another embodiment, an effective dosage amount is administered about every 6 h until the condition is abated. In another embodiment, an effective dosage amount is administered about every 4 h until the condition is abated. The effective dosage amounts described herein refer to total amounts administered; that is, if more than one compound is administered, the effective dosage amounts correspond to the total amount administered.

The duration of treatment by administration of a therapeutic compound or combination according to the invention may continue for a plurality of days, such as for at least one week, at least two weeks, at least three weeks, at least four weeks, at least two months, at least three months, at least four months, at least five months, at least six months, at least seven months, at least eight months, at least nine months, at least 10 months, at least 11 months, at least 12 months, at least 1½ years, at least 2 years, at least three years, at least four years, or may continue indefinitely.

In various embodiments, the compound can be administered together with a second therapeutically active agent. In some embodiments, the additional agent is a dietary supplement such as a vitamin, a mineral, or an ω-3 fatty acid. In other embodiments, the second therapeutically active agent is an anti-inflammatory agent, e.g., a corticosteroid. In still other embodiments, the second therapeutically active agent is an anti-bacterial agent, an antihelmintic agent or an anti-fungal agent. In certain embodiments, the second therapeutically active agent is an anti-viral agent.

In one embodiment, a compound is administered concurrently with a second therapeutic agent as a single composition comprising an effective amount of the compound and an effective amount of the second therapeutic agent. Alternatively, a composition comprising an effective amount of a compound and a second composition comprising an effective amount of the second therapeutic agent are concurrently administered. In another embodiment, an effective amount of a compound is administered prior or subsequent to administration of an effective amount of the second therapeutic agent. In this embodiment, the compound is administered while the second therapeutic agent exerts its therapeutic effect, or the second therapeutic agent is administered while the compound exerts its therapeutic effect for treating or preventing a condition.

An effective amount of the second therapeutic agent will be known to the art depending on the agent. However, it is well within the skilled artisan's purview to determine the second therapeutic agent's optimal effective-amount range. In some embodiments of the invention, where a second therapeutic agent is administered to a patient for treatment of a condition, the minimal effective amount of the compound will be less than its minimal effective amount would be where the second therapeutic agent is not administered. In this embodiment, the compound and the second therapeutic agent can act synergistically to treat or prevent a condition.

A composition embodiment of the invention may be prepared by a method including admixing a compound or a pharmaceutically acceptable derivative thereof with a pharmaceutically acceptable carrier or excipient. Admixing may be accomplished using methods known for admixing compounds, e.g., for mixing a peptide and a pharmaceutically acceptable carrier or excipient. In one embodiment, the compound is present in the composition in a therapeutically effective amount.

7.4. Cell-Based Therapy

In certain embodiments, a patient suffering from an autoimmune disease is treated by administering T-reg cells. In some embodiments, the T-reg cells are autologous T-reg cells isolated from the patient. In other embodiments, the T-reg cells are heterologous T-reg cells isolated from a healthy individual. In these embodiments, the heterologous T-reg cells are compatible with the patient. As used herein, a heterologous T-cell is "compatible" with the patient if it is isolated from a partially HLA-matched individual. In some embodiments, the T-reg cells are cryopreserved cells. In particular embodiments, the T-reg cells are from a cell bank. In other particular embodiments, the T-reg cells are derived from undifferentiated umbilical cord stem cells.

In various embodiments, the T-reg cells are trained before administration to a patient. In other embodiments, the T-reg cells are not trained before administration to a patient. In some embodiments, the T-reg cells are trained in vitro in the presence of a compound identified by the methods described herein. In other embodiments, the T-reg cells are trained in vivo after administration, for example, by administering a compound identified by the methods described herein before, concurrently with or subsequent to administration of the T-reg cells. In various embodiments, the T-reg cells are expanded but are not trained. In still other embodiments, the T-reg cells that are not expanded are infused into the blood of a patient and are expanded in vivo.

In some embodiments, precursor cells are induced to become T-reg cells. For example, induced T-reg (iTreg) cells may be generated according to the method of Ellis et al. (2012) J Vis Exp. (62) e3738:1-5, or of Liu et al. (2010) Scand. J. Immun. 71:12-19, or other methods known in the art. In some embodiments, the precursor cells are induced in the presence of a compound identified by the methods described herein. In other embodiments, the precursor cells are induced to become T-reg cells, and the induced T-reg cells are subsequently trained with a compound identified by the methods described herein. In particular embodiments, the induced T-reg cells are expanded in vitro in the presence of a compound identified by the methods described herein. In various embodiments, the induced T-reg cells are expanded in vivo by administering induced T-cells to the patient and administering an effective amount of a compound as identified by a method described herein before, concurrently with or subsequent to administering the T-cells. In some embodiments, the precursor cells are autologous cells of the patient. In other embodiments, the precursor cells are heterologous cells that are compatible with the patient. In particular embodiments, the heterologous precursor cells are from a healthy individual. In various embodiments, the induced T-reg cells are antigen specific. In other embodiments, the induced T-reg cells are polyclonal.

In various embodiments, T-reg cells or precursor cells are isolated from the peripheral blood. In some embodiments, T-reg cells or precursor cells are isolated from fresh peripheral blood. In other embodiments, T-reg cells or precursor cells are isolated from cryopreserved peripheral blood. In still other embodiments, T-reg cells or precursor cells are isolated from umbilical cord stem cells.

Regulatory T-cell populations useful in the cell therapies described herein will be evident to the skilled artisan. Such cells include, but are not limited to, natural $CD4^+CD25^+$ thymus-derived T-cells, natural $CD4^+CD25^+Foxp3^+$ cells, $CD4^+CD25^+$ T-cells induced ex vivo by stimulation of $CD4^+$ cells induced with alloantigens in the presence of TGF-β, $CD4^+$, Tr1 cells induced ex vivo with mitogens and IL-10 or immature dendritic cells, $CD4^+$ Th3/Tr2 cells induced ex vivo with mitogens or superantigens in the presence of IL-2 and TGF-β, $CD8^+$ Tr1 or Tr2 cells induced ex vivo with mitogens in the presence of IL-10 or TGF-β with plasmacytoid dendritic cells, $CD4^+$ T-cells stimulated with anti-CD3 and complement regulator anti-CD46, $CD4^+CD25^+$ cells induced by specific antigens (e.g., HLA class II tetramers) or TGF-β, TGF-β converted $CD4^+CD25^+$ T-cells, $CD4^+CD25^+CD127^{low}$ T-cells, $CD4^+CD127^{lo/-}$ T-cells, $CD4^+CD127^{lo/-}CD25^+$ T-cells, and the $CD54RA^+$ subset of $CD4^+CD127^{lo/-}CD25^+$ T-cells. Other T-cells that can be used in the methods described herein will be known to the skilled artisan, and can be found, for example in Horwitz et al. (2004) Seminars in Immunology 16:135-143. See also Mayer et al. (2012) PloS One 7(1); Putnam et al. (2009) Diabetes 58:652-662; Walker et al. (2005) Proc. Nat'l. Acad. Sci. 102(11):4103-4108.

In particular embodiments, either $CD4^+$ and/or $CD8^+$ precursor cells are isolated from the peripheral blood lymphocytes of an individual and are induced to become T-reg cells. In certain embodiments, the individual is the patient. In other embodiments, the individual is a healthy donor compatible with the patient. In still other embodiments, the cells are isolated from a cell bank. In some embodiments, the T-reg cells are expanded. In a preferred embodiment, the T-reg cells are able to train other T-cells to become T-reg cells.

In some embodiments, T-reg cells or precursor cells are separated from the peripheral blood before training and/or expansion in the presence of a compound identified by the methods described herein. T-reg cells or precursor cells can be isolated by any method known in the art. In some embodiments, T-reg cells and/or precursor $CD4^+$ and/or $CD8^+$ cells are isolated and purified by any technique known in the art. Methods of characterizing phenotypes of isolated and purified cells will be known to the skilled artisan and include positive or negative selection with magnetic beads and/or flow cytometry. See, e.g., Cao et al. (2010) Clinical Immunol. 136:329-337; Di Ianni et al. (2012) Transfusion and Apheresis Science 47:213-216; Walker et al. (2005) P.N.A.S. 102(11):4103-08; Chai et al. (2008) J. Immunol. 180:858-869; Tang et al. (2004) J. Exp. Med. 199(11):1455-65; Lin et al. (2003) Eur. J. Immunol. 33:626-638.

In certain embodiments, T-reg cells or precursor cells of a particular phenotype are enriched by, for example, negative selection based on cell surface markers using AutoMACS technology (Miltenye Biotec, Cambridge, Mass., USA) and/or FACs. In certain embodiments, T-reg cells are enriched by negative selection (e.g., by removing cells with markers that are not present on T-reg cells) followed by positive selection (e.g., by isolating cells using an antibody specific for a marker that is present on T-cells, such as CD25). In some embodiments, T-reg cells are expanded by incubation with anti-CD3 and/or anti-CD28 antibodies, for example, antibodies coupled to paramagnetic beads, in the presence of IL-2 followed by FACs analysis of various cell markers (e.g., CD25 and/or CD4). In various embodiments, the T-cells are expanded and/or trained and expanded in the presence of one or more enhancers. In some embodiments, the enhancer is high molecular weight hyaluronic acid. Enhancers that may be used alone or in combination include, but are not limited to, high molecular weight hyaluronic acid, IL-2, IL-15, TGF-β, all-trans retinoic acid, rapamycin, anti-CD3, anti-CD28, vitamin D3, dexamethasone, IL-10, idolamine-2,3-dioxygenase, FTY720, a sphingosine kinase 1 inhibitor, cholera toxin B subunit, ovalbumin, Flt2L, sirolimus and/or anti-thymocyte globulin, CTLA-4/Ig, and mixtures thereof. The one or more enhancers may include a sphingosine kinase 1 inhibitor as disclosed in U.S. Pat. No. 8,872,888.

In certain embodiments, the T-reg cells or precursor cells are isolated and expanded by at least about 10-fold, such as by at least about 20-fold, by at least about 30-fold, by at least about 40-fold, by at least about 50-fold, by at least about 60-fold, by at least about 70-fold, by at least about 80-fold, by at least about 90-fold or by at least about 100-fold before therapeutic administration.

T-reg cells may be expanded by any method known in the art. In a particular embodiment, the cells are expanded in vitro in an isotonic medium such as CellGro medium, supplemented with autologous serum (10%) in the presence of IL-2 and clinical-grade anti CD3/anti-CD28 beads (1:1 ratio with cells). Cells are expanded for at least 7 days, for at least 8 days, for at least 9 days, for at least 10 days, for at least 11 days, for at least 12 days, for at least 13 days or for at least 14 days. In some embodiments, cells are not expanded past 14 days. In some embodiments, expanded cells are tested for their ability to suppress INF-γ production and also for microbial contamination before infusion.

In various embodiments, T-reg cells that are either expanded or not expanded are administered in an amount to achieve a T-reg/T-resp ratio in the blood of the patient of about 0.01, such as of about 0.05, of about 0.1, of about 0.25, of about 0.5, of about 0.75 or of about 1. The skilled artisan will understand that this ratio will depend on a number of factors, including but not limited to, the nature and severity of the autoimmune disease, the potency of the T-reg cells and the potency of the T-resp cells, and must be optimized for the particular individual and disease state.

In certain embodiments, T-reg cells are infused at a dose of at least about $0.1 \times 10^5$/kg body weight, such as a dose of at least about $5 \times 10^5$ cells/kg body weight, at least about $10 \times 10^5$ cells/kg, at least about $20 \times 10^5$ cells/kg body weight, at least about $30 \times 10^5$ cells/kg body weight, at least about $40 \times 10^5$ cells/kg body weight, at least about $50 \times 10^5$ cells/kg body weight, at least about $60 \times 10^5$ cells/kg body weight, at least about $70 \times 10^5$ cells/kg body weight, at least about $80 \times 10^5$ cells/kg body weight, at least about $90 \times 10^5$ cells/kg body weight, at least about $10 \times 10^6$ cells/kg body weight, at least about $15 \times 10^6$ cells/kg body weight, or at least about $20 \times 10^6$ cells/kg body weight or more.

T-reg cells are typically administered by injection or intravenous infusion. For infusion, T-reg cells are administered in a sterile, isotonic solution, for example, normal saline (e.g., 0.9% NaCl) and 5% human albumin or lactated Ringer's solution.

In some embodiments, inhibitory effects from an injection of trained and/or expanded T-reg cells can persist for at least about 1 week, such as for at least about 2 weeks, for at least about 3 weeks, for at least about 1 month or more. In particular embodiments, the patient's blood is tested periodically to determine whether the expanded T-reg cells continue to exert inhibitory effects, and additional injections of T-reg cells are administered when needed.

In certain embodiments, the T-reg cells are administered in conjunction with an additional therapeutically active agent. An additional therapeutically active agent for administration in conjunction with T-reg cells may be selected based on one or more factors known to the skilled artisan, including, but not limited to, the autoimmune disease being treated, the stage of the disease, and the overall health of the patient. Appropriate therapeutic agents will be known to the skilled practitioner. In some embodiments, the additional agent is a dietary supplement such as a vitamin, a mineral, or an ω-3 fatty acid. In other embodiments, the second therapeutically active agent is an anti-inflammatory agent, e.g., a corticosteroid. In particular embodiments, the T-reg cells are administered with an enhancer.

7.5. Combination Compound and Cell-Based Therapy

In certain embodiments, the patient is treated by administering (a) an effective amount of T-reg cells; and (b) an effective amount of a compound comprising an epitope that induces immune tolerance identified by the methods described herein. In certain embodiments, the T-reg cells are not trained before administration. In various embodiments, the T-reg cells are expanded, but are not trained, before administration. In still other embodiments, the T-reg cells are trained before administration in the presence of a compound comprising an epitope that induces immune tolerance as identified by the methods described herein. In other embodiments, the T-reg cells are trained and/or expanded in vivo in the presence of a compound as identified herein. Accordingly, in these embodiments, a compound as identified herein is administered before, concurrently with or subsequent to administration of the T-reg cells. In some embodiments, T-reg cells are trained in vitro and the compound used to train the T-reg cells for the combination therapy is identical to the compound that is administered to the patient. In other embodiments, the compound used to train the T-reg cells for the combination therapy is different from the compound that is administered to the patient. In various embodiments, the epitope of the compound used to train T-reg cells for combination therapy is identical to the epitope of the compound that is administered to the patient. In other embodiments, the epitope of the compound used to train T-reg cells for combination therapy is different from the epitope of the compound that is administered to the patient.

In certain embodiments, the T-reg cells are selected from the group consisting of $CD4^+CD25^+$ T-cells, $CD4^+Foxp3^+$ T-cells, $CD4^+CD25^+Foxp3^+$ T-cells, IL-10 producing $CD4^+$ Tr1 cells, TGF-β producing Th3 cells, $CD8^+$ NKT cells, $CD4^-CD8^-$ T-cells, γδ T-cells, thymic nT-reg cells, periphery induced i-Treg cells, tolerogenic dendritic cells (DC), $CD4^+CD127^{lo/-}$ T-cells, $CD4^+CD127^{lo/-}$ $CD25^+$ T-cells, $CD45RA^+$ subset of $CD4^+CD127^w$ $CD25^+$ T-cells and mixtures thereof.

In some embodiments, the T-reg cells and the compound are administered concurrently. In other embodiments, the T-reg cells and the compound are administered consecutively. For concurrent or consecutive administration, the T-reg cells and the compound are administered in amounts that are therapeutically effective in combination. In certain embodiments when the T-reg cells and the compound are administered consecutively, the compound is administered before the T-reg cells. In these embodiments, the T-reg cells are administered at least about 1 hour, such as least about 1 day, at least about 1 week, or at least about 1 month or more after administration of the compound. In other embodiments when the T-reg cells and the compound are administered consecutively, the T-reg cells are administered first and the compound is administered subsequent to the cell therapy. In various embodiments, the compound is administered at least about 1 hour, such as least about 1 day or at least about 1 week, or at least about 1 month or more after administration of the compound. In these embodiments, the duration of time between administration of the T-reg cells and the compound is informed by the population of T-reg cells in the patient's blood over time. Thus, as part of either a monotherapy or a combination therapy T-reg cells from the patient's blood can be isolated, counted and assayed for their ability to suppress T-resp cells.

In various embodiments, administration of a compound to a patient who has received either cell therapy alone or a combination of compound and cell therapy is utilized to maintain a healthy number of active T-reg cells in the patient's peripheral blood over time, such as over about 2 weeks, or about 1 month, or about 2 months, or about 3 months or more. Thus, in these embodiments, the compound is administered multiple times after the initial therapy, such as about once per week, twice per week, or every day for a period of time, e.g., 1 week, 1 month, 6 months or 1 year or more. It will be understood by a person of skill in the art that, in the combination therapy the T-reg cells and the compound can be administered in different formulations and by different routes, e.g., the T-reg cells are administered by infusion and the peptide is orally administered, or in the case of concurrent administration, the T-reg cells and the compound are administered in the same formulation, for example, by infusion.

In various embodiments, the T-reg cells and/or the compound can be administered in the presence of, such as co-administered with, one or more enhancers. In some embodiments, the enhancer is high molecular weight hyaluronic acid. Enhancers used alone or in combination may include, but are not limited to, high molecular weight hyaluronic acid IL-2, IL-15, TGF-β, all-trans retinoic acid, rapamycin, anti-CD3, anti-CD28, vitamin D3, dexamethasone, IL-10, idolamine-2,3-dioxygenase, FTY720, a sphingosine kinase 1 inhibitor, cholera toxin B subunit, ovalbumin, Flt2L, sirolimus and/or anti-thymocyte globulin, CTLA-4/Ig, and mixtures thereof. In certain embodiments, the one or more enhancers includes a sphingosine kinase 1 inhibitor as disclosed in U.S. Pat. No. 8,872,888.

The compound may be administered as a single dose or as a divided dose as needed. In one embodiment, an effective dosage is administered once per month. In another embodiment, the effective dosage is administered once per week, or twice per week or three times per week. In another embodiment, an effective dosage amount is administered about every 24 h. In another embodiment, an effective dosage amount is administered about every 12 h. In certain embodiments, more than one compound can be administered. Thus, the effective dosage amounts described herein refer to total amounts administered; that is, if more than one compound is administered, the effective dosage amounts correspond to the total amount administered. In certain embodiments, the patient's blood is tested periodically to detect the presence and number of T-reg cells and the dosage and administration of a compound is administered based on the results.

It will be understood by the skilled artisan that, with combination therapies where compounds and T-reg cells are administered separately, the route, duration and frequency of dosing regimens may differ. For example, a compound may be orally administered once per day for 6 months, while T-reg cells may be administered by infusion once per month for a year.

7.6. Treatment of Immune Diseases of the Eye

In particular embodiments, the invention provides methods of treating AMD in a patient by administering a compound identified by the methods described herein. In another embodiment, the invention provides methods of treating AMD in a patient by administering T-reg cells that have been expanded in the presence of a compound identified by the methods described herein. In yet another embodiment, the invention provides methods of treating AMD in a patient by administering a compound and T-reg cells in a combination therapy, wherein the compound is identified by a method described herein, and wherein, in some embodiments, the T-reg cells are trained in the presence of a compound identified by a method described herein. In other embodiments, T-reg cells are expanded, but are not trained.

In another particular embodiment, the invention provides methods of treating uveitis in a patient by administering a compound identified by the methods described herein. In another embodiment, the invention provides methods of treating uveitis in a patient by administering T-reg cells that have been expanded in the presence of a compound identified by the methods described herein. In yet another embodiment, the invention provides methods of treating uveitis in a patient by administering a compound and T-reg cells in a combination therapy, wherein the compound is identified by a method described herein, and wherein, in some embodiments, the T-reg cells are trained in the presence of a compound identified by a method described herein. In other embodiments, T-reg cells are expanded, but are not trained.

In certain embodiments, a compound that induces immune tolerance in a human patient suffering from AMD or uveitis is identified in vitro from a library or collection of compounds by identifying a compound that induces a response from a T-resp cell of the patient that is greater than a response from a T-resp cell of a healthy individual, wherein the compound that induces a response from a T-resp cell of the patient that is greater than the response from a T-resp cell of the healthy individual is identified as the compound that induces immune tolerance. In other embodiments, a compound that induces immune tolerance in a human patient suffering from AMD or uveitis is identified in vitro from a library or collection of compounds by identifying a compound that induces a response from a T-reg cell of a healthy individual that is greater than a response from a T-reg cell of the patient, wherein the compound that induces a response from a T-reg cell of the healthy individual that is greater than the response from a T-reg cell of the patient is identified as the compound that induces immune tolerance in the patient.

In some embodiments, the T-reg cells are autologous to the patient. In other embodiments, the T-reg cells are heterologous and compatible to the patient and are from a healthy individual. In certain embodiments, precursor cells are trained to become T-reg cells, as described above. In various embodiments, the T-reg cells are antigen-specific. In other embodiments, the T-reg cells are not antigen-specific.

In various embodiments, a compound identified in vitro as described above in section 6.1 is used as a reference sequence to search a library of compounds to identify one or more compounds that have homology to the reference sequence. In these embodiments, the identified compound that has homology to the reference sequence is a compound that induces immune tolerance in a human patient suffering from an autoimmune disease, such as AMD or uveitis. In various embodiments, the compound identified by this method is a protein or a peptide from a protein that belongs to the same class of proteins as the reference sequence (e.g., S-antigen). In other embodiments, the compound identified by this method is a protein or a peptide from a protein that belongs to a class of proteins unrelated to the reference sequence (e.g., a bacterial protein). In various embodiments, the reference sequence is selected from the S-antigen peptides VTVDVTNNTEKTVKK (SEQ ID NO: 3) or GEPIPVTVDVTNNTEKTVKK (SEQ ID NO: 2).

In still other embodiments, a patient suffering from AMD or uveitis can be treated by a combination of a compound identified by any of the methods described herein and T-reg cells. In some embodiments, the therapies are administered concurrently. In other embodiments, the therapies are administered consecutively. In various embodiments, the T-reg cells are trained and the epitope of the compound used to train T-reg cells for combination therapy is identical to the epitope of the compound that is administered to the patient in the combination therapy. In other embodiments, the T-reg cells are trained and the epitope of the compound used to train T-reg cells for combination therapy is different from the epitope of the compound that is administered to the patient. In various embodiments, the T-reg cells are trained and the compound used to train T-reg cells for combination therapy is identical to the compound that is administered to the patient in the combination therapy. In other embodiments, the T-reg cells are trained and the compound used to train T-reg cells for combination therapy is different from the compound that is administered to the patient. In still other embodiments of the monotherapy and the combination therapy, T-reg cells are not trained before administration. In certain embodiments, T-reg cells are expanded but are not trained before administration. In some embodiments, T-reg cells are trained in vivo by administering a compound as described herein before, concurrently with or subsequent to administration of untrained T-reg cells.

In other embodiments when the T-reg cells and the compound are administered consecutively, the T-reg cells are administered first and the compound is administered subsequent to the cell therapy. In various embodiments, the compound is administered at least about 1 hour, such as least about 1 day or at least about 1 week, or at least about 1 month or more after administration of the compound. In these embodiments, the duration of time between administration of the T-reg cells and the compound are informed by the population of T-reg cells in the patient's blood over time. Thus, as part of the combination therapy T-reg cells from the patient's blood can be isolated, counted and assayed for their ability to suppress T-resp cells. Accordingly, in one embodiment, administration of a compound to a patient who has received cell therapy alone or a combination of compound and cell therapy is utilized to maintain a healthy number of active T-reg cells in the patient's peripheral blood over time, such as about 2 weeks, or about 1 month, or about 2 months, or about 3 months or more.

In various embodiments, the T-reg cells and/or the compound are administered with one or more enhancers. In some embodiments, the enhancer is high molecular weight hyaluronic acid. Enhancers that may be used alone or in combination include, but are not limited to, high molecular weight hyaluronic acid, IL-2, IL-15, TGF-β, all-trans retinoic acid, rapamycin, anti-CD3, anti-CD28, vitamin D3, dexamethasone, IL-10, idolamine-2,3-dioxygenase, FTY720, a sphingosine kinase 1 inhibitor, cholera toxin B subunit, ovalbumin, Flt2L, sirolimus and/or anti-thymocyte globulin, CTLA-4/Ig, and mixtures thereof. See, e.g., Viney et al. (1998) J. Immunol. 160(12):5815-25; Horwitz et al. (2004) Seminars in Immunol. 16:135-143; Daniel et al. (2007) J. Immnol. 178(2): 458-68; Weiner et al. (2011) Immunol Rev. 241(1):241-259; Ma et al. (2011) Int. Immunopharmacol. 11(5):618-29; Adriouch et al. (2011) Front. Microbiol. 2:199; Dons et al. (2012) Human Immunol. 73:328-334. The one or more enhancers may, for example, include a sphingosine kinase 1 inhibitor as disclosed in U.S. Pat. No. 8,872,888.

The compound may be a peptide. The peptide may be an S-antigen peptide such as a human S-antigen peptide. The peptide may be an HLA-B27 peptide such as HLA-B27PD (SEQ ID NO: 4). In a particular embodiment, the peptide is a fragment of S-antigen such as VTVDVTNNTEKTVKK (SEQ ID NO: 3) or GEPIPVTVDVTNNTEKTVKK (SEQ ID NO: 2). In another embodiment, the peptide that is utilized in the expansion and/or conditioning of T-reg cells is a fragment of S-antigen such as VTVDVTNNTEKTVKK (SEQ ID NO: 3) or GEPIPVTVDVTNNTEKTVKK (SEQ ID NO: 3). One or more such compounds, such as any of the peptides disclosed herein, may be used alone or in combination in any of the methods set forth herein. In various embodiments, the compound is administered to the patient in a dose of at least 0.025 mg/kg of body weight, at least 0.05 mg/kg of body weight, at least about 0.1 mg/kg of body weight, at least about 0.2 mg/kg of body weight, at least about 0.3 mg/kg of body weight, at least about 0.4 mg/kg of body weight, at least about 0.5 mg/kg of body weight, at least about 0.6 mg/kg of body weight, at least about 0.7 mg/kg of body weight, at least about 0.8 mg/kg of body weight, at least about 0.9 mg/kg of body weight, at least about 1 mg/kg of body weight, at least about 1.5 mg/kg of body weight, at least about 2 mg/kg of body weight, at least about 2.5 mg/kg of body weight, at least about 3 mg/kg of body weight, at least about 3.5 mg/kg of body weight, at least about 4 mg/kg of body weight, at least about 4.5 mg/kg of body weight, at least about 5 mg/kg of body weight, or at about one of said doses or at one of said doses. The doses may, for example, be total doses for one day of treatment. In various embodiments, the compound is a fragment of S-antigen such as VTVDVTNNTEKTVKK (SEQ ID NO: 3) or GEPIPVTVDVTNNTEKTVKK (SEQ ID NO: 3) that is administered to a patient, for example, in a dose, such as a daily dose, in the range of 0.05 to 1.0 mg/kg of body weight or 1.0 to 10 mg total.

In certain embodiments, the compound(s) and/or cell therapy is administered with an additional therapeutically active agent. In some embodiments, the second therapeutically active agent is a dietary supplement such as a vitamin, e.g., vitamin A, vitamin C, vitamin E, β-carotene or a mineral, e.g., zinc oxide or copper, or an ω-3 fatty acid. In other embodiments, the second therapeutically active agent is an anti-VEGF drug. In still other embodiments, the second therapeutically active agent is an anti-inflammatory drug, e.g., a corticosteroid. In various embodiments, the second therapeutically active agent is an anti-bacterial agent, an antihelmintic agent or an anti-fungal agent. In certain embodiments, the second therapeutically active agent is an anti-viral agent.

In certain embodiments, the patient has early AMD, characterized by medium drusen (63-125 μm) without pigmentary abnormalities thought to be related to AMD. In other embodiments, the patient has intermediate AMD, characterized by large drusen or with pigmentary abnormalities associated with at least medium drusen. In still other embodiments, the patient has late AMD, characterized by lesions associated with neovascular AMD or geographic atrophy. Drusen, which are yellow or white accumulations of extracellular material that build up between Bruch's membrane and the retinal pigment epithelium of the eye, can be measured by any technique known by the skilled artisan. In certain embodiments, drusen volumes are measured by spectral domain optical coherence tomography (SD-OCT). In other embodiments, the patient has wet AMD which may be associated with choroidal neovascularization (CNV).

In various embodiments, the result obtained by treatment of AMD or uveitis includes cessation and/or slowing of disease progression, for example, progression from early AMD to intermediate AMD, or progression from intermediate AMD to late AMD, or cessation or slowing of progression to wet AMD, or cessation and/or slowing of neovascularization in wet AMD.

7.7. Diagnosis, Prognosis, Monitoring and Kits

In certain embodiments, the present disclosure relates to methods of diagnosing, prognosticating or monitoring of an autoimmune disease and/or the effectiveness of and/or response to treatment of the disease, in a patient. Accordingly, in some embodiments, a patient is diagnosed as having an autoimmune disease by a method comprising one or more of the following steps: (a) measuring a response (RespH) from responder T-cells of a healthy individual and measuring a response (RespP) from responder T-cells of the patient; (b) measuring a response (RegH) from regulatory T-cells of a healthy individual and measuring a response (RegP) from regulatory T-cells of the patient; and (c) measuring a response (RespH) from responder T-cells of a healthy individual, a response (RespP) from responder T-cells of the patient and measuring a response (RegP) from regulatory T-cells of the patient and a response (RespH) from responder T-cells of a healthy individual in the presence of a compound comprising an epitope identified in vitro from a library or collection of compounds that induces immune tolerance in a human patient, wherein a comparison of RespH and RespP, or of RegH and RegP, or of both RespH and RespP, and RegH and RegP that indicates a deviation of the patient's response from that of a healthy individual is indicative of an autoimmune disease in a patient. In other embodiments, a patient is predicted to have an autoimmune disease by a method comprising one or more of the following steps: (a) measuring a response (RespH) from responder T-cells of a healthy individual and measuring a response (RespP) from responder T-cells of the patient; (b) measuring a response (RegH) from regulatory T-cells of a healthy individual and measuring a response (RegP) from regulatory T-cells of the patient; and (c) measuring a response (RespH) from responder T-cells of a healthy individual, a response (RespP) from responder T-cells of the patient and measuring a response (RegP) from regulatory T-cells of the patient and a response (RespH) from responder T-cells of a healthy individual in the presence of a compound comprising an epitope identified in vitro from a library or collection of compounds that induces immune tolerance in a human patient, wherein a comparison of RespH and RespP, or of RegH and RegP, or of both RespH and RespP, and RegH and RegP that indicates a deviation of the patient's response from that of a healthy individual is predictive of an autoimmune disease in a patient. In still other embodiments, a patient suffering from an autoimmune disease is monitored, e.g., to determine the efficacy of a therapy and/or to determine disease progression by a method comprising one or more of the following steps: (a) measuring a response (RespH) from responder T-cells of a healthy individual and measuring a response (RespP) from responder T-cells of the patient; (b) measuring a response (RegH) from regulatory T-cells of a healthy individual and measuring a response (RegP) from regulatory T-cells of the patient; and (c) measuring a response (RespH) from responder T-cells of a healthy individual, a response (RespP) from responder T-cells of the patient and measuring a response (RegP) from regulatory T-cells of the patient and a response (RespH) from responder T-cells of a healthy individual in the presence of a compound comprising an epitope identified in vitro from a library or collection of compounds that induces immune tolerance in a human patient, wherein a comparison of RespH and RespP, or of RegH and RegP, or of both RespH and RespP, and RegH and RegP that indicates a deviation of the patient's response from that of a healthy individual is predictive of disease progression or efficacy of therapy.

The skilled artisan will understand that a RegP response that is greater than or equal to a RegH and/or a RespP that is lower than or equal to a RespH is indicative of the absence of an autoimmune disease in the patient, and/or no predicted autoimmune disease and/or diminishment of or lack of autoimmune disease progression in a patient. Conversely, a RegP response that is less than a RegH response and/or a RespP response that is greater than a RespH response is indicative of the presence of an autoimmune disease in the patient, and/or a predicted autoimmune disease and/or progression of an autoimmune disease in a patient.

Any of the disease assessment/monitoring methods of the invention may be used to evaluate the effectiveness of treatment of autoimmune disease in the mammal or human patient. A baseline assessment of disease may be made for the patient before beginning treatment or a new treatment by measuring the responsiveness of the patient's responder and/or regulatory immune cells to a subject epitope. The evaluation of such treatment may, for example, be conducted at least one, day, at least one week, at least two weeks or at least one month after the treatment (or new treatment) of the autoimmune disease has begun or been administered. The assessment/monitoring may be conducted multiple times, for example, in intervals of a week, two weeks, or 1-12 months such as monthly, every two months, every three months, and so on. The autoimmune disease may, for example, be any of the autoimmune diseases disclosed herein, such as but not limited to age-related macular degeneration, and the treatment for the autoimmune disease may, for example, be any of the pharmaceutical immune tolerizing peptides or cellular therapy compositions disclosed herein, such as but not limited to synthetic Peptide 23 (SEQ ID NO: 3) for the treatment of AMD and preparations of regulatory immune cells trained with Peptide 23 for the treatment of AMD.

Thus, one embodiment of the invention provides a method for monitoring the effectiveness of treatment of an autoimmune disease that comprises the steps of: administering a treatment for an autoimmune disease to a patient in need of treatment for the autoimmune disease; and after the treatment has been administered measuring the responsiveness of the patient's responder and/or regulatory immune cells to a subject epitope. The measuring step may be repeated more than once on different days, for example, at regular intervals. The embodiment may include a further step of before the administering step, measuring the responsiveness of the patient's responder and/or regulatory immune cells to a subject epitope. Changes or a lack thereof and the direction and magnitude of any changes in the immune cells responsiveness parameters set forth herein over the course of treating the subject are indicative of the extent of efficacy or lack thereof of the treatment.

In certain embodiments, the present disclosure relates to kits for diagnosing, prognosticating or monitoring disease and/or its treatment in a patient. In various embodiments, the kits described herein comprise one or more of the following components in any combination: (a) a compound comprising an epitope that induces immune tolerance in a human patient; (b) a buffer; (c) a cell growth medium such as a lymphocyte growth medium such as a T-cell growth medium; (d) regulatory T-cells from a healthy individual; (e) responder T-cells from a healthy individual; and (f) at least one enhancer selected from the group consisting of high molecular weight hyaluronic acid, IL-2, IL-15, TGF-β, all-trans retinoic acid, rapamycin, anti-CD3, anti-CD28, vitamin D3, dexamethasone, IL-10, idolamine-2,3-dioxygenase, FTY720, a sphingosine kinase 1 inhibitor, cholera toxin B subunit, ovalbumin, Flt2L, sirolimus and/or anti-thymocyte globulin, and CTLA-4/Ig.

8. ADDITIONAL EMBODIMENTS

1. This embodiment relates to a method of identifying a compound comprising an epitope that induces immune tolerance in a human patient suffering from an autoimmune disease comprising the step of identifying in vitro a compound from a library or collection of compounds that:
   a. elicits a response (RespH) from responder immune cells, such as responder T-cells, of a healthy individual;
   b. elicits a response (RespP) from responder immune cells, such as responder T-cells, of the patient (e.g., of the same type as in (a.));
   c. elicits a response (RegH) from regulatory immune cells, such as regulatory T-cells, of a healthy individual; and
   d. elicits a response (RegP) from regulatory immune cells, such as regulatory T-cells, of the patient (e.g., of the same type as in (c.)), wherein the compound that induces a RespH/RespP<1, a RegH/RegP≥1 or a RespH/RespP<1 and a RegH/RegP≥1 is identified as the compound that induces an immune tolerance.

2. This embodiment relates to a method of identifying a compound comprising an epitope that induces immune tolerance in a human patient suffering from an autoimmune disease comprising the steps of:
   a. identifying in vitro a compound from a library or collection of compounds that:
      i. elicits a response (RespH) from responder T-cells of a healthy individual; and
      ii. elicits a response (RespP) from responder T-cells of the patient;
   b. determining the total number of T-cells (P1) from the healthy individual that provides an amount of T-reg cells that induces 50% suppression of T-resp activity in the presence of said compound; and
   c. determining the total number of T-cells (P2) from the patient that provides an amount of T-reg cells that induces 50% suppression of said T-resp activity in the presence of said compound;

wherein the compound that induces a RespH/RespP<1, a P1/P2>1 or RespH/RespP<1 and a P1/P2>1 is identified as the compound that induces an immune tolerance.

3. The method of embodiment 2, wherein the T-resp cells of steps (b) and (c) are from a healthy individual.

4. The method of embodiment 2, wherein the T-resp cells of steps (b) and (c) are from a patient suffering from an autoimmune disease 5. The method of embodiment 1 or embodiment 2, wherein the epitope is a self-epitope.

6. The method of embodiment 1 or embodiment 2, wherein the epitope is a non-self epitope.

7. The method of embodiment 1 or embodiment 2, wherein the epitope is organ specific.

8. The method of embodiment 1 or embodiment 2, wherein the epitope is not organ specific.

9. The method of embodiment 1 or embodiment 2, wherein the epitope is selected from the group consisting of a human epitope, a non-human mammalian epitope, a bacterial epitope, a viral epitope, and a mixture thereof.

10. The method of embodiment 1 or embodiment 2, wherein the library is a library of biological epitopes.

11. The method of embodiment 10, wherein the library is a library of HLA epitopes, such as human HLA epitopes.

12. The method of embodiment 10, wherein the library is a library of HLA variant epitopes.

13. The method of embodiment 11, wherein the library is a library of HLA-B27 epitopes.

14. The method of embodiment 10, wherein the library is a library of S-antigen epitopes, such as human S-antigen epitopes.

15. The method of embodiment 1 or embodiment 2, wherein the collection includes all permutations of epitope pentamers.

16. The method of embodiment 1 or embodiment 2, wherein the collection includes all permutations of epitope tetramers.

17. The method of embodiment 10, wherein the library is a library of self biological epitopes.

18. The method of embodiment 10, wherein the library is a library of non-self biological epitopes.

19. The method of embodiment 10, wherein the library is a library of self and non-self biological epitopes.

20. The method of embodiment 1 or embodiment 2, wherein the responder cells are (or are substituted with) cells selected from the group consisting of $CD8^+$ cells, $CD4^+$ T-cells, naïve $CD4^+CD25^+$ T-cells, NK cells, cytotoxic T lymphocytes, mature dendritic cells and mixtures thereof.

21. The method of embodiment 1 or embodiment 2, wherein the regulatory cells are (or are substituted with) cells selected from the group consisting of $CD4^+CD25^+$ T-cells, $CD4^+Foxp3^+$ T-cells, $CD4^+CD25^+Foxp3^+$ T-cells, $CD4^+$ Tr1 T-cells, Th3 T-cells, s $CD8^+$ NKT-cells, $CD4^-CD8^+$ T-cells, γδ T-cells, nT-reg cells, i-Treg cells, tolerogenic dendritic cells, $CD4^+CD127^{lo/-}$ T-cells, $CD4^+CD127^{lo/-}CD25^+$ T-cells, $CD45RA^+CD4^+CD127^{lo/-}CD25^+$ T-cells and mixtures thereof.

22. The method of embodiment 1 or embodiment 2, wherein the response of the responder cells is cell proliferation.

23. The method of embodiment 1 or embodiment 2, wherein the response of the regulatory cells is cell proliferation.

24. The method of embodiment 5, which is done in the presence of an enhancer of immune tolerance.

25. The method of embodiment 24, wherein the enhancer is selected from high molecular weight hyaluronic acid, IL-2, IL-15, TGF-β, all-trans retinoic acid, rapamycin, anti-CD3, anti-CD28, vitamin D3, dexamethasone, IL-10, idolamine-2,3-dioxygenase, FTY720, a sphingosine kinase 1 inhibitor, cholera toxin B subunit, ovalbumin, Flt2L, sirolimus and/or anti-thymocyte globulin, CTLA-4/Ig, and mixtures thereof.

26. The method of embodiment 1 or embodiment 2, wherein the autoimmune disease is selected from the group consisting of acute disseminated encephalomyelitis, Addison's disease, agammaglobulinemia, age-related macular degeneration, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behcet's disease, Berger's disease, Bickerstaff's encephalitis, Blau syndrome, Bullous pemphigoid, cancer, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressiva, fibrosing alveolitis, gastritis, gastrointestinal pemphigoid, glomerulonephritis, Goodpasture's syndrome, Graves' disease, Guillan-Barré syndrome, Hashimoto's encephalopathy, Hashimoto's thyroiditis, Henoch-Schonlein purpura, gestational pemphigoid, hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease, lupus erythematosus, Majeed syndrome, Meniere's disease, microscopic polyangiitis, mixed connective tissue disease, morphea, Mucha-Habermann disease, multiple sclerosis, myasthenia gravis, myositis, narcolepsy, neuromyelitis optica, neuromyotonia, occular cicatricial pemphigoid, opsoclonus myoclonus syndrome, Ord's thyroiditis, palindromic rheumatism, pediatric autoimmune neuropsychiatric disorders associated with streptococcus, paraneoplastic cerebellar degeneration, paroxysmal nocturnal hemoglobinuria, Parry Romberg syndrome, Parsonage-Turner syndrome, Pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome, Schnitzler syndrome, scleritis, scleroderma, serum sickness, Sjögren's syndrome, spondyloarthropathy, stiff person syndrome, subacute bacterial endocarditis, Susac's syndrome, Sweet's syndrome, sympathetic ophthalmia, Takayasu's arteritis, temporal arteritis, thrombocytopenia, Tolosa-Hunt syndrome, transverse myelitis, ulcerative colitis, undifferentiated connective tissue disease, urticarial vasculitis, vasculitis, vitiligo and Wegener's granulomatosis.

27. The method of embodiment 26, wherein the autoimmune disease is selected from the group consisting of acute disseminated encephalomyelitis, age-related macular degeneration, alopecia areata, ankylosing spondylitis, antiphospholipid syndrome, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Behcet's disease, celiac disease, Chagas disease, chronic obstructive pulmonary disease, cold agglutinin disease, Crohn's disease, Dercum's disease, dermatomyositis, diabetes mellitus type 1, endometriosis, eosinophilic gastroenteritis, gastrointestinal pemphigoid, glomerulonephritis, Goodpasture's syndrome, Graves' disease, Guillan-Barré syndrome, Hashimoto's encephalopathy, Hashimoto's thyroiditis, hidradenitis suppurativa, idiopathic thrombocytopenic purpura, interstitial cystitis, Kawasaki's disease, lupus erythematosus, mixed connective tissues disease, morphea, multiple sclerosis, myasthenia gravis, narcolepsy, neuromyotonia, opsoclonus myoclonus syndrome, pediatric autoimmune neuropsychiatric disorders associated with streptococcus, paroxysmal nocturnal hemoglobinuria, pemphigus vulgaris, pernicious anaemia, polymyositis, primary biliary cirrhosis, progressive inflammatory neuropathy, psoriasis, psoriatic arthritis, Renaud phenomenon, relapsing polychondritis, restless leg syndrome, rheumatoid arthritis, rheumatic fever, sarcoidosis, schizophrenia, scleroderma, Sjögren's syndrome, stiff person syndrome, temporal arteritis, transverse myelitis, ulcerative colitis, undifferentiated connective tissue disease, vasculitis, vitiligo, and Wegener's granulomatosis.

28. This embodiment relates to a method of identifying a compound comprising an epitope that induces immune tolerance in a human patient suffering from an autoimmune disease comprising the steps of identifying in vitro a compound from a library or collection of compounds that
   i. elicits a response ($RespP_1$) from responder immune cells, such as responder T-cells, of the patient; and
   ii. elicits a response (RespH) from responder immune cells, such as responder T-cells, of a healthy individual (of the same type as in (i.))
   wherein $RespP_1/RespH>1$ and
   iii. elicits a response ($RespP_2$) from responder immune cells, such as responder T-cells, of the patient in the presence of a responder immune cell antigen and regulatory immune cells, such as in the presence of a responder T-cell antigen and regulatory T-cells, wherein $RespP_2/RespP_1<1$,
wherein the compound that induces a $RespP_1/RespH>1$ and $RespP_2/RespP_1<1$ is identified as a compound that induces an immune tolerance or a candidate therefor.

29. The method of embodiment 28, wherein the epitope is a self-epitope.

30. The method of embodiment 28, wherein the epitope is a non-self epitope.

31. The method of embodiment 28, wherein the epitope is organ specific.

32. The method of embodiment 28, wherein the epitope is not organ specific.

33. The method of embodiment 28, wherein the epitope is selected from the group consisting of a human epitope, a non-human mammalian epitope, a bacterial epitope, a viral epitope, and a mixture thereof.

34. The method of embodiment 28, wherein the library is a library of biological epitopes.

35. The method of embodiment 34, wherein the library is a library of HLA epitopes.

36. The method of embodiment 35, wherein the library is a library of HLA variant epitopes.

37. The method of embodiment 36, wherein the library is a library of HLA-B27 epitopes.

38. The method of embodiment 34, wherein the library is a library of S-antigen epitopes.

39. The method of embodiment 28, wherein the collection includes all permutations of epitope pentamers.

40. The method of embodiment 28, wherein the collection includes all permutations of epitope tetramers.

41. The method of embodiment 34, wherein the library is a library of self biological epitopes.

42. The method of embodiment 34, wherein the library is a library of non-self biological epitopes.

43. The method of embodiment 34, wherein the library is a library of self and non-self biological epitopes.

44. The method of embodiment 28, wherein the responder cells are selected from the group consisting of $CD8^+$ cells, $CD4^+$ T-cells, naïve $CD4^+CD25^+$ T-cells, NK cells, cytotoxic T lymphocytes, mature dendritic cells and mixtures thereof.

45. The method of embodiment 28, wherein the regulatory are selected from the group consisting of $CD4^+CD25^+$ T-cells, $CD4^+Foxp3^+$ T-cells, $CD4^+CD25^+Foxp3^+$ T-cells, $CD4^+$ Tr1 T-cells, Th3 T-cells, $CD8^+$ NKT-cells, $CD4^-CD8^+$ T-cells, $\gamma\delta$ T-cells, nT-reg cells, i-Treg cells, tolerogenic dendritic cells, $CD4^+CD127^{lo/-}$ T-cells, $CD4^+CD127^{lo/-}CD25^+$ T-cells, $CD45RA^+CD4^+CD127^{lo/-}CD25^+$ T-cells and mixtures thereof.

46. The method of embodiment 28, wherein the response of the responder cells is cell proliferation.

47. The method of embodiment 28, wherein the response of the responder cells is cytokine secretion.

48. The method of embodiment 28, wherein the autoimmune disease is selected from the group consisting of acute disseminated encephalomyelitis, Addison's disease, agammaglobulinemia, age-related macular degeneration, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behcet's disease, Berger's disease, Bickerstaff s encephalitis, Blau syndrome, Bullous pemphigoid, cancer, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis, gastritis, gastrointestinal pemphigoid, glomerulonephritis, Goodpasture's syndrome, Graves' disease, Guillan-Barré syndrome, Hashimoto's encephalopathy, Hashimoto's thyroiditis, Henoch-Schonlein purpura, gestational pemphigoid, hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease, lupus erythematosus, Majeed syndrome, Meniere's disease, microscopic polyangiitis, mixed connective tissue disease, morphea, Mucha-Habermann disease, multiple sclerosis, myasthenia gravis, myositis, narcolepsy, neuromyelitis optica, neuromyotonia, occular cicatricial pemphigoid, opsoclonus myoclonus syndrome, Ord's thyroiditis, palindromic rheumatism, pediatric autoimmune neuropsychiatric disorders associated with streptococcus, paraneoplastic cerebellar degeneration, paroxysmal nocturnal hemoglobinuria, Parry Romberg syndrome, Parsonage-Turner syndrome, Pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome, Schnitzler syndrome, scleritis, scleroderma, serum sickness, Sjögren's syndrome, spondyloarthropathy, stiff person syndrome, subacute bacterial endocarditis, Susac's syndrome, Sweet's syndrome, sympathetic ophthalmia, Takayasu's arteritis, temporal arteritis, thrombocytopenia, Tolosa-Hunt syndrome, transverse myelitis, ulcerative colitis, undifferentiated connective tissue disease, urticarial vasculitis, vasculitis, vitiligo and Wegener's granulomatosis.

49. The method of embodiment 28, wherein the autoimmune disease is selected from the group consisting of acute disseminated encephalomyelitis, age-related macular degeneration, alopecia areata, ankylosing spondylitis, antiphospholipid syndrome, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Behcet's disease, celiac disease, Chagas disease, chronic obstructive pulmonary disease, cold agglutinin disease, Crohn's disease, Dercum's disease, dermatomyositis, diabetes mellitus type 1, endometriosis, eosinophilic gastroenteritis, gastrointestinal pemphigoid, glomerulonephritis, Goodpasture's syndrome, Graves' disease, Guillan-Barré syndrome, Hashimoto's encephalopathy, Hashimoto's thyroiditis, hidradenitis suppurativa, idiopathic thrombocytopenic purpura, interstitial cystitis, Kawasaki's disease, lupus erythematosus, mixed connective tissues disease, morphea, multiple sclerosis, myasthenia gravis, narcolepsy, neuromyotonia, opsoclonus myoclonus syndrome, pediatric autoimmune neuropsychiatric disorders associated with streptococcus, paroxysmal nocturnal hemoglobinuria, pemphigus vulgaris, pernicious anaemia, polymyositis, primary biliary cirrhosis, progressive inflammatory neuropathy, psoriasis, psoriatic arthritis, Renaud phenomenon, relapsing polychondritis, restless leg syndrome, rheumatoid arthritis, rheumatic fever, sarcoidosis, schizophrenia, scleroderma, Sjögren's syndrome, stiff person syndrome, temporal arteritis, transverse myelitis, ulcerative colitis, undifferentiated connective tissue disease, vasculitis, vitiligo, and Wegener's granulomatosis.

50. A method of identifying a compound comprising an epitope from a library or collection of compounds that induces immune tolerance in a human patient suffering from an autoimmune disease comprising the steps of:
   a. exposing human $CD4^+CD25^+$ cells to a compound from a library or collection of compounds; and
   b. measuring a response ($R_1$) of said $CD4^+CD25^+$ cells in the presence of the compound; and
   c. measuring a response ($R_2$) of said $CD4^+CD25^+$ cells in the absence of the compound,
   wherein the compound that induces $R_1/R_2 > 1$ is identified as a/the compound that induces immune tolerance or a candidate therefor.

51. The method of embodiment 50, which further comprises before step (a) a step of isolating the $CD4^+CD25^+$ cells.

52. The method of embodiment 50, wherein step (b) is carried out with said cells in the presence of the compound.

53. The method of embodiment 50, wherein step (b) is carried out with said cells after removal of the compound.

54. The method of embodiment 50, wherein the response is cell proliferation.

55. The method of embodiment 54, wherein said cell proliferation is measured by incorporation of $^3H$ or by monitoring decreases in fluorescence.

56. The method of embodiment 50, wherein the response is cytokine production.

57. The method of embodiment 56, wherein the cytokine is TGF-β.

58. The method of embodiment 50, which is performed in the presence of an additional agent selected from 11-2, rapamycin, CD3 and CD28.

59. The method of embodiment 50, wherein the $CD4^+CD25^+$ cells are from a healthy individual.

60. The method of embodiment 50, wherein the epitope is a self-epitope.

61. The method of embodiment 50, wherein the epitope is a non-self epitope.

62. The method of embodiment 50, wherein the epitope is organ specific.

63. The method of embodiment 50, wherein the epitope is not organ specific.

64. The method of embodiment 50, wherein the epitope is selected from the group consisting of a human epitope, a non-human mammalian epitope, a bacterial epitope, a viral epitope, and a mixture thereof.

65. The method of embodiment 50, wherein the library is a library of biological epitopes.

66. The method of embodiment 65, wherein the library is a library of HLA epitopes.

67. The method of embodiment 66, wherein the library is a library of HLA variant epitopes.

68. The method of embodiment 67, wherein the library is a library of HLA-B27 epitopes.

69. The method of embodiment 65, wherein the library is a library of S-antigen epitopes, such as human S-antigen epitopes.

70. The method of embodiment 50, wherein the collection includes at least substantially or all permutations of epitope pentamers, for example, for peptides, at least substantially all or all permutations of 5 amino acids.

71. The method of embodiment 50, wherein the collection includes all permutations of epitope tetramers for example, for peptides, at least substantially all or all permutations of 4 amino acids.

72. The method of embodiment 65, wherein the library is a library of self biological epitopes.

73. The method of embodiment 65, wherein the library is a library of non-self biological epitopes.

74. The method of embodiment 65, wherein the library is a library of self and non-self biological epitopes.

75. The method of embodiment 50, which is done in the presence of an enhancer of immune tolerance.

76. The method of embodiment 75, wherein the enhancer is selected from the group consisting of high molecular weight hyaluronic acid, IL-2, IL-15, TGF-β, all-trans retinoic acid, rapamycin, anti-CD3, anti-CD28, vitamin D3, dexamethasone, IL-10, idolamine-2,3-dioxygenase, FTY720, a sphingosine kinase 1 inhibitor, cholera toxin B subunit, ovalbumin, Flt2L, sirolimus and/or anti-thymocyte globulin, CTLA-4/Ig, and mixtures thereof.

77. The method of embodiment 50, wherein the autoimmune disease is selected from the group consisting of acute disseminated encephalomyelitis, age-related macular degeneration, alopecia areata, ankylosing spondylitis, antiphospholipid syndrome, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Behcet's disease, celiac disease, Chagas disease, chronic obstructive pulmonary disease, cold agglutinin disease, Crohn's disease, Dercum's disease, dermatomyositis, diabetes mellitus type 1, endometriosis, eosinophilic gastroenteritis, gastrointestinal pemphigoid, glomerulonephritis, Goodpasture's syndrome, Graves' disease, Guillan-Barré syndrome, Hashimoto's encephalopathy, Hashimoto's thyroiditis, hidradenitis suppurativa, idiopathic thrombocytopenic purpura, interstitial cystitis, Kawasaki's disease, lupus erythematosus, mixed connective tissues disease, morphea, multiple sclerosis, myasthenia gravis, narcolepsy, neuromyotonia, opsoclonus myoclonus syndrome, pediatric autoimmune neuropsychiatric disorders associated with streptococcus, paroxysmal nocturnal hemoglobinuria, pemphigus vulgaris, pernicious anaemia, polymyositis, primary biliary cirrhosis, progressive inflammatory neuropathy, psoriasis, psoriatic arthritis, Renaud phenomenon, relapsing polychondritis, restless leg syndrome, rheumatoid arthritis, rheumatic fever, sarcoidosis, schizophrenia, scleroderma, Sjögren's syndrome, stiff person syndrome, temporal arteritis, transverse myelitis, ulcerative colitis, undifferentiated connective tissue disease, vasculitis, vitiligo, and Wegener's granulomatosis.

78. A method of identifying a compound comprising an epitope that induces immune tolerance in a human patient suffering from an autoimmune disease comprising the step of identifying in vitro a compound that elicits a response from responder immune cells, such as responder T-cells, from a patient in the presence of regulatory immune cells, such as regulatory T-cells, of the patient that is greater than, such as but not limited to at least 1.5 times, at least 2.5 times, or at least 3.0 times, the response elicited from the regulatory immune cells, such as the regulatory T-cells, of the patient.

79. A method of identifying a compound comprising an epitope that induces immune tolerance in a human patient suffering from an autoimmune disease comprising the step of identifying in vitro a compound that elicits a response from regulatory immune cells, such as regulatory T-cells, from a healthy individual in the presence of responder immune cells, such as responder T-cells, from the patient that is greater than, such as but not limited to at least 1.5 times, at least 2.5 times, or at least 3.0 times, the response elicited from the responder immune cells, such as the responder T-cells, of the patient.

80. A method of identifying a compound comprising an epitope that induces immune tolerance in a human patient suffering from an autoimmune disease comprising the step of identifying in vivo a compound that elicits a response from responder immune cells, such as responder T-cells, from a healthy individual in the presence of regulatory immune cells, such as regulatory T-cells, from the patient that is greater than, such as but not limited to at least 1.5 times, at least 2.5 times, or at least 3.0 times, the response elicited from the regulatory immune cells, such as the regulatory T-cells, from the patient.

81. A method of identifying a compound comprising an epitope that induces immune tolerance in a human patient suffering from an autoimmune disease comprising the step of identifying in vitro a compound that elicits a response from a responder immune cell (or cells), such as a responder T-cell (or cells), of a healthy individual in the presence of a regulatory immune cell (or cells), such as a regulatory T-cell (or cells) from the healthy individual, wherein the response from the responder immune cell (or cells), such as the responder T-cell (or cells) of the healthy individual is less than the response from the regulatory immune cells, such as the regulatory T-cells, for example, less by at least 33%, less by at least 50%, less by at least 70%, less by at least 80% or less by at least 90%.

82. A method of identifying a compound comprising an epitope that induces immune tolerance in a human patient suffering from an autoimmune disease comprising the step of identifying in vitro a compound from a library or collection of compounds that
   a. elicits a response (RespH) from responder immune cells, such as responder T-cells, of a healthy individual, and
   b. elicits a response (RespP) from responder immune cells, such as responder T-cells, of the patient (e.g. of the same type as in (a.)),
   wherein the compound that induces a RespH/RespP<1 is identified as a/the compound that induces immune tolerance or a candidate therefor.

83. The method of embodiment 82, wherein the epitope is a self-epitope.

84. The method of embodiment 82, wherein the epitope is a non-self epitope.

85. The method of embodiment 82, wherein the epitope is organ specific.

86. The method of embodiment 82, wherein the epitope is not organ specific.

87. The method of embodiment 82, wherein the epitope is selected from the group consisting of a human epitope, a non-human mammalian epitope, a bacterial epitope, a viral epitope, and a mixture thereof.

88. The method of embodiment 82, wherein the library is a library of biological epitopes.

89. The method of embodiment 88, wherein the library is a library of HLA epitopes.

90. The method of embodiment 85, wherein the library is a library of HLA variant epitopes.

91. The method of embodiment 90, wherein the library is a library of HLA-B27 epitopes.

92. The method of embodiment 88, wherein the library is a library of S-antigen epitopes.

93. The method of embodiment 82, wherein the collection includes at least substantially or all permutations of epitope pentamers, for example, for peptides, at least substantially all or all permutations of 5 amino acids.

94. The method of embodiment 82, wherein the collection includes at least substantially or all permutations of epitope tetramers, for example, for peptides, at least substantially all or all permutations of 4 amino acids.

95. The method of embodiment 88, wherein the library is a library of self biological epitopes.

96. The method of embodiment 88, wherein the library is a library of non-self biological epitopes.

97. The method of embodiment 88, wherein the library is a library of self and non-self biological epitopes.

98. The method of embodiment 82, wherein the responder cells are selected from the group consisting of $CD8^+$ cells, $CD4^+$ T-cells, naïve $CD4^+CD25^+$ T-cells, NK cells, cytotoxic T lymphocytes, mature dendritic cells and mixtures thereof.

99. The method of embodiment 82, wherein the response of the responder T-cells is cell proliferation.

100. The method of embodiment 87, wherein the compound comprises a human epitope.

101. The method of embodiment 100, wherein the compound comprises an epitope of human S-antigen.

102. The method of embodiment 101, wherein the compound is a peptide including or consisting of the sequence of GEPIPVTVDVTNNTEKTVKK (SEQ ID NO: 2) or the sequence VTVDVTNNTEKTVKK (SEQ ID NO: 3).

103. The method of embodiment 82, which is done in the presence of an enhancer of immune tolerance.

104. The method of embodiment 103, wherein the enhancer is selected from the group consisting of high molecular weight hyaluronic acid, IL-2, IL-15, TGF-β, all-trans retinoic acid, rapamycin, anti-CD3, anti-CD28, vitamin D3, dexamethasone, IL-10, idolamine-2,3-dioxygenase, FTY720, a sphingosine kinase 1 inhibitor, cholera toxin B subunit, ovalbumin, Flt2L, sirolimus and/or anti-thymocyte globulin, CTLA-4/Ig, and mixtures thereof.

105. A method of identifying a compound that induces immune tolerance in a human patient suffering from age-related macular degeneration or uveitis from a library or collection of compounds comprising the step of
   a. identifying in vitro a compound from a library or collection of compounds that induces a response from a responder immune cell (or cells), such as a responder T-cell (or cells), of the patient that is greater than a response from a responder immune cell (or cells), such as a responder T-cell (or cells) of a healthy individual, wherein the compound that induces a response from the responder immune cell (or cells), such as the responder T-cell (or cells) of the patient that is greater than the response from the responder immune cell (or cells), such as the responder T-cell (or cells) of the healthy individual is identified as a/the compound that induces immune tolerance in the patient or a candidate therefor.

106. A method of identifying a compound that induces immune tolerance in a human patient suffering from age-related macular degeneration or uveitis from a library or collection of compounds comprising the step of identifying a compound that induces a response from a regulatory immune cell (or cells), such as a regulatory T-cell (or cells), of a healthy individual that is greater than a response from a regulatory immune cell (or cells), such as a regulatory T-cell (or cells) of the patient, wherein the compound that induces a response from the regulatory immune cell (or cells), such as the regulatory T-cell (or cells) of the healthy individual that is greater than the response from the regulatory immune cell (or cells), such as the regulatory T-cell (or cells) of the patient is identified as a/the compound that induces immune tolerance in the patient or a candidate therefor.

107. A method of treating age-related macular degeneration or uveitis in a patient comprising administering to the patient an effective amount of a compound comprising an epitope that induces immune tolerance comprising the step of administering a compound identified in vitro from a library or collection of compounds, wherein the compound
 a. elicits a response (RespH) from responder immune cells, such as responder T-cells, of a healthy individual and
 b. elicits a response (RespP) from responder immune cells, such as responder T-cells, of the patient (RespP), and
 wherein the compound induces a RespH/RespP<1.

108. The method of embodiment 107, wherein the compound comprises a human epitope.

109. The method of embodiment 108, wherein the human epitope is from human S-antigen.

110. The method of embodiment 109, wherein the compound is a peptide including or consisting of the sequence GEPIPVTVDVTNNTEKTVKK (SEQ ID NO: 2) or the sequence VTVDVTNNTEKTVKK (SEQ ID NO: 3).

111. The method of embodiment 107, which is performed in the presence of an enhancer of immune tolerance.

112. The method of embodiment 111, wherein the enhancer is selected from the group consisting of high molecular weight hyaluronic acid, IL-2, IL-15, TGF-β, all-trans retinoic acid, rapamycin, anti-CD3, anti-CD28, vitamin D3, dexamethasone, IL-10, idolamine-2,3-dioxygenase, FTY720, a sphingosine kinase 1 inhibitor, cholera toxin B subunit, ovalbumin, Flt2L, sirolimus and/or anti-thymocyte globulin, CTLA-4/Ig, and mixtures thereof.

113. The method of embodiment 107, further comprising a step of administering a therapeutic agent selected from the group consisting of a vitamin, a mineral, an ω-3 fatty acid, an anti-VEGF drug, an anti-inflammatory drug, and mixtures thereof.

114. A method of treating a human patient suffering from an autoimmune disease comprising administering to the patient and effective amount of regulatory T-cells trained in the presence of a compound comprising an epitope that induces immune tolerance, wherein the compound is identified from a library or collection of compounds, wherein the compound
 i. elicits a response (RespH) from responder immune cells, such as responder T-cells, of a healthy individual;
 ii. elicits a response (RespP) from responder immune cells, such as responder T-cells, of the patient;
 iii. elicits a response (RegH) from regulatory immune cells, such as regulatory T-cells, of a healthy individual; and
 iv. elicits a response (RegP) from regulatory immune cells, such as regulatory T-cells of the patient, and
 wherein the compound induces a RespH/RespP<1 and a RegH/RegP≥1.

115. The method of embodiment 114, wherein the regulatory immune cells are not expanded.

116. The method of embodiment 114, wherein the regulatory immune cells are expanded.

117. The method of embodiment 116, wherein the regulatory immune cells are expanded in vitro in the presence of the compound.

118. The method of embodiment 116, wherein the regulatory immune cells are expanded in vivo in the presence of the compound.

119. The method of embodiment 114, wherein the regulatory immune cells are autologous to the patient.

120. The method of embodiment 114, wherein the regulatory immune cells are heterologous to and compatible with the patient.

121. The method of embodiment 114, which is performed in the presence of an enhancer of immune tolerance.

122. The method of embodiment 114, wherein the enhancer is selected from the group consisting of high molecular weight hyaluronic acid, IL-2, IL-15, TGF-β, all-trans retinoic acid, rapamycin, anti-CD3, anti-CD28, vitamin D3, dexamethasone, IL-10, idolamine-2,3-dioxygenase, FTY720, a sphingosine kinase 1 inhibitor, cholera toxin B subunit, ovalbumin, Flt2L, sirolimus and/or anti-thymocyte globulin, CTLA-4/Ig, and mixtures thereof.

123. The method of embodiment 114, wherein the autoimmune disease is selected from the group consisting of acute disseminated encephalomyelitis, Addison's disease, agammaglobulinemia, age-related macular degeneration, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behcet's disease, Berger's disease, Bickerstaff's encephalitis, Blau syndrome, Bullous pemphigoid, cancer, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis, gastritis, gastrointestinal pemphigoid, glomerulonephritis, Goodpasture's syndrome, Graves' disease, Guillan-Barré syndrome, Hashimoto's encephalopathy, Hashimoto's thyroiditis, Henoch-Schonlein purpura, gestational pemphigoid, hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease, lupus erythematosus, Majeed syndrome, Meniere's disease, microscopic polyangiitis, mixed connective tissue disease, morphea, Mucha-Habermann disease, multiple sclerosis, myasthenia gravis, myositis, narcolepsy, neuromyelitis optica, neuromyotonia, occular cicatricial pemphigoid, opsoclonus myoclonus syndrome, Ord's thyroiditis, palindromic rheumatism, pediatric autoimmune neuropsychiatric disorders associated with streptococcus, paraneoplastic cerebellar degeneration, paroxysmal nocturnal hemoglobinuria, Parry Romberg syndrome, Parsonage-Turner syndrome, Pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome, Schnitzler syndrome, scleritis, scleroderma, serum sickness, Sjögren's syndrome, spondyloarthropathy, stiff person syndrome, subacute bacterial endocarditis, Susac's syndrome, Sweet's syndrome, sympathetic ophthalmia, Takayasu's arteritis, temporal arteritis, thrombocytopenia, Tolosa-Hunt syndrome, transverse myelitis, ulcerative colitis, undifferentiated connective tissue disease, urticarial vasculitis, vasculitis, vitiligo and Wegener's granulomatosis.

124. The method of embodiment 114, wherein the autoimmune disease is selected from the group consisting of acute disseminated encephalomyelitis, age-related macular degeneration, alopecia areata, ankylosing spondylitis, antiphospholipid syndrome, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Behcet's disease, celiac disease, Chagas disease, chronic obstructive pulmonary disease, cold agglutinin disease, Crohn's disease, Dercum's disease, dermatomyositis, diabetes mellitus type 1, endometriosis, eosinophilic gastroenteritis, gastrointestinal pemphigoid, glomerulonephritis, Goodpasture's syndrome, Graves' disease, Guillan-Barré syndrome, Hashimoto's encephalopathy, Hashimoto's thyroiditis, hidradenitis suppurativa, idiopathic thrombocytopenic purpura, interstitial cystitis, Kawasaki's disease, lupus erythematosus, mixed connective tissues disease, morphea, multiple sclerosis, myasthenia gravis, narcolepsy, neuromyotonia, opsoclonus myoclonus syndrome, pediatric autoimmune neuropsychiatric disorders associated with streptococcus, paroxysmal nocturnal hemoglobinuria, pemphigus vulgaris, pernicious anaemia, polymyositis, primary biliary cirrhosis, progressive inflammatory neuropathy, psoriasis, psoriatic arthritis, Renaud phenomenon, relapsing polychondritis, restless leg syndrome, rheumatoid arthritis, rheumatic fever, sarcoidosis, schizophrenia, scleroderma, Sjögren's syndrome, stiff person syndrome, temporal arteritis, transverse myelitis, ulcerative colitis, undifferentiated connective tissue disease, vasculitis, vitiligo, and Wegener's granulomatosis 125. A method of treating a human patient suffering from an autoimmune disease comprising administering to the patient
  a. an effective amount of regulatory immune cells, such as regulatory T-cells; and
  b. an effective amount of a compound comprising an epitope that induces immune tolerance.

126. A method of treating a human patient suffering from an autoimmune disease comprising administering to the patient
  a. an effective amount of regulatory immune cells, such as regulatory T-cells; and
  b. an effective amount of a compound comprising an epitope that induces immune tolerance, wherein the compound is identified from a library or collection of compounds, wherein the compound
    i. elicits a response from a responder immune cell (or cells), such as a responder T-cell (or cells), of a healthy individual (RespH);
    ii. elicits a response from a responder immune cell (or cells), such as a responder T-cell (or cells), of the patient (RespP);
    iii. elicits a response from an immune regulatory cell (or cells), such as a regulatory T-cell (or cells), of a healthy individual (RegH);
    iv. elicits a response from an immune regulatory cell (or cells), such as a regulatory T-cell (or cells), of the patient (RegP), and
  wherein the compound induces a RespH/RespP<1 and a RegH/RegP≥1.

127. The method of embodiment 125, wherein the regulatory immune cells administered in step (a) are trained in the presence of a compound comprising an epitope that induces immune tolerance, wherein the compound is identified from a library or collection of compounds, wherein the compound
  i. elicits a response (RespH) from responder immune cells, such as responder T-cells, of a healthy individual;
  ii. elicits a response (RespP) from responder immune cells, such as responder T-cells, of the patient;
  iii. elicits a response (RegH) from regulatory immune cells, such as regulatory T-cells, of a healthy individual;
  iv. elicits a response (RegP) from regulatory immune cells, such as regulatory T-cells, of the patient, and
  wherein the compound induces a RespH/RespP<1 and a RegH/RegP≥1.

128. The method of embodiment 127, wherein the regulatory immune cells are trained in vitro before administration to the patient.

129. The method of embodiment 127, wherein the regulatory immune cells are trained in vivo after administration to the patient.

130. The method of embodiment 127, wherein the regulatory immune cells are expanded.

131. A method of treating a human patient suffering from an autoimmune disease comprising administering to the patient
  a. an effective amount of regulatory immune cells, such as regulatory T-cells, trained in the presence of a compound comprising an epitope that induces immune tolerance, wherein the compound is identified from a library or collection of compounds, wherein the compound:
    i. elicits a response (RespH) from responder immune cells, such as, responder T-cells, of a healthy individual;
    ii. elicits a response (RespP) from responder immune cells, such as responder T-cells, of the patient (e.g., of the same type as in (i.));
    iii. ii. elicits a response (RegH) from regulatory immune cells, such as regulatory T-cells, of a healthy individual;
    iv. elicits a response (RegP) from regulatory immune cells, such as regulatory T-cells, of the patient (e.g., of the same type as in (i.), and wherein the compound induces a RespH/RespP<1 and a RegH/RegP≥1; and
  b. an effective amount of a compound comprising an epitope that induces immune tolerance, wherein the compound is identified from a library or collection of compounds, wherein the compound
    i. elicits a response (RespH) from responder immune cells, such as, responder T-cells, of a healthy individual;
    ii. elicits a response (RespP) from responder immune cells, such as, responder T-cells, of the patient (e.g., of the same type as in (i.);
    iii. elicits a response (RegH) from regulatory T-cells of a healthy individual (RegH);
    iv. elicits a (RegP) response from regulatory immune cells, such as regulatory T-cells of the patient (e.g., of the same type as in (iii.)), and
  wherein the compound induces a RespH/RespP<1 and a RegH/RegP≥1.

132. The method of embodiment 131, wherein the compound used to train said regulatory T-cells and the compound administered in step (b) are identical.

133. The method of embodiment 131, wherein the compound used to train said regulatory T-cells in step (a) and the compound administered in step (b) are different.

134. The method of embodiment 131, wherein the epitope is a self-epitope.

135. The method of embodiment 131, wherein the epitope is a non-self epitope.

136. The method of embodiment 131, wherein the epitope is organ specific.

137. The method of embodiment 131, wherein the epitope is not organ specific.

138. The method of embodiment 131, wherein the epitope is selected from the group consisting of a human epitope, a non-human mammalian epitope, a bacterial epitope, a viral epitope, and a mixture thereof.

139. The method of embodiment 131, wherein the library is a library of biological epitopes.

140. The method of embodiment 139, wherein the library is a library of HLA epitopes, such as human HLA-B27 epitopes.

141. The method of embodiment 140, wherein the library is a library of HLA variant epitopes.

142. The method of embodiment 140, wherein the library is a library of HLA-B27 epitopes, such as human HLA-B27 epitopes.

143. The method of embodiment 139, wherein the library is a library of S-antigen epitopes, such as human S-antigen epitopes.

144. The method of embodiment 131, wherein the collection includes all permutations of epitope pentamers.

145. The method of embodiment 131, wherein the collection includes all permutations of epitope tetramers.

146. The method of embodiment 139, wherein the library is a library of self biological epitopes.

147. The method of embodiment 139, wherein the library is a library of non-self biological epitopes.

148. The method of embodiment 139, wherein the library is a library of self and non-self biological epitopes.

149. The method of embodiment 131, wherein the regulatory immune cells are selected from the group consisting of $CD4^+CD25^+$ T-cells, $CD4^+Foxp3^+$ T-cells, $CD4^+CD25^+Foxp3^+$ T-cells, $CD4^+$ Tr1 T-cells, Th3 T-cells, $CD8^+$ NKT-cells, $CD4^-CD8^+$ T-cells, γδ T-cells, nT-reg cells, i-Treg cells, tolerogenic dendritic cells, $CD4^+CD127^{lo/-}$ T-cells, $CD4^+CD127^{lo/-}CD25^+$ T-cells, and $CD45RA^+CD4^+CD127^{lo/-}CD25^+$ T-cells, and mixtures thereof.

150. The method of embodiment 131, wherein the response of the responder immune cells is cell proliferation.

151. The method of embodiment 131, wherein the response of the regulatory immune cells is cell proliferation.

152. The method of embodiment 131, which is done in the presence of an enhancer of immune tolerance.

153. The method of embodiment 152, wherein the enhancer is selected from the group consisting of high molecular weight hyaluronic acid, IL-2, IL-15, TGF-β, all-trans retinoic acid, rapamycin, anti-CD3, anti-CD28, vitamin D3, dexamethasone, IL-10, idolamine-2,3-dioxygenase, FTY720, a sphingosine kinase 1 inhibitor, cholera toxin B subunit, ovalbumin, Flt2L, sirolimus and/or anti-thymocyte globulin, CTLA-4/Ig, and mixtures thereof.

154. The method of embodiment 131, wherein the regulatory immune cells are not expanded.

155. The method of embodiment 131, wherein the regulatory immune cells are expanded.

156. The method of embodiment 155, wherein the regulatory immune cells are expanded in vitro.

157. The method of embodiment 155, wherein the regulatory immune cells are expanded in vivo.

158. The method of embodiment 131, wherein the regulatory immune cells are autologous to the patient.

159. The method of embodiment 131, wherein the regulatory immune cells are heterologous to and compatible with the patient.

160. The method of embodiment 131, wherein step (a) and step (b) are performed concurrently.

161. The method of embodiment 131, wherein step (a) and step (b) are performed consecutively.

162. The method of embodiment 161, wherein step (a) is performed before step (b).

163. The method of embodiment 161, wherein step (b) is performed before step (a).

164. The method of embodiment 163, wherein step (a) is performed to maintain the regulatory immune cells administered in step (b).

165. The method of embodiment 131, wherein the peptide is administered orally, for example, by ingestion.

166. The method of embodiment 131, wherein the peptide is administered by infusion.

167. The method of embodiment 131, wherein the autoimmune disease is selected from the group consisting of acute disseminated encephalomyelitis, Addison's disease, agammaglobulinemia, age-related macular degeneration, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behcet's disease, Berger's disease, Bickerstaff's encephalitis, Blau syndrome, Bullous pemphigoid, cancer, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressiva, fibrosing alveolitis, gastritis, gastrointestinal pemphigoid, glomerulonephritis, Goodpasture's syndrome, Graves' disease, Guillan-Barré syndrome, Hashimoto's encephalopathy, Hashimoto's thyroiditis, Henoch-Schonlein purpura, gestational pemphigoid, hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease, lupus erythematosus, Majeed syndrome, Meniere's disease, microscopic polyangiitis, mixed connective tissue disease, morphea, Mucha-Habermann disease, multiple sclerosis, myasthenia gravis, myositis, narcolepsy, neuromyelitis optica, neuromyotonia, occular cicatricial pemphigoid, opsoclonus myoclonus syndrome, Ord's thyroiditis, palindromic rheumatism, pediatric autoimmune neuropsychiatric disorders associated with streptococcus, paraneoplastic cerebellar degeneration, paroxysmal nocturnal hemoglobinuria, Parry Romberg syndrome, Parsonage-Turner syndrome, Pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome, Schnitzler syndrome, scleritis, scleroderma, serum sickness, Sjögren's syndrome, spondyloarthropathy, stiff person syndrome, subacute bacterial endocarditis, Susac's disease, Sweet's syndrome, sympathetic ophthalmia, Takayasu's arteritis, temporal arteritis, thrombocytopenia, Tolosa-Hunt syndrome, transverse myelitis, ulcerative colitis, undifferentiated connective tissue disease, urticarial vasculitis, vasculitis, vitiligo and Wegener's granulomatosis.

168. The method of embodiment 131, wherein the autoimmune disease is selected from the group consisting of acute disseminated encephalomyelitis, age-related macular degeneration, alopecia areata, ankylosing spondylitis, antiphospholipid syndrome, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Behcet's disease, celiac disease, Chagas disease, chronic obstructive pulmonary disease, cold agglutinin disease, Crohn's disease, Dercum's disease, dermatomyositis, diabetes mellitus type 1, endometriosis, eosinophilic gastroenteritis, gastrointestinal pemphigoid, glomerulonephritis, Goodpasture's syndrome, Graves' disease, Guillan-Barré syndrome, Hashimoto's encephalopathy, Hashimoto's thyroiditis, hidradenitis suppurativa, idiopathic thrombocytopenic purpura, interstitial cystitis, Kawasaki's disease, lupus erythematosus, mixed connective tissues disease, morphea, multiple sclerosis, myasthenia gravis, narcolepsy, neuromyotonia, opsoclonus myoclonus syndrome, pediatric autoimmune neuropsychiatric disorders associated with streptococcus, paroxysmal nocturnal hemoglobinuria, pemphigus vulgaris, pernicious anaemia, polymyositis, primary biliary cirrhosis, progressive inflammatory neuropathy, psoriasis, psoriatic arthritis, Renaud phenomenon, relapsing polychondritis, restless leg syndrome, rheumatoid arthritis, rheumatic fever, sarcoidosis, schizophrenia, scleroderma, Sjögren's syndrome, stiff person syndrome, temporal arteritis, transverse myelitis, ulcerative colitis, undifferentiated connective tissue disease, vasculitis, vitiligo, and Wegener's granulomatosis.

The following further embodiments are also provided.

One embodiment of the invention provides a method for treating age-related macular degeneration (AMD) in a human patient, comprising the steps of:

administering, for example via oral ingestion, to a human patient having age-related macular degeneration a therapeutically effective amount, such as but not limited to 1-100 mg or 1-20 mg, or 1-10 mg or any sub-range or amount therein, of one or more of the following compounds or compositions:

1. a synthetic peptide 15 amino acids to 50 amino acids in length, said peptide including the sequence VTVDVTNNTEKTVKK (SEQ ID NO: 3) or a variant thereof in which one or two amino acids are substituted with a different amino acid;
2. a synthetic peptide which is VTVDVTNNTEKTVKK (SEQ ID NO: 3) or a variant thereof in which a one or two amino acids are substituted with a different amino acid;
3. a synthetic peptide 20 amino acids to 50 amino acids in length, said peptide including the sequence GEPIPVTVDVTNNTEKTVKK (SEQ ID NO: 2) or a variant thereof in which one, two or three amino acids are substituted with a different amino acid;
4. a synthetic peptide which is GEPIPVTVDVTNNTEKTVKK (SEQ ID NO: 2) or a variant thereof in which one, two or three amino acids are substituted with a different amino acid;
5. a synthetic peptide 5-50 amino acids in length, such as 14-20 amino acids in length, such as 15 amino acids in length, which is at least 90% identical to a contiguous sequence of human S-antigen;
6. a synthetic peptide 5-50 amino acids in length, such as 14-20 amino acids in length, such as 15 amino acids in length, which is at least 90% identical to a contiguous sequence of SEQ ID NO: 1 or SEQ ID NO: 11;
7. at least substantially pure recombinant human S-antigen or a recombinant fragment thereof, for example, having a length of at least 40 amino acids, or at least substantially pure non-human mammal (such as bovine, ovine or porcine) recombinant human S-antigen or a recombinant fragment thereof, for example, having a length of at least 40 amino acids;
8. the polypeptide or fragment thereof of item (7.) which includes the sequence VTVDVTNNTEKTVKK (SEQ ID NO: 3) or a variant thereof in which one or two amino acids are substituted with a different amino acid;
9. at least substantially pure recombinant SEQ ID NO: 1 or SEQ ID NO: 11, or a recombinant fragment thereof, for example, having a length of at least 40 amino acids;
10. the polypeptide or fragment thereof of item (7.) which includes the sequence VTVDVTNNTEKTVKK (SEQ ID NO: 3) or a variant thereof in which one or two amino acids are substituted with a different amino acid;
11. a composition including proteolytic fragments of the recombinant polypeptide or recombinant fragment of any of items (7.) to (9.), which proteolytic fragments may be prepared by chemical degradation and/or enzymatic proteolysis;
12. at least partially purified, such as at least substantially pure, retinal S-antigen protein isolated from animal ocular sources such as bovine, ovine or porcine;
13. a composition including proteolytic fragments of the composition of item (12.), which proteolytic fragments may be prepared by partial chemical degradation and/or enzymatic proteolysis;
14. a synthetic peptide 16 amino acids to 50 amino acids in length, said peptide including or consisting of the sequence VTVDVTNNTEKTVKK (SEQ ID NO: 3) or a variant thereof in which one or two amino acids are substituted with a different amino acid and amino acid sequence contiguous thereto from SEQ ID NO:1 or SEQ ID NO: 11, on either or both sides of SEQ ID NO: 3;
15. a synthetic peptide 16 amino acids to 50 amino acids in length, said peptide including or consisting of a contiguous sequence of SEQ ID NO:1 or SEQ ID NO: 11 that includes VTVDVTNNTEKTVKK (SEQ ID NO: 3), or a variant of said contiguous sequence that is at least 90% or at least 95% identical to said contiguous sequence;
16. a synthetic peptide 21 amino acids to 50 amino acids in length, said peptide including or consisting of the sequence GEPIPVTVDVTNNTEKTVKK (SEQ ID NO: 2) or a variant thereof in which one, two or three amino acids are substituted with a different amino acid, and amino acid sequence contiguous thereto from SEQ ID NO:1 or SEQ ID NO: 11, on either or both sides of SEQ ID NO: 3;
17. a synthetic peptide 21 amino acids to 50 amino acids in length, said peptide including or consisting of a contiguous sequence of SEQ ID NO:1 or SEQ ID NO: 11 that includes GEPIPVTVDVTNNTEKTVKK (SEQ ID NO: 2), or a variant of said contiguous sequence that is at least 90% or at least 95% identical to said contiguous sequence; and
repeating the administration step for a plurality of days.

An increase in regulatory immune cells in the patient, such as regulatory T-cells, responsive to the administered peptide, polypeptide or composition or to the peptide VTVDVTNNTEKTVKK (SEQ ID NO: 3) or a variant thereof in which one or two amino acid are substituted with a different amino acid can result.

The embodiment may include the further step of: co-administering to the human patient at least one enhancer selected from the group consisting of: high molecular weight hyaluronic acid; IL-2; IL-15; TGF-β; all-trans retinoic acid; rapamycin; anti-CD3; anti-CD28; vitamin D3; dexamethasone; IL-10; idolamine-2,3-dioxygenase; FTY720; a sphingosine kinase 1 inhibitor; cholera toxin B subunit; ovalbumin; Flt2L; sirolimus; anti-thymocyte globulin; and CTLA-4/Ig.

Another embodiment of the invention provides a method for preparing a cellular composition for the treatment of age-related macular degeneration that includes the steps of:
providing a composition as set forth in any of items (1.) through (12.) in the preceding embodiment; and
contacting regulatory immune cells in in vitro culture with said composition thereby training the regulatory immune cells.
A related embodiment provides the resulting cellular composition including the trained regulatory immune cells.

The culture of the cells may be continued in the presence of said composition over a course of days. The regulatory immune cells in in vitro culture may be or include cells selected from the group consisting of: $CD4^+CD25^+$ T-cells, $CD4^+Foxp3^+$ T-cells, $CD4^+CD25^+Foxp3^+$ T-cells, IL-10 producing $CD4^+$ Tr1 cells, TGF-β producing Th3 cells, $CD8^+$ NKT cells, $CD4^-CD8^-$ T-cells, γδ T-cells, thymic nT-reg cells, periphery induced i-Treg cells, tolerogenic dendritic cells (DC), $CD4^+CD127^{lo/-}$ T-cells, $CD4^+CD127^{lo/-}CD25^+$ T-cells, and the $CD45RA^+$ subset of $CD4^+CD127^{lo/-}CD25^+$ T-cells.

The trained regulatory cells may be administered, for example, by intravenous infusion or suitable injection, to a human patient in need of treatment for age-related macular degeneration once, or multiple times on different days. The regulatory immune cells may be autologous or heterologous to the human patient.

A further embodiment of the invention provides a method for identifying a peptide comprising an epitope as a candidate for inducing immune tolerance in a human patient having age-related macular degeneration that includes the steps of:
a. providing a library or a collection of different synthetic peptides, for example, having lengths in the range of 5-50 amino acids, such as 10-30 amino acids, such as 14-25 amino acids, such as 15-20 amino acids, or any length or sub-range in said ranges such as 15 or 20 amino acids amino acids, wherein, for example, the sequences of the synthetic peptides are at least 90% identical to a contiguous amino acid sequence of a mammalian retinal S-antigen, SEQ ID NO: 1 or SEQ ID NO: 11;
b. providing in vitro:
i. responder immune cells from a healthy human individual without age-related macular degeneration,
ii. regulatory immune cells from a healthy human individual without age-related macular degeneration,
iii. responder immune cells from a human patient having age-related macular degeneration, and
iv. regulatory immune cells from the human patient;

c. for each of a plurality of peptides of the library or the collection, measuring in vitro:
   i. a response thereto (RespH) from the responder immune cells of the healthy human individual,
   ii. a response thereto (RespP) from the responder immune cells of the human patient,
   iii. a response thereto (RegH) from regulatory immune cells of the healthy individual, and
   iv. a response thereto (RegP) from regulatory immune cells of the human patient; and
d. selecting a peptide from step (c.) that:
   i. elicits a response (RespH) from the responder immune cells of the healthy human individual,
   ii. elicits a response (RespP) from the responder immune cells of the human patient,
   iii. elicits a response (RegH) from the regulatory immune cells of the healthy individual,
   iv. elicits a response (RegP) from the regulatory immune cells of the human patient, and
   v. induces a RespH/RespP<1, a RegH/RegP≥1 or a RespH/RespP<1 and a RegH/RegP≥1,
   wherein the peptide selected in step (d.) is a candidate for inducing immune tolerance in a human patient having age-related macular degeneration.

The method may further include the step of: (e.) synthesizing the peptide selected in step (d.) of the embodiment. Said peptide may, for example, be synthesized in an amount of at least 5 mg, at least 20 mg, at least 50 mg, at least 100 mg, at least 500 mg, at least 1 gram, at least 5 grams, at least 10 grams, at least 100 grams or at least 500 grams.

The method may further include the step of: (f) contacting human regulatory immune cells in in vitro culture with the peptide synthesized in step (e.), thereby training the regulatory immune cells. In this manner, a composition including trained regulatory immune cells may be obtained. A method of treating age-related macular degeneration in a human patient is still further provided by administering the human regulatory immune (autologous or heterologous) using the peptide synthesized in step (e.) to a human patient in need of treatment for age-related macular degeneration, for example, via intravenous infusion or other suitable injection.

A different method for treating age-related macular degeneration (AMD) in a human patient, comprising the steps of: administering, via oral ingestion, to a human patient having age-related macular degeneration a therapeutically effective amount of the peptide synthesized in step (e.); and repeating the administration step for a plurality of days. An increase in the number of regulatory T-cells responsive to the synthetic peptide can result in the human patient.

9. EXAMPLES

This section describes various different working examples that will be used to highlight the features of the invention(s).

9.1. Example 1: Immune Cell Reactivity to Antigens in AMD Patients

In our evaluation of patients with AMD, we discovered marked immunological similarities to patients with uveitis. In AMD patients, we have seen activation of the acquired immune system, evidence of antigen sensitization as measured by proliferative responses by T cells, elevation of IL-17 cytokines and other members of that family, up-regulation of IL-17RC in the macula, and an M2 to M1 macular switch, all of which are seen in uveitis. These characteristics make AMD a promising candidate for down-regulatory immune therapy with oral administration of antigen or other epitope-tolerizing strategies. Accordingly, peripheral blood mononuclear cells of AMD patients were tested to determine whether they would manifest the same type of responses to various synthetic peptides as blood cells from uveitis patients did in an earlier study. See deSmet et al. (2001) Investigative Ophthalmology & Visual Science 42(13):3233-38.

The cell preparation and assay procedures used in these experiments were essentially as described in DeSmet et al. 2001. In brief, mononuclear lymphocytes were separated on isolymph gradient (Gallard-Schlesinger, Carle Place, N.Y.) from heparinized blood shortly after the sample was obtained. Cells were resuspended in RMPI 1640 with HEPES (Gibco, Grand Island, N.Y.), supplemented with glutamine (2 mM), Penicillin (100 U/ml), streptomycin (100 µg/ml), and 10% commercial heat-inactivated human AB serum (Biocell Laboratories, Carson, Calif.). These cells were immediately placed in culture at a density of $5 \times 10^5$ cells/well in the presence of a test peptide at a concentration of 20 µg/ml (or no peptide control), in flat-bottomed, 96-well plates (Costar, Cambridge, Mass.). All assays were plated in triplicate. Peptides were tested simultaneously. For control of immune reactivity, purified protein derivative (PPD; Parke-Davis, Morris Plains, N.J.) and purified phytohemagglutinin (PHA; Murex Diagnostics, Dartford, UK) were also tested. For the last 12 hours before harvesting at day 5, each well was pulsed with [3H]thymidine (2 Ci/mmol, 0.5 µCi per 10 µl/well; New England Nuclear, Boston, Mass.).

9.1.1. Experimental Results 1

The immunostimulatory activity of various 15-mer peptide subsequences of human S-Antigen on peripheral blood mononuclear cells (PBMCs) from AMD patients was tested and measured. The human S-antigen derived sequences of the tested peptides were:

```
Peptide 2 (P2):
                                        (SEQ ID NO: 5)
IFKKI SRDKS VTIYL Peptide 6 (P6):
                                        (SEQ ID NO: 6)
VKGKK VYVTL TCAFR Peptide 8 (P8):
                                        (SEQ ID NO: 7)
YGQED VDVIG LTFRR Peptide 23 (P23):
                                        (SEQ ID NO: 3)
VTVDV TNNTE KTVKK Peptide 29 (P29):
                                        (SEQ ID NO: 8)
LPLLA NNRER RGIAL Peptide 31 (P31):
                                        (SEQ ID NO: 9)
DTNLA SSTII KEGID
```

For comparison, two other peptides (PDS-Ag and B27PD) previously found to be immunostimulatory in uveitis patients (Wildner and Thurau 1994 Eur J Immunol 24; 2579-2585; Thurau et al., 1997 Immunology Letters 57; 193-201) were also included in this assay.

PDS-Ag:
(SEQ ID NO: 10)
FLGEL TSSEV ATEV

B27PD:
(SEQ ID NO: 4)
ALNED LSSWT AADT

In this experiment, PBMCs were obtained from patients having an advanced form of AMD called choroidal neovascularization (CNV) which is often referred to as "wet AMD," a condition that can lead to severe central vision loss. Results are shown in FIG. 1. The two peptides previously observed to have immunostimulatory effects in uveitis (PDS-Ag and B27PD) also elicit immunoreactive responses in patients with CNV. One of the new peptides tested, Peptide 23, elicited strong immunostimulatory responses from PBMCs of many of the CNV patients.

9.1.2. Experimental Results 2

Progression of AMD from early stages to late stages is characterized by size increases in drusen, which are extracellular deposits of fatty lipid and protein deposits underneath the retina, culminating in the neovascularization of advanced AMD. Accordingly, the immunostimulatory effects of the peptides in Experiment 1 were tested in patients who had different drusen size as a marker of the degree of AMD progression. This experiment was carried out as described in Example 1, with the results, stratified by drusen size. FIG. 2A shows the immunostimulatory activity of the various 15-mer peptide subsequences of human S-antigen on PBMCs from AMD patients with large drusen. FIG. 2B shows the immunostimulatory activity of the various 15-mer peptide subsequences of human S-antigen on PBMCs from AMD patients with medium drusen. FIG. 2C shows the immunostimulatory activity of the various 15-mer peptide subsequences of human S-antigen on PBMCs from early stage AMD patients with small drusen. FIG. 2D shows the immunostimulatory activity of the various 15-mer peptide subsequences of human S-antigen on PBMCs from control subjects without AMD.

As seen in FIG. 2C, peptides 23, 29 and 31 were the most reactive for PBMCs of patients with early AMD (small drusen). As seen in FIG. 2B, in PBMCs of patients with a later stage of AMD with medium size drusen, Peptide 23 demonstrated the highest reactivity. In PBMCs of patients with a still later stage of AMD with large drusen (FIG. 2A), reactivity to Peptide 23 and the other peptides tapered off with Peptide 29 and Peptide 31 demonstrating higher average reactivity than Peptide 23.

9.1.3. Experimental Results 3

Since Peptide 23 demonstrated particularly potent immunostimulation of PBMCs of AMD patients, further efforts were focused upon this peptide. In this experiment, Peptide 23 was tested for a variety of patients exhibiting varying degrees of progression to see if an association exists between the extent of immunostimulation by the peptide and the degree of disease progression (and thus also whether the extent of immunostimulation could be used for diagnostic purposes). The control specimens (patients without AMD) showed little if any stimulation by Peptide 23, whereas early and intermediate stage AMD samples (from patients with small and medium drusen, respectively) frequently show high levels of immunostimulation. Peptide 23 immunoreactivity is less predictive for late stage AMD (large drusen) samples than it is for intermediate and early stage AMD samples. Interestingly, the advanced CNV form of AMD shows a wide spectrum of immunoreactivity reactivity to Peptide 23.

9.1.4. Experimental Results 4

PBMC were obtained from AMD patients with large drusen and tested with PDS-Ag (SEQ ID NO: 10), B27PD (SEQ ID NO: 4) and Peptide 23 (SEQ ID NO: 3) to compare immune reactivities. As shown in FIG. 3, varying levels of responses were seen for all three agents tested, but Peptide 23 more frequently induced an immunostimulatory response than PDS-Ag or B27PD. In this experiment, PBMCs from the control subjects (without AMD) all showed essentially no reactivity to the test S—Ag/peptides demonstrating that the immune stimulation by the test agents is disease-specific.

9.1.5. Experimental Results 5

In addition to the PBMCs obtained from the patient with large drusen, PBMCs from patients with small and medium drusen were also tested for immunostimulation by Peptide 23 (SEQ ID NO: 23). FIG. 4 compares the Peptide 23 immunostimulation results obtained for PBMCs from large drusen, medium drusen, small drusen and control (human subject without AMD) samples. For all stages of AMD in this example, the AMD patient PBMC stimulation results are distinguishable from the control subject (without AMD) PBMC stimulation results.

FIG. 5 provides the results of a similar experiment demonstrating immunostimulatory activity of Peptide 23 (SEQ ID NO: 3) on PMBCs from AMD patients with CNV, large drusen, intermediate drusen, and small drusen and its effect on PBMCs from a control human subject without AMD (normal control) and the measured activity for PBMCs from a control human subject without AMD that were not exposed to Peptide 23 (normal control w/o P23).

9.2. Example 2: S-Antigen Peptide as AMD Oral Tolerizing Agent

The objective of this study is to evaluate the safety and efficacy of the peptide VTVDVTNNTEKTVKK (SEQ ID NO: 3) as a long term method to prevent the development of more advanced AMD employing oral tolerance. Oral tolerance is investigated in patients with intermediate drusen who have a high risk of developing intermediate (large drusen with or without pigmentary changes) or late AMD. The primary outcome is the development of large drusen or late AMD. An important secondary outcome is defined as a mean change drusen volume on SD-OCT over 5 years without progression to geographic atrophy or neovascular disease. Participants who progress to advanced disease are considered treatment failures, and censured from the drusen change analysis at the time late AMD develops.

Drusen is measured by the use of the scanning laser ophthalmoscopy (SLO). In a pilot study, drusen number and area grades were significantly higher using the right side (AR) and left side (AL) in which the laterally scattered light is captured (retromode). See Diniz et al. (2013) Br. J. Ophthalmol. 97(3):285-90. Use of the lateral confocal aperture may highlight subclinical drusen and aid in monitoring disease progression and response to emerging non-neovascular AMD therapies.

Target Population

Participants have early and intermediate AMD with intermediate drusen in both eyes or large drusen (with or without pigment changes) in one eye and intermediate drusen in the fellow eye. All study eyes have intermediate drusen (<63 μm).

Methods

This is a 5-year double-masked randomized clinical trial of 145 participants to assess the safety and efficacy of oral tolerance induction using drusen volume on OCT as a clinical end point. Patients are randomized 1:1 to the fragment of retinal S-Antigen having the sequence VTVDVTNNTEKTVKK (SEQ ID NO: 3) at 4 mg oral (ingested) daily or placebo oral (ingested) daily.

Study Outcome

The primary outcome is the development of large drusen or late AMD in patients with bilateral medium drusen or eyes whose fellow eye has large drusen. An important secondary outcome is defined as a mean change drusen volume on SD-OCT over 5 years without progression to geographic atrophy or neovascular disease. Participants who progress to advanced disease are considered treatment failures, and censured from the drusen change analysis at the time late AMD develops.

Other secondary outcomes in study eyes include:

Progression from intermediate drusen to large drusen or late AMD

Change in Dark Adaptation time

Mean change in best-corrected ETDRS (Early Treatment of Diabetic Retinopathy Study protocol) visual acuity from baseline to year-1.

Changes in autofluorescence patterns on fundus autofluorescence photography

Correlation with levels of serum inflammatory cytokines

Correlation with flow cytometry evaluating T regulatory cells

Correlation with epigenetic changes (demethylation of interleukin-17 receptor C)

Changes in chromaticity coordinates on Cambridge color test (Regan et al., 1994)

Safety outcomes

Changes in drusen volume through year-5 (USC protocol)

Sample Size Consideration

Detecting a 50% decrease in the development of large drusen or late AMD in patients with bilateral medium drusen or eyes whose fellow eye has large drusen, requires 132 patients with an α of 0.05 and of 0.2. A 10% adjustment for loss to follow-up and non-compliance would increases the required sample size to 145.

Using a 0.041 mm change in cube root drusen volume, as compared to the reference mean change, has a power of 80.6%. This is based on a 0.16 mm mean change in cube root volume for this drusen size population (Yehoshua and Gregori, 2011) and reflects a mean change of −0.025 mm in cube root volume in the treatment group.

Hazards and Discomforts

Possible complications associated with the study may include:

Temporary gastrointestinal upset from either placebo and/or S-antigen peptide.

Transient ocular discomfort from ocular examination.

Temporary discomfort, bruising or infection from blood draw.

9.3. Example 3: Activation of T-Reg Cells and Analysis of Suppressive Function Preparation of Cells and Solutions $CD4^+CD25^-$ (responder) and $CD4^+CD25^+$ (regulatory/suppressor) T-cell suspensions in RPMI-10 may be prepared as described in Thornton (2003) Current Protocols in Immunology, Unit 3.5A (DOI: 10.1002/0471142735.im0305as57). Cells are counted and $CD4^+CD25^-$ and $CD4^+CD25^+$ cells are adjusted to $1 \times 10^6$ cells/mL with RPMI-10 medium.

Accessory cells in RPMI-10 may be prepared as described in Thornton (2003). The accessory cells may consist of a preparation of spleen cells depleted of T-cells and optionally treated to prevent proliferation, such as by γ irradiation or with mitomycin C. Cells are counted and adjusted to $1 \times 10^6$ cells/mL with RPMI-10. The following working solutions are prepared: 1 μg/mL anti-CD3 in RPMI-10; 200 U/mL IL-2 in RPMI-10; and 2 μg/mL anti-CD28 in RPMI-10.

50 μL of $CD4^+CD25^+$ cells are added to each of nine wells of a 96-well flat-bottom microtiter plate and 50 μL of $CD4^+CD25^+$ cells are added to each of nine wells of a 96-well flat-bottom microtiter plate. 50 μL of accessory cells and 50 μL of 1 50 μg/mL anti-CD3 are added to each of the wells. 50 μL of 200 U/mL IL-2 are added to three wells of the $CD25^+$ cells and three wells of the $CD25^+$ cells.

Suppressive Function Assay

50 μL of $CD4^+CD25^+$ cells are added to three wells of a 96-well microtiter plate. A series of 3-4 two-fold dilutions of the $CD4^+CD25^+$ cells are made and control wells containing only 50 μL of RPMI-10 medium are included. After serial dilution, the starting number of cells in the wells are: $5 \times 10^4$ $CD25^+$ cells/well, $2.5 \times 10^4$ $CD25^+$ cells/well, $1.25 \times 10^4$ $CD25^+$ cells/well, $0.625 \times 10^4$ $CD25^+$ cells/well and $0.3 \times 10^4$ $CD25^+$ cells/well.

50 μL of $CD4^+CD25^-$ cells, 50 μL of accessory cells and 50 μL of 1 μg/mL anti-CD3 are added to the wells. The microtiter plates are placed in a 37° C., 5%-7% $CO_2$ humidified incubator for 3 days (about 66 hours).

On the morning of the third day [$^3$H]thymidine is added to each well and plates are returned to the incubator to pulse for 6-8 hours. Cells are harvested using a semiautomated sample harvester and counts per minute are measured in a β scintillation counter.

Results $CD4^+CD25^+$ cells are non-responsive to stimulation with anti-CD3 and accessory cells. Addition of anti-CD28 to $CD4^+CD25^+$ cells stimulated with anti-CD3 and accessory cells does not restore proliferation of these cells. The addition of anti-CD28 to CD4+$CD25^+$ cells enhances their proliferation. Addition of IL-2 to $CD4^+CD25^+$ cells results in proliferation of these cells. Addition of $CD4^+CD25^+$ cells to $CD4^+CD25^+$ cells results in a dose-dependent decrease in the proliferation of $CD4^+CD25^+$ cells.

9.4. Example 4: Activation and Expansion of $CD4^+CD25^+$ T-Cells and Analysis of Suppressive Function Activation of $CD4^+CD25^+$ T-cells $CD4^+CD25^+$ T-reg cells are purified in complete RMPI-10 medium supplemented with 100 U/mL IL-2 as described in Thornton (2003) Current Protocols in Immunology, Unit 3.5A (DOI: 10.1002/0471142735.im0305as57). $CD4^+CD25^+$ cells are counted and adjusted to $1 \times 10^6$ cells/mL with RPMI-10/IL-2.

A working solution of 5 µg/mL anti-CD3 in PBS is prepared. 300 µL of anti-CD3 solution is added to each well of a 24-well plate. Number of wells to be coated is based on anticipated yield of CD4$^+$CD25$^+$ cells. Plates are incubated for 90 min in a 37° C., 5%-7% $CO_2$ humidified incubator. Antibody is removed from the plates and wells are washed 2× with PBS to remove excess antibody. 1 mL containing 1×10$^6$ CD4$^+$CD25$^+$ cells are added to the wells. Plates are placed in a 37° C., 5%-7% $CO_2$ humidified incubator for 3 days. CD4$^+$CD25$^+$ cells are fully activated but are not greatly expanded.

After three days, cells are split 1:3 or 1:4 in RPMI-10 medium supplemented with 100 U/mL IL-2 and are returned to the a 37° C., 5%-7% $CO_2$ humidified incubator.

Suppressive Function Assay

Activated CD4$^+$CD25$^+$ T-reg cells are harvested by pipetting up and down rigorously. Cells are centrifuged for 10 min at 200×g (Sorvall H-1000B rotor at approx. 1000 rpm) at 4° C. Cells are washed 2× to completely remove remaining IL-2 and resuspend in RPMI-10. Cells are adjusted to 1×10$^6$ cells/mL with RPMI-10.

CD4$^+$ T-cell suspension in RPMI-10 is prepared from TCR transgenic mice as described in Unit 3.5A of Thornton (2003). CD4$^+$ cells are counted and adjusted to 1×10$^6$ cells/mL with RPMI-10. Antigen at 4× is diluted to the desired final concentration with RPMI-10. 50 µL of CD4$^+$CD25$^+$ cells are added to three wells of a 96-well microtiter plate. A series of 3-4 two-fold dilutions of CD4$^+$CD25$^+$ cells are made and control wells containing 50 µL of RPMI-10 are included. After serial dilution, the starting number of cells in the wells are: 5×10$^4$ CD25$^+$ cells/well, 2.5×10$^4$ CD25$^+$ cells/well, 1.25×10$^4$ CD25$^+$ cells/well, 0.625×10$^4$ CD25$^+$ cells/well and 0.3×10$^4$ CD25$^+$ cells/well.

50 µL TCR Tg CD4$^+$ T-resp cells, 50 µL of accessory cells and 50 µL of antigen are added to each well. The microtiter plates are placed in a 37° C., 5%-7% $CO_2$ humidified incubator for 3 days (about 66 hours).

On the morning of the third day [$^3$H]thymidine is added to each well and plates are returned to the incubator to pulse for 6-8 hours. Cells are harvested using a semiautomated sample harvester and counts per minute are measured in a β scintillation counter.

9.5. Example 5: In Vitro Identification of a Compound Comprising an Epitope that Induces Immune Tolerance Overlapping oligomeric peptide determinants of human HLA-B27 (Accession no. CAA27578.1) spanning the length of the protein are synthesized on an automated peptide synthesizer (Intavis, AG, Koeln, Germany). Each peptide is 15 amino acids in length and overlaps the previous peptide by 3 amino acids. Peptides are purified by HPLC to at least 95% purity. The amino acid composition of peptides is verified using amino acid analysis and automated gas-phase sequencing.

CD4$^+$CD25$^+$ T-reg cells are prepared as described in Example 3, above. 50 µL of CD4$^+$CD25$^+$ cells, 50 µL of accessory cells and 50 µL of 1 µg/mL anti-CD3 are added to the wells of a 96-well microtiter plate. HLA-B27 peptide is added to each well except for the control wells. All peptides are assayed in triplicate (3 wells each). The microtiter plates are placed in a 37° C., 5%-7% $CO_2$ humidified incubator for 3 days (about 66 hours).

On the morning of the third day [$^3$H]thymidine is added to each well and plates are returned to the incubator to pulse for 6-8 hours. Cells are harvested using a semiautomated sample harvester and counts per minute are measured in a β scintillation counter.

The peptide that elicits the largest CD4$^+$CD25$^+$ cell proliferation as measured by levels of [$^3$H]thymidine as compared CD4$^+$CD25$^+$ cell proliferation in the absence of peptide is a peptide that elicits immune tolerance in a patient or a candidate therefor.

9.6. Example 6: Administration of T-Reg Cells to Patients Suffering from Type-I Diabetes Mellitus T-reg cells from partially HLA-matched healthy individuals are prepared as set forth in Trzonkowski et al. (2009) Clin. Immunol. 133:22-26 and Marek et al. (2011) Cell Transplant 12:1747-1758. T-regs are cultured in the presence of 10% autologous serum, IL-2 (1000 U/mL) and clinical-grade anti-CD3/anti-CD28 beads in a 1:1 ratio with cells. Cells may be cultured for about 10 days to 2 weeks. The period of culture may be no longer than 2 weeks.

T-reg cells for infusion are washed out completely, suspended in 250 mL 0.9% NaCl and transferred in slow infusion to a patient under anesthesia within 1 hour. T-regs are administered in a dose from 10×10$^6$/kg body weight to 20×10$^6$/kg body weight.

The endpoint is fasting C-peptide, HbA$_{1c}$ level and insulin requirement. The percentage of T-regs in the patient's blood after 2 weeks, 2 months, 4 months and 6 months is assayed. If the percentage of T-regs drops by 50%, a compound as identified by the methods described herein is administered to the patient.

9.7. Example 7: Identification of Peptides with Sequence Homology to S-Antigen Peptide GEPIPVTVDVTNNTEKTVKK (SEQ ID NO: 2)

The receptor of IL-17 has been shown to be hypomethylated and over-expressed in patients with age-related macular degeneration. IL-17RC, an allelic form of the IL-17 receptor, is highly expressed in macular tissue of AMD patients, but not in tissue of healthy individuals. See Wei et al. (2012) Cell Reports 2:1151-1158; and WO 2012/103187.

The peptide of S-antigen elicits a response from responder T-cells of AMD patients, but does not elicit a response from responder T-cells of healthy individuals. See FIG. 1. A BLAST search using GEPIPVTVDVTNNTEKTVKK (SEQ ID NO: 2) as the query sequence was performed and showed that there is significant homology between this peptide of S-antigen and IL-17RC. The homology between IL-17RC isomers 5 and 6 and GEPIPVTVDVTNNTEKTVKK (SEQ ID NO: 2) is the result of a deletion of Exon 12 of the IL-17RC gene and fusion of Exons 11 and 13. See Haudenschild et al. (2002) J. Biol. Chem. 277(6):4309-4316, FIGS. 1 and 2. IL-17RC isoforms that have a deletion of Exon 12 cannot bind IL-17A or IL-17F. See Kuestner et al. (2007) J. Immunol. 179:5462-5473.

In addition, the BLAST search showed that GEPIPVTVDVTNNTEKTVKK (SEQ ID NO: 2) has significant homology not only to IL-17RC isoforms, but also to a number of sequences from pathogenic organisms. This homology to pathogenic organisms in the case of AMD raises the question of whether infection by one or more infectious agents that have proteins that are homologous to proteins in the human body results in an aberrant immune response that leads to autoimmune disease.

Accordingly, epitopes that are demonstrated to react with regulatory T-cells and/or responder T-cells, and that belong to one class of protein, such as S-antigen, may be analyzed for homology with unrelated proteins from all sources, including humans and infectious agents. Such analyses could potentially lead to the etiology of an autoimmune disease, as well as to the design of more effective tolerizing epitopes and/or therapeutic agents. Furthermore, epitope homology may indicate not only a tolerizing epitope candidate, but also, a therapeutic effector that directly acts on the disease condition, e.g., that acts as an anti-inflammatory for a particular autoimmune disease.

For every embodiment disclosed herein that recites or otherwise relates to a mammalian S-antigen, such as human S-antigen, the invention also provides corresponding embodiments that relate instead to a mammalian Interleukin-17 receptor C protein, such as an isoform thereof, for example, a human Interleukin-17 receptor C protein, such as isoform 5 or 6 thereof. For every embodiment disclosed herein that recites or otherwise relates to human S-antigen SEQ ID NOS: 1 or 11, the invention also provides corresponding embodiments that relate instead to human Interleukin-17 receptor C isoform 5 (SEQ ID NO: 16) or human Interleukin-17 receptor C isoform 6 (SEQ ID NO: 15). Further, for every embodiment disclosed herein that recites or otherwise relates to SEQ ID NO: 2 or SEQ ID NO: 3 (Peptide 23), the invention also provides corresponding embodiments that relate instead to one or more of SEQ ID NOS: 12-14 and 17-25.

It should be noted that the indefinite articles "a" and "an" and the definite article "the" are used in the present application to mean one or more unless the context clearly dictates otherwise. Further, the term "or" is used in the present application to mean the disjunctive "or" or the conjunctive "and."

All publications, patents, patent applications and other documents cited in this application are hereby incorporated by reference in their entireties for all purposes to the same extent as if each individual publication, patent, patent application or other document were individually indicated to be incorporated by reference for all purposes. Any discussion of documents, acts, materials, devices, articles or the like that has been included in this specification is solely for the purpose of providing a context for the present disclosure. It is not to be taken as an admission that any or all of these matters form part of the prior art or were common general knowledge in the field relevant to the present disclosure as it existed anywhere before the priority date of this application.

While various specific embodiments have been illustrated and described, it will be appreciated that various changes can be made without departing from the spirit and scope of the invention(s). Moreover, features described in connection with one embodiment of the invention may be used in conjunction with other embodiments, even if not explicitly exemplified in combination within.

What is claimed is:

1. A pharmaceutical composition, comprising
a synthetic peptide which is GEPIPVTVDVTNNTEKTVKK (SEQ ID NO: 2) or VTVDVTNNTEKTVKK (SEQ ID NO: 3); and
transforming growth factor beta (TGF-β).

2. The pharmaceutical composition, comprising:
the synthetic peptide which is GEPIPVTVDVTNNTEKTVKK (SEQ ID NO: 2).

3. The pharmaceutical composition, comprising:
the synthetic peptide which is VTVDVTNNTEKTVKK (SEQ ID NO: 3).

4. The pharmaceutical composition of claim 1, consisting essentially of:
the synthetic peptide which is GEPIPVTVDVTNNTEKTVKK (SEQ ID NO: 2) or VTVDVTNNTEKTVKK (SEQ ID NO: 3); and
transforming growth factor beta (TGF-β).

5. The pharmaceutical composition of claim 4, consisting essentially of:
the synthetic peptide which is GEPIPVTVDVTNNTEKTVKK (SEQ ID NO: 2); and
transforming growth factor beta (TGF-β).

6. The pharmaceutical composition of claim 4, consisting essentially of:
the synthetic peptide which is VTVDVTNNTEKTVKK (SEQ ID NO: 3); and
transforming growth factor beta (TGF-β).

* * * * *